(12) United States Patent
Falco et al.

(10) Patent No.: US 7,368,633 B2
(45) Date of Patent: May 6, 2008

(54) PLANT AMINO ACID BIOSYNTHETIC ENZYMES

(75) Inventors: Saverio Carl Falco, Wilmington, DE (US); Zhan-Bin Liu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 17 days.

(21) Appl. No.: 10/917,602

(22) Filed: Aug. 13, 2004

(65) Prior Publication Data

US 2005/0120405 A1 Jun. 2, 2005

Related U.S. Application Data

(60) Continuation-in-part of application No. 10/734,698, filed on Dec. 12, 2003, now Pat. No. 7,022,895, which is a division of application No. 09/424,978, filed as application No. PCT/US98/11692 on Jun. 5, 1998, now Pat. No. 6,664,445.

(60) Provisional application No. 60/048,771, filed on Jun. 6, 1997, provisional application No. 60/049,443, filed on Jun. 12, 1997.

(51) Int. Cl.
*C12N 15/52* (2006.01)
*C07H 21/04* (2006.01)
*C07K 14/415* (2006.01)
*C12N 5/14* (2006.01)
*C12N 9/00* (2006.01)
*A01H 1/00* (2006.01)

(52) U.S. Cl. .................. 800/295; 435/6; 435/468; 435/69.1; 435/419; 435/252.3; 435/320.1; 435/183; 530/370; 536/23.6; 800/278

(58) Field of Classification Search ............ 435/6, 435/69.1, 468, 419, 252.3, 320.1, 183; 530/370, 530/23.6; 800/278, 295
See application file for complete search history.

(56) References Cited

U.S. PATENT DOCUMENTS

| | | | |
|---|---|---|---|
| 5,231,020 | A | 7/1993 | Jorgensen et al. |
| 5,451,516 | A | 9/1995 | Matthews et al. .......... 435/190 |
| 5,545,545 | A | 8/1996 | Gengenbach et al. .... 435/172.3 |
| 2004/0031072 | A1* | 2/2004 | La Rosa et al. ............ 800/278 |

FOREIGN PATENT DOCUMENTS

| | | |
|---|---|---|
| EP | 0485790 A2 | 11/1991 |
| WO | WO 96/01905 | 1/1996 |
| WO | WO 96/38574 | 12/1996 |
| WO | WO 97/07665 | 3/1997 |

OTHER PUBLICATIONS

EMBL Database Sequence Library, Accession No. Z26867, Oct. 11, 1993, F. Van Breusegem et al., Characterization of a S-Adenosylmethionine Synthetase Gene in Rice.
EMBL Database Sequence Library, Accession No. Z24741, Nov. 23, 1993, J. Espartero et al., Differential Expression of Three S-Adenosylmethionine Synthase Genes in Response to Stress in Tomato.
Dae Gun Kim et al., Purification and Characterization of S-Adenosylmethionine Synthetase From Soybean (Glycine Max) Axes, J. Biochem. Mol. Biol., vol. 28(2):100-106, 1995.
Pascal Touzet et al., Characterizing Allelic Proteins for Genome Mapping in Maize, Electrophoresis, vol. 16:1289-1294, 1995.
Hein, J. J. (1990) Meth. Enz. 183:626-645.
Bieleski et al. (1996) Anal. Biochem. 17:278-293.
Farkas et al. (1965) J. Biol. Chem. 240:4717-4722.
Cremer et al. (1988) J. Gen. Microbiol. 134:3221-3229.
Giovanelli et al. (1984) Plant Physiol. 76:285-292.
Curien et al. (1996) FEBS Lett. 390:85-90.
Tomova et al. (1968) Biochemistry (USSR) 33:200-208.
Dougall (1970) Phytochemistry 9:959-964.
Mudd (1960) Biochim. Biophys. Acta 38:354-355.
Boerjan et al. (1994) Plant Cell 6:1401-1414.
Feng, et al, EMBL Sequence Data Library, XP002078204, May 10, 1997.
Saito, et al, "Modulation of Cystein Biosynthesis in Chloroplasts of Transgenic Tobacco Overexpressing Cysteine Synthase [O-Acetylserine(thiol)-lyase]", *Plant Physiology*, 106, 1996, 887-895.
Youssefian, et al, "Tobacco Plants Transformed with the O-acetylserine (thiol) lyaseGene of Wheat are Resistant to Toxic Levels of Hydrogen Sulphide Gas", *The Plant Journal* (1993), 4, No. 5, 759-769.
Curien, et al, "Characterization of an *Arabidopsis thaliana* cDNA Encoding an S-adenosylmethionine Sensitive Threonine Synthase", *EMBL Sequence Data Library*, XP002078253, Jul. 26, 1996.
Espartero, et al, "Differential Accumulation of S-adenosylmethionine Synthetase Transcripts in Response to Salt Stress", *EMBL Sequence Data Library*, XP002078254, Nov. 23, 1993.
Schwartz, et al, *EMBL Sequence Data Library*, XP002078255, Jun. 8, 1996.
Bork, P. Genome Research, vol. 10, 2000, p. 398-400.
Lazar et al. Molecular and Cellular Biology, Mar. 1988, vol. 8, No. 3, p. 1247-1252.
Burgess et al. The Journal of Cell Biology, 1990, vol. 111, p. 2129-2138.
Broun et al. Science, Nov. 13, 1998, vol. 282, p. 131-133.
Van Breusegem et al. Plant Physiology. vol. 105, p. 1463-1464, 1994.
Goodenough, U. Genetics, 2nd edition, Holt, Rinehart and Winston, Pub., p. 322-328, 1978.

* cited by examiner

*Primary Examiner*—Phuong Bui

(57) ABSTRACT

This invention relates to an isolated nucleic acid fragment encoding a plant enzyme that catalyze steps in the biosynthesis of lysine, threonine, methionine, cysteine and isoleucine from aspartate, the enzyme a member selected from the group consisting of: dihydrodipicolinate reductase, diaminopimelate epimerase, threonine synthase, threonine deaminase and S-adenosylmethionine synthetase. The invention also relates to the construction of a chimeric gene encoding all or a portion of the enzyme, in sense or antisense orientation, wherein expression of the chimeric gene results in production of altered levels of the enzyme in a transformed host cell.

9 Claims, 30 Drawing Sheets

FIG. 2

```
             1                                                          60
SEQ ID NO:4  ............................................................
SEQ ID NO:2  ..................................................KIGRRNAA..
SEQ ID NO:5  MANQDLIPVVVNGAAGKMGREVIKAVAQAPDLQLVGAVDHNPSLQGQDIGEVVGIAPLEV 61                                                         120
SEQ ID NO:4  .......KVLCSTQMPPSQSTI.....KVVIIGATKEIGRTAIAAVSKARGMELAGAID.
SEQ ID NO:2  PVLNDLTMVLGSIAQSRATGVVVDFSEPSAVYDNVKQAAAFGLSSVVYVPKIELETVTEL
SEQ ID NO:5  PVLADLQSVLVLATQEKIQGVMDFTHPSGVYDNVRSAIAYGVRPVVGTTGLSEQQIQDL 121                                                        180
SEQ ID NO:4  ......S.QCI...GLDAGEI..........................SGMGRTLEIPV.
SEQ ID NO:2  SAFCEKAS.GCLVAPTLSIGSVLLQQAAIQASFHYSNVEIVESRPNP.SDLPSQDAIQIA
SEQ ID NO:5  GDFAEKASTGCLIAPNFAIGVLLMQQAAVQACQYFDHVEIIELHHNQKADAPSGTAIKTA 181                                                        240
SEQ ID NO:4  ..LNDLTMV........LGSIAQTRA..........TGVV....VDFSEPSTVYD
SEQ ID NO:2  NNISDLGQIYNR...EDMDSSSPARGQLLGEDGVRVHSMVLPGLVSSTSINFSGPGEMYT
SEQ ID NO:5  QMLAEMGKTENPPAVEEKETIAGAKGGL.GPGQIPIHSIRLPGLIAHQEVLFGSPGQLYT 241             276
SEQ ID NO:4  NVKQA...................
SEQ ID NO:2  LRHDVANVQCLMPGLILAIRKVVRFKNLIYGLEKFL
SEQ ID NO:5  IRHDTTDRACYMPGVLLGIRKVVELKGLVYGLEKLL
```

FIG. 3A

```
                              1                                                           60
SEQ ID NO: 7   L...........................................................
SEQ ID NO: 9   VS..........................................................
SEQ ID NO:11   MAITATISVPLTSPSRRTLTSVNSLSPLSTRSTLPTPQRTFKYPNSRLVVSSMSTETAVK
SEQ ID NO:13   ............................................................
SEQ ID NO:14   ............................................................

61                                                          120
SEQ ID NO: 7   ............................................................
SEQ ID NO: 9   ....TSSASFLNRKESGFLHFAKYHGLGNDFVLIDNRDSSEPKISAEKAVQLCDRNFGVGADGV
SEQ ID NO:11   ............................................................GADGV
SEQ ID NO:13   ............ALHFVKYQGLGNDFIMVDNRDSAVPKVTPEEAAKLCDRNFGXGADGV
SEQ ID NO:14   .........MALSESKYHGLGNDFILVDNRQSTEPCLTPDQAQQLCDRHFGIGADGV 121                                                          180
SEQ ID NO: 7   .....................PEMCGNGVRCFARFIAEIENLQGTNRFTIHTGAGKIV
SEQ ID NO: 9   IFVMPGVNGADYTMRIFNSDGSEPEMCGNGVRCFARFIAELENLQGTHSFKIHTGAGLII
SEQ ID NO:11   IFVLPGISGTDYTMRIFNSDGSEPEMCGNGVRCFAKFVSQLENLHGRHSFTIHTGAGLII
SEQ ID NO:13   IFVLPGVNGADYTMRIFNSDGSNRRNVWX.GFV...........................
SEQ ID NO:14   IFALPGQGGTDYTMRIFNSDGSEPEMCGNGIRCLAKFLADLEGVEEK.TYRIHTLAGVIT 181                                                          240
SEQ ID NO: 7   PEIQSDGQVKVDMGEPILSGLDIPTKLLATKNKAVVQAELAVEGLTWHVTCVSMGNPHCV
SEQ ID NO: 9   PEIQNDGKVKVDMGQPILAC........................................
SEQ ID NO:11   PEVLEDGNVRVDMGEPVLKALDVPTKLPANKDNAVVKSQLVVDGVIWHVTCVSMGNPHCV
SEQ ID NO:13   ............................................................
SEQ ID NO:14   PQLLADGQVKVDMGEEPQLLAELIPTTLAPAGEK.VVDLPLAVAGQTWAVTCVSMGNPHCL
```

FIG. 3B

```
                 241                                                        300
SEQ ID NO: 7     TFGANELKVLQVDDLKLSEIGPKFEHHEMFPARTNTEFVQVLSRSHLKMRVWERGAGATL
SEQ ID NO: 9     ................TFSREGSQNLLVDELKLAEIGPKFEHHEVFPARTNTEFVQVLSNSHLKMRVWERGAGATL
SEQ ID NO:11     ............................................................
SEQ ID NO:13     ........TFVDD.......VDSLNLTEIGPLFEHHPQFSQRTNTEFIQVLGSDRLKMRVWERGAGITL
SEQ ID NO:14     ............................................................

301                                   359
SEQ ID NO: 7     ACGTGACACAVVVAAVLEGRAERKCVVDLPGGPLEIEWREDDNHVYMTGPAEVVFYGSVVH
SEQ ID NO: 9     ............................................................
SEQ ID NO:11     ACGTGACATVVAAVLEGRAGRNCTVDLPGGPLQIEWREEDNHVYMTGSADVVYGSLPL.
SEQ ID NO:13     ............................................................
SEQ ID NO:14     ACGTGACATVVAAVLTGRGDRRCTVELPGGNLEIEWSAQDNRLYMTGPAQRVFSGQAEI
```

FIG. 4A

```
SEQ ID NO:24    1  ASSSLFQSLPFSLQTSK.PYAPPKPAAHFVVRA..............QSPLTQNNNSSSKHRRPAQ  60
SEQ ID NO:26       ..............................................................
SEQ ID NO:27       .....LSSCLFNASVSSLNPKQDPIRRHRSTSLLRHRPVVISCTADGNNIKAPIETAVKPPHRTE

SEQ ID NO:20    61 ..............................................................  120
SEQ ID NO:22       ..............................................................
SEQ ID NO:24       ENIRDEARRINAPHDHHLFSAKYVPFNADSSSSSSTESYSLDEIVYRSQSGGLLDVQHDM..MENGAATNGASEKSHSPS
SEQ ID NO:26       ..............................................MENGAATNGASEKSHSPS
SEQ ID NO:27       DNIRDEARR.NRSNAVNPFSAKYVPFNA..APGSTESYSLDEIVYRSRSGGLLDVEHDM

SEQ ID NO:16    121 ..............................................................  180
SEQ ID NO:18       ..............................................................
SEQ ID NO:20       QTYLSTRGDDYGLSFETVV...........................................
SEQ ID NO:22       DALKRFDGEYWRNLFDSRVGKTTWPYGSGVWSKKEWVLPEIHDDDIVSAFEGNSNLFWAE
SEQ ID NO:24       ..............................................................
SEQ ID NO:26       EALKRFDGAYWRDLFDSRVGKSTWPYGSGVWSKKEWVLPEIDDDDIVSAFEGNSNLFWAE
SEQ ID NO:27       ..............................................................

SEQ ID NO:16    181 ..............................................VGCASTGDTSA  240
SEQ ID NO:18       LKGLAADGGLFLPEEVPAATEWQSWKDLPYTELAVKV..........................
SEQ ID NO:20       ..............................................................
SEQ ID NO:22       ..............................................................
SEQ ID NO:24       RFGKQFLGMNDLWVKHCGISHTGSFKDLGMTVLVSQVNRLRKMNRPVVGVGCASTGDTSA
SEQ ID NO:26       ..............................................................
SEQ ID NO:27       RFGKQFLGMNDLWVKHGGISHTGSFKDLGMTVLVSQVNRLRKMKRPVVGVGCASTGDTSA
```

FIG. 4B

```
              241                                                                           300
SEQ ID NO:16  ALSAYCAAAGIPAIVFLPADRISLQQLIQPIANGATVLSLDTDFDGCMRLIREVTAELPI
SEQ ID NO:18  .LSLYISPAEVPTE........DLRALVER...............................
SEQ ID NO:20  .............................................................
SEQ ID NO:22  ALSAYCASAAIPSIVFLPANKISLAQLVQPIANGAFVLSIDTDFDGCMQLIREVTAELPI
SEQ ID NO:24  ...............LIQPIANGATVLSLDTDFDGCMRLIREVTAELPI
SEQ ID NO:26  .............................................................
SEQ ID NO:27  ALSAYCASAGIPSIVFLPANKISMAQLVQPIANGAFVLSIDTDFDGCMKLIREITAELPI 301                                                                           360
SEQ ID NO:16  YLANSLNPL.RLEGQKTAAIEILQQFNWQVPDWVIVPGGNLGNIYAFYKGFEMCRVLGLV
SEQ ID NO:18  .............................................................
SEQ ID NO:20  ...........SYSTFRSKEVVPLVKLEDNLHLLELFHGPNYSF................
SEQ ID NO:22  YLANSLNSL.KLEGQKTAAIEILQQFDWQVPDWVIVPGSNLGNIYAFYKGFKMFQELGLV
SEQ ID NO:24  YLANSLNSL.XLEGQKTAAIRDIATXNWQVPGLGHIPRRQSXTFYAFLQGF..........
SEQ ID NO:26  .............................................................
SEQ ID NO:27  YLANSLNSL.RLEGQKTAAIEILQQFDWQVPDWVIVPGGNLGNIYAFYKGFKMCQELGLV 361                                                                           420
SEQ ID NO:16  DRVPRLVCAQAANANPLYRYYKSGWTEFEPQTAETTFASAIQIGDPVSVDRAVVALKATD
SEQ ID NO:18  .............................................................
SEQ ID NO:20  .............................................................
SEQ ID NO:22  DKIPRLVCAQAANADPLYLYFKSGWKEFKPVKSSTTFASAIQIGDPVSIDRAVHALKSCD
SEQ ID NO:24  ...............KDCALQFLGNLXEYF..............................
SEQ ID NO:26  .............................................................
SEQ ID NO:27  DRIPRMVCAQAANANPLYLHYKSGWKDFKPMTASTTFASTTFASAIQIGDPVSIDRAVYALKKCN 421                                                                           480
SEQ ID NO:16  GIVEEATEEELMDATALADRTGMFACPHTGVALAALFKLQGQRIIGPNDRTVVVSTAHGL
SEQ ID NO:18  .............................................................
SEQ ID NO:20  .............................................................
SEQ ID NO:22  DAMVQADSTGMFICPHTGVALAALIKLRNRGVIGAGERVVVVSTAHGL
SEQ ID NO:24  .............................................................
SEQ ID NO:26  GIVEEATEEELMDATAQADSTGMFICPHTGVALTALFKLRNSGVIKATDRTVVVSTAHGL
```

FIG. 4C

```
SEQ ID NO:27    GIVEEATEEELMDAMAQADSTGMFICPHTGVALTALFKLRNQGVIAPTQRTVVVSTAHGL 481                                                        537
SEQ ID NO:16    KFTQSKIDYHDKNIKDMVCQYANPPISVKADFGSVMDVLQKN......LNGKI...
SEQ ID NO:18    ................MACKYSNPPVSVKADFGAVMDVLKKR......LKGKL...
SEQ ID NO:20    ................................................
SEQ ID NO:22    KFAQSKIDYHSGLIPGMG.RYANPLVSVKADFGSVMDVLKDSCTTSPPTLTSLDVAK
SEQ ID NO:24    KFTQSKIDYHSKDIKDMACRYANPPMQVKADFGSVMDVLKTY......LQSKA..H
SEQ ID NO:26    ................................................
SEQ ID NO:27    KFTQSKIDYHSNAIPDMACRFSNPPVDVKADFGAVMDVLKSY......LGSNTLTS
```

FIG. 5A

```
                    1                                                           60
SEQ ID NO:29        ............................................................
SEQ ID NO:31        ............................................................
SEQ ID NO:33        ............................................................
SEQ ID NO:34        MASHDYLKKILTARVYDVAFETELEPARNLSARLRNPVYLKREDNQPVFSFKLRGAYNKM 61                                                          120
SEQ ID NO:29        ...................................................TVVLEGD
SEQ ID NO:31        ............................................................
SEQ ID NO:33        ............................................................
SEQ ID NO:34        .AHIPADALARGVITASAGNHAQGVAFSAARMGVKAVIVVPVTTPQVKVDAVRAHGGPGVE 121                                                         180
SEQ ID NO:29        SYDEAQSYAK......LRCQQE.GRTFVPPFDHPDVITGQGTIGMEIVRQLQGPLHAIFVP
SEQ ID NO:31        ............................................................
SEQ ID NO:33        ...........................................VIAGQGTIAMEILRQHQGPIHAIFVP
SEQ ID NO:34        VIQAGESYSDAYAHALKVQEERGLTFVHPFDDPYVIAGQGTIAMEILRQHQGPIHAIFVP 181                                                         240
SEQ ID NO:29        VGGGGLIAGIAAYVKRVRPEVKIIGVEPSDANAMALSLCHGKRVMLEHVGGFADGVAVKA
SEQ ID NO:31        ............................................................
SEQ ID NO:33        ............................................................
SEQ ID NO:34        IGGGGLAAGVAAYVKAVRPEIKVIGVQAEDSCAMAQSLQAGKRVELAEVGLFADGTAVKL 241                                                         300
SEQ ID NO:29        VGEETFRLCRELVDGIVMVSRDAICASIKDMFEEKRSILEPAGALALAGAEAYCKYYNLK
SEQ ID NO:31        ............................................................
SEQ ID NO:33        ...VGEETFRLCKEYLDGVVTVDTDALCAAIKDVFQDTRSVLEPSGALAVAGAKLYAEREGIE
SEQ ID NO:34        VGEETFRLCKEYLDGVVTVDTDALCAAIKDVFQDTRSVLEPSGALAVAGAKLYAEREGIE
```

FIG. 5B

```
              301                                                          360
SEQ ID NO:29  GETVVAITSGANMNFDRLRLVTELADVGRKREAVLATEFLPERQGSFKKFTELVGRMNITE
SEQ ID NO:31  ..NIVAITSGANMNFDKLRVVTELANVGRKQEAVLATVMAEEPGSFKQFCELVGQMNITE
SEQ ID NO:33  ............................................................
SEQ ID NO:34  NQTLVAVTSGANMNFDRMRFVAERAEVGEAREAVFAVTIPEERGSFKRFCSLVGDRNVTE 361                                                          420
SEQ ID NO:29  FKYRYDSNAKDALVLYSVGIYTDNELGAMMDRMESAKLRTVNLTDNDLAKDHLRYFIGGR
SEQ ID NO:31  FKYRYNSNEK.AVVLYSVGVHTISELRAMQERMESSQLKTYNLTESDLVKDHLRYLMGGR
SEQ ID NO:33  ............................................................
SEQ ID NO:34  FNYRI.ADAQSAHIFVGVQIRRRGESADIAANFESHGFKTADLTHDELSKEHIRYMVGGR 421                                                          480
SEQ ID NO:29  SEIK.DELVYRFIFPERPGALMKFLDTFSPRWNISLFHYRAQGEAGANVLVGIQVPPAEF
SEQ ID NO:31  SNVQ.NEVFVVSPXPRKTGALMKFLDXFSPRWDISL........................
SEQ ID NO:33  ..........RPGALMKFLDPFSPRWNISLFHYRGEGETGANVLVGIQVPKSEM
SEQ ID NO:34  SPLALDERLFREFPERPGALMKFLSSMAPDWNISLFHYRNQGADYSSILVGLQVPQADH 481                                  512
SEQ ID NO:29  DEFKSHANNLGYEYMSEHNNEIYRLLLRDPKV
SEQ ID NO:31  ...............................
SEQ ID NO:33  DEFHDRANKLGYDYKVVNDDDFQLLMH.....
SEQ ID NO:34  AEFERFLAALGYPYVEESANPAYRLFLS....
```

FIG. 6A

```
SEQ ID NO:36    126  GCAGATCAAAGAAGATGGCAGCTCTCGACACCTTCCTCTCTTCACCTCGGAGTCTGTGAACG  185
                     |||||    ||||||||||||||||| || ||    || ||||||||||||||||||||||
SEQ ID NO:37    774  GCAGATAGAGAAGATGGCCGCACTTGATACCTTCCTCTTTACCTCGGAGTCTGTGAACG  833

SEQ ID NO:36    186  AGGGACACCCTGACAAGCTCTGCGACCAGTCTCAGATGCCGTTCTTGACGCTTGCCTTG  245
                     |||| ||||||||||||||||||||||||||||||||||||| || ||    ||||||
SEQ ID NO:37    834  AGGGCCACCCTGACAAGCTCTGCGACCAAGTCTCAGATGCTGTGCTTGATGCCTGCCTCG  893

SEQ ID NO:36    246  CTGAGGACCCTGACAGCAAGGTTGCTTGTGAGACCTGCACCAAGACCAACATGGTCATGG  305
                     | ||||| ||||||||||||| ||||||||||||||||||||| |||| ||||||||||
SEQ ID NO:37    894  CCGAGGACCCTGACAGCAAGGTCGCTTGTGAGACCTGCACCAAGACAAACATGGTCATGG  953

SEQ ID NO:36    306  TCTTTGGTGAGATCACCACCAAGGCCAATGTCGACTACGAGAGATTGTCAGGAGACCT  365
                     |||| |||||||| |||||||||||||||| ||||| |||||| ||||||||||||||
SEQ ID NO:37    954  TCTTTGGTGAGATCACCACCAAGGCCAAGGCTAACGTTGACTATGAGAAGATTGTCAGGGAGACAT  1013

SEQ ID NO:36    366  GCCGCAACATTGGTTTTGTGTCAAACGATGTCGGGCTTGACGCTTGACCACTGCAAGGTGC  425
                     |||  ||||| |||| || ||||||||||| |||||||| || |||| |||||||||||
SEQ ID NO:37    1014 GCCGTAACATCGGTTTTGTGTCAGCTGATGTCGGTCTCGATGCTGACCACTGCAAGGTGC  1073

SEQ ID NO:36    426  TCGTGAACATTGAGCAGCAGTCCCCTGATATTGCTCAGGTGTGCCACTTCACCA  485
                     | ||||||||||||||||||||||||||||||| |||||||||||||||||||
SEQ ID NO:37    1074 TTGTGAACATCGAGCAGCAGTCCCCTGACATTGCACAGGGTGTGCACGGCACTTCACCA  1133

SEQ ID NO:36    486  AGCGCCCCGAGGAGATTGGAGCTGGTGAACCAGGGACACATGTTCGGGTATGCGACCGATG  545
                     |||||||| ||||||||| ||||||||||||||||||||||| ||   || || ||||||
SEQ ID NO:37    1134 AGCGCCCTGAGGAGATTGGTGCTGGTGACCAGGGACACATGTTTGGATATGCAACTGATG  1193

SEQ ID NO:36    546  AGACCCCTGAGTTGATGCCCCTCAGCAGCCATGTCCTTGCCACCAAGCTAGGTGCTGCTCA  605
                     ||||||||||||||||||||||||||||||||||| |||||||||||||| |||||||||
SEQ ID NO:37    1194 AGACCCCTGAGTTGATGCCCCTCAGCAGCCATGTCCCTGCTACCAAGCTTGGCGCTCGTCTTA  1253
```

FIG. 6B

```
SEQ ID NO:36   606  CCGAGGTCCGCAAGAACGGAACCTGCCCCTGGCCTCAGGCCTGATGGGAAGACCCAGTGA   665
                    ||||| ||||||||| ||||| |||||| ||||||| |||||||||||||||||||||||
SEQ ID NO:37  1254  CGGAGGTTCGCAAGAATGGGACCTGCGCATGGCCTCAGGCCTGACGGGAAGACCCAAGTGA  1313

SEQ ID NO:36   666  CAGTCGAGTACCGCAATGAGGGTGGTGCCATGTCCCATCCGTGTCCACACCGTCCTCA    725
                    ||  |||||||||||||||| |||| ||||||| |||| ||||||||||||||||||||
SEQ ID NO:37  1314  CTGTTGAGTACCGCAATGAGAGCGGTGCCAGGGTGCCCAGGGTCCTGTCCACACCGTCCTCA  1373

SEQ ID NO:36   726  TCTCCACCCAGCACGACGAGACAGTGACACAGTGATGAGATCGCTGCTGACCTGAAGGAGC   785
                    |||| ||||||||| ||  |||||||||| | |||||||||||||||||||||||||||||
SEQ ID NO:37  1374  TCTCTACCCAGCATGATGAGAACGATGAGAAGATTGCTGCTGACCTGAAGGAGC  1433

SEQ ID NO:36   786  ATGTCATCAAGCCTATCATCCCTGAGCAGTACCTTGACGAGAAGACCATCTTCCACCTTA   845
                    |||||||||||||| |  || | ||||||||||||||||| ||||||| ||||| ||||
SEQ ID NO:37  1434  ATGTCATCAAGCCTGTCATTCCCGAGCAGTACCTTGATGAGAAGACAATCTTCCATCTTA  1493

SEQ ID NO:36   846  ACCCATCCGGCCGCTTTGTCATTGGTGGACCTCACGGCGATGCTGGCCTCACTGGCCGCA   905
                    |||||||| || || |||| |||||| |||||||||| |||||||||||||||||||
SEQ ID NO:37  1494  ACCCATCTGGTCGCTTCGCTTGTCATTGGCGGACCTCATGGTGATGCTGGTCTCACTGGCCGGA  1553

SEQ ID NO:36   906  AGATCATCATTGACACCTACGGTGGCTGGGAGCCCATGGCCGGTTGGCGCTTTCTCCGGCA   965
                    ||||||||||||||||||| |||||||||||||||| || || ||||| ||||| ||||
SEQ ID NO:37  1554  AGATCATCATTGACACTTATGTGCTGGGAGCTCACGGTGGTTGGCGCTTTCTCTGGCA  1613

SEQ ID NO:36   966  AGGACCCAACCAAGGTTGACCGCAGCCTATGTCGCGGAGCCAGGCTGCCAAGAGCA  1025
                    |||||||||||||||||||||||| ||||| ||||| ||||||||||||||||||
SEQ ID NO:37  1614  AGGACCCAACCAAGGTTGACCGCAGCATACGTCGCAAGGCATACGTCGCAAGGCAAGAGCA  1673

SEQ ID NO:36  1026  TCGTCGCCAGCGGCCTTGCTCGCCGCGCCATCGTCCAGGTGTCCTACGCCATCGGCGTGC  1085
                    |||| || ||||| ||||||||| |||| ||| |||  |||||| ||| ||||||||
SEQ ID NO:37  1674  TTGTTGCTAGTGGCCTTGCTCGCCGCGCCATTGCTCGCCGTGCCATTGTCCAAGTATCATACGCCATCGGTGTCC  1733
```

FIG. 6C

```
SEQ ID NO:36  1086  CCGAGCCTCTCTCCGTGTTTGTCGACACGTACGGCACCGGCGCGATCCCCGACAAGGAGA  1145
                         |||| || |||| ||||| || ||||||| |||||||  |||  |||||||||||||
SEQ ID NO:37  1734  CAGAGCCACTGTCCGTATTCGTCGACACATACGGCACTGGCAGGATCCCTGACAAGGAGA  1793

SEQ ID NO:36  1146  TCCTCAAGATTGTCAAGGAGAACTTCGATTTCAGGCCTGGCATGATTATCATCAACCTTG  1205
                    ||||||||||||| |||||||||||||||| ||||||||||||||||| |||||||||
SEQ ID NO:37  1794  TCCTCAAGATTGTGAAGGAGAACTTCGACTTCAGGCCTGGCATGATCATCAACCTTG  1853

SEQ ID NO:36  1206  ACCTCAAGAAAGGCGGCAACGGCGCTACCTCAAGACGGCCAGCCTACGGCCACTTCGGAA  1265
                    |||||||||| |||||||| ||||||||||||||||||||||||||||| |||| |||
SEQ ID NO:37  1854  ACCTCAAGAAAGGCGGCAACGGCGCTACCTCAAGACGGCCAGCCTTACGCGGTCACTTCGGAA  1913

SEQ ID NO:36  1266  GGGACGACCCTGACTTCACCTGGGAGGTGGTGAAGCCACTCAAGTCGGAGAAACCTTCTG  1325
                    || |||||||| |||||||||||||||||||||||||| ||||||||||||| ||| ||
SEQ ID NO:37  1914  GGGACGACCCAGACTTCACCTGGGAGGTGGTGAAGCCCCTCAAGTGGGAGAAGCCTTCTG  1973

SEQ ID NO:36  1326  CCTAAGGCGGCCTTT  1341
                    |||||  | |  |||
SEQ ID NO:37  1974  CCTAAAAGCTTCCTTT  1989
```

FIG. 7A

```
SEQ ID NO:38    80  GAGACATTCCTATTACCTCAGAGTCAGTGAACGAGGACACCCTGACAAGCTCTGCGAC  139
                    || ||  ||| ||||||| |||||  ||||| || ||||||| ||| |||||||| ||
SEQ ID NO:40   123  GAAACTTTCTTATTCACCTCGAGTCTGTGAACGAGGGTCACCCAGACAAGCTCTGTGAT  182

SEQ ID NO:38   140  CAAATCTCCGATGCTGTCCTCGACGCTTGCCTGAACAGGACCCAGACAGCAAGGTTGCC  199
                    ||  |||||||||||| || ||  ||||||||||||| |||||||||| |||||||||
SEQ ID NO:40   183  CAGATCTCTGATGCAGTTCTTGATGCCTGCCTGAACATCCCGAGAGCAAAGTTGCA    242

SEQ ID NO:38   200  TGCGAAACATGCACCAAGACCAACTTGGTCTCATGGTCTTCGGAGAGATCACCACCAAGGCC  259
                    |  ||||| ||||||||| ||||||||||||||||||| ||  || ||||||||||||||
SEQ ID NO:40   243  TGTGAAACTTGCACCAAGACCAACTTGGTCTCATGGTCTTTGTGAGATCACAACCAAGGCT  302

SEQ ID NO:38   260  AACGTTGACTACGAGAAGATCGTGCGTGACACCTGCAGAACATCGGCTTCGTCTCAAAC    319
                    | ||||||||| ||||||| |||||||| ||| || ||||||  || || |||||||
SEQ ID NO:40   303  ATTGTAGACTATGAGAAGATTGTGCGTGACAACTGCCGTAATATTGGATTTGTTTCTGAT  362

SEQ ID NO:38   320  GATGTGGGAACTTGATGCTGACAACTGCAAGGTCCTTGTAAACATTGAGCAGCAGAGCCCT  379
                    |||||| || |||||||| ||||||||||||||| ||   |||| || ||||||   
SEQ ID NO:40   363  GATGTTGGTCTTGATGCTGACAACTGCAAGGTCCTTGTTTACATTGAGCAGCAAAGTCCT  422

SEQ ID NO:38   380  GATATTGCCCAGGGTGTGCACGGCCACCTTACCAAAAGACCCGAGGAAATCGGTGCTGGA  439
                    |||||||| ||| ||||| |||||| |||||||||| ||||| || |||| |||||||
SEQ ID NO:40   423  GATATTGCTCAAGGTGTCCACGGCCATCTGACCAAAAGCGCCCCGACCGAGATTGGTGCTGGT  482

SEQ ID NO:38   440  GACCAGGGTCACATGTTTGGCTATGCCACGGACGAAACCCCAGAATTGATGCCATTGAGT  499
                    |||||||| |||||||| |||||||| || ||||| |||||||||| || |||| ||||
SEQ ID NO:40   483  GACCAGGGCCACATGTTTGGCTATGCAACAGATGAGACCCCTGAATTAATGCCTCTCAGT  542

SEQ ID NO:38   500  CATGTTCTTGCAACTAAACTCGGTGCTCGTCTCACCGAGGTTCGCAAGAACGGAACCTGC  559
                    ||||||||||||||| ||||||||| |||||| ||||||||||| || |||||||||||
SEQ ID NO:40   543  CACGTGCTTGCAACTAAACTTGGTGCCCGTCTTACAGAAGTCCGCAAGAATGGCACCTGC  602
```

FIG. 7B

```
SEQ ID NO:38   560  CCATGGTTGAGGCCTGATGGGAAAACCCAAGTGACTGTTGAGTATTACAATGACAACGGT  619
                    |  ||||| ||||||||||||||| ||||| ||||| ||||||| ||||| |||||||||
SEQ ID NO:40   603  GCCTGGTTGAGGCCTGATGGCCAAGACCCAAGTTACTGTTGAGTATAGCAATGACAATGGT 662

SEQ ID NO:38   620  GCCATGGTTCCAGTTCGTGTCCACACTGTGCTTATCTCCACCCAACATGATGAGACTGTG  679
                    |||||||||| ||  |||||| |||| |||||||||||| ||||||||| |||||| |
SEQ ID NO:40   663  GCCATGGTTCCAATTAGGGTACACACTGTCTTCTTATCTCCACCCAACACGATGAGACCGTT 722

SEQ ID NO:38   680  ACCAACGACGAAATTGCAGCTGACCTGATGTGACCTCAAGGAGCATGTCAAGCCGGTGATCCCGGAG  739
                    |||||  ||||||  |||||   ||| ||||||||||||||||||||| ||||||| ||||||||
SEQ ID NO:40   723  ACCAATGATGAGATTGCCCGCGACCTTAAGGAGCATGTCATCAAACCAGTCATCCCAGAG 782

SEQ ID NO:38   740  AAGTACCTTGATGAGAAGACCCATTTTCCACTTGAACCCCCTCTGGCCGTTTGTCATTGGA  799
                    |||||||||||||||||| ||| ||||| ||  |||||||   |||||||||| |  |||
SEQ ID NO:40   783  AAGTACCTTGATGAGAATACTATTTTCCACCTTAACCCATCTGGCCGATTCGTTATTGGT 842

SEQ ID NO:38   800  GGTCCTCACGGGTGATGCTGGTCTCCACCGGCCGCAAGATCATCATCGATACTTACGGAGA  859
                    || ||||||||||||||||||||||||||| || ||||||| || || ||||| || ||
SEQ ID NO:40   843  GGACCTCACGGTGATGCTGGTCGTCGTCTGCACTGGTCGTAAAATCATCATCGACACTTATGGTGGT 902

SEQ ID NO:38   860  TGGGGTGCTCATGGTGGTGGTGCTTTCTCCGGAAGGATCCCACCAAGGTTGATAGGAGT  919
                    |||||||||||||||||||||||||||||||| | ||  || || ||||| ||| |||
SEQ ID NO:40   903  TGGGGTGCTCATGGTGGTGGTGCTTTCTCGGGGCAAAGACCCAACCAAGGTCGACAGGAGT 962

SEQ ID NO:38   920  GGTGCTTACATTGTGAGACAGGCTGCTAAGAGCATTGTGGCAAGTGGACTAGCCAGAAGG  979
                    |||||||| ||| ||| || |||||| ||||||||||| ||||||| || ||||| ||
SEQ ID NO:40   963  GGTGCATACATTGTAAGGCAGCTGCAAAGAGTATCGTCGTAGTGGACTTGCTCGTCGTAGA 1022

SEQ ID NO:38   980  TGCATTGTGCAAGTGTCTTATGCCATTGGTGTGCCCGAGCCTTTGTCTCTTGTTGAC  1039
                    |||| ||||||| || |||||||||||||||| |||||||| |||| ||||| |||
SEQ ID NO:40   1023 TGCATCGTGCAGGTATCTTATGCCATTGTGCCTGAGCCTGTGTGCCATTGTCTGTATTCGTTGAC 1082
```

FIG. 7C

```
SEQ ID NO:38  1040  ACCTATGGCACCGGGAAGAGATCCATGATAAGGAGAGATTCTCAACATTGTGAAGGAGAACTTT  1099
                   ||||||||||||||||||||| || ||||| || ||| ||| — || ||||||||||||||
SEQ ID NO:40  1083  ACCTATGGCACTGGGAAAGATCCTGAAAGATCCCTGACACAGGGAAATTTGAAGATCGTTAAGGAGAACTTT  1142

SEQ ID NO:38  1100  GATTTCAGGCCCGGTATGATCTCCATCAACCTTGATCTCAAGAGGGTGGGAATAACAGG  1159
                   || ||||||| || ||||| |||| ||||||| || |||||| — || ||||| ||| —
SEQ ID NO:40  1143  GACTTCAGAGACCTGGAATGATGTCCATTAACTTGGATTTGAAGAGGGTGGCAATAGAAGA  1202

SEQ ID NO:38  1160  TTCTTGAAGACTGCTGCATATGGACACTTCGGCAGAGAGGACCCTGACTTCACATGGGAA  1219
                   ||||||| || ||||| ||| ||| || ||||| |||| — || || ||||||||||||
SEQ ID NO:40  1203  TTCTTGAAAACTGCTGCCTGGTTCACTTGGACGTGATGACCCCGATTCACATGGGAA  1262

SEQ ID NO:38  1220  GTGGTCAAGCCCCTCAAGTGGGAGAAGGCCTAAGCCATTCATTCCACTGCAATGTGCTG  1279
                   ||||||||||||||||||||| || |||| ||||| | — | — —
SEQ ID NO:40  1263  GTTGTCAAGCCCCTCAAGTGGGAAAAGCCCCAAGACTAATAAGTGCTTGCCTATGTTTTT  1322

SEQ ID NO:38  1280  GGAGTTTTTT  1289
                   |   ||| ||
SEQ ID NO:40  1323  GTTCTTTGTT  1332
```

FIG. 8A

| SEQ ID NO:42 | 41  | AGCAGCGCAAGGGCATCGCTAGCACTAAAGAAATGGCAGCCGAGACGTTCCTCTTCACGT | 100 |
| SEQ ID NO:43 | 23  | AACTGCACGAGAGCATCTCTACCACCAAAGAAATGGCGGCCGAGACGTTCCTCTTCACGT | 82 |
| SEQ ID NO:42 | 101 | CCGAGTCTGTGAACGAGGGCCATCCCGACAAGCTCTGTGACCAAGTCTCCGACGCCGTCT | 160 |
| SEQ ID NO:43 | 83  | CCGAGTCCGTGAACGAGAGGGCCATCCCGACAAGCTGTGCGACCAAGTCTCTGACGCCGTCT | 142 |
| SEQ ID NO:42 | 161 | TGGATGCCTGCTTGGCCCAGGATGCCGACAGCAGCAAGGTCGCCTGCGAGACCGTCACCAAGA | 220 |
| SEQ ID NO:43 | 143 | TGGACGCCTGCTTGGCCCAGGATCCTGACAGCAGCAAGGTTGCTTGCGAGACCTGCACCAAGA | 202 |
| SEQ ID NO:42 | 221 | CCAACATGGTCATGGTCTTGGGCGAGATCACCACCAAGGCCACCGTCGACTATGAGAAGA | 280 |
| SEQ ID NO:43 | 203 | CCAACATGTCATGGTCTTCGGCGACATCACCACCAAGGCCACCGTTGACTATGAGAAGA | 262 |
| SEQ ID NO:42 | 281 | TCGTGCGTGACACCTGCCGCAACATCGGTTTCATCTCTGATGACGTTGGTCTCGACGCCG | 340 |
| SEQ ID NO:43 | 263 | TTGTGCGCGACACCTGCCGTGACATCGGCTTCATCTCTGACGACGTCGGTCTCGATGCCG | 322 |
| SEQ ID NO:42 | 341 | ACCGTTGCAARGTGCTCGTCAACATCGAGCAGCAGTCCCCTGACATTGCCCAGGGTGTTC | 400 |
| SEQ ID NO:43 | 323 | ACCATTGCAAGGTGCTCGTCAACATCGAGCAGCAATCCCCTGACATTGCCCAGGGTGTTC | 382 |
| SEQ ID NO:42 | 401 | ATGGACACTTCACCAAGCGTCCCGAAGAAGTCGGCGCCGGTGACCAGGGCATCATGTTCG | 460 |
| SEQ ID NO:43 | 383 | ACGGACACTTCACCAAGCGTCCAGAAGAGGTCGGCGCCGGTGACCAGGGCATCATGTTTG | 442 |

FIG. 8B

```
SEQ ID NO:42   461  GCTATGCCACCGATGAGACCCCTGAGCTGATGCCCCTCAAGCACGTGCTTGCCACCAAGC  520
                    ||||  ||||| ||||||||||||||||||||||||   |||  |||||||||||||||
SEQ ID NO:43   443  GCTACGCCACTGATGAGACCCCTGAGCTGATGCCCCTCACCCACATGCTTGCCACCAAGC  502

SEQ ID NO:42   521  TYGGAGCTCGCCTCACSGAGGTCCGCAAGAATGGCACCTGCGCTGGGTCAGGCCTGACG   580
                    | ||||||||||||| |||||||||||||||||||||||||||||||||||||||||| 
SEQ ID NO:43   503  TCGGAGCTCGCCTCACCGAGGTCCGCAAGAATGGCACCTGCGCTGGGTCAGGCCTGATG   562

SEQ ID NO:42   581  GAAAGACCCAGGTCACAGTCGAGTACCTAAACGAGGATGGTGCCATGGTACCTGTTCGTG  640
                    |||| |||||||||||| |||||||||||||||| ||  ||| || ||||| |||||||
SEQ ID NO:43   563  GAAAGACCCAGGTCACCATTGAGTACCTAAACGAGGGTGCCATGGTGCCCGTTCGTG    622

SEQ ID NO:42   641  TGCACACCGTCCTCATCTCCACCCAGCACGACGAGACCGTCACCAACGACGAGATTGCTG  700
                    |||||||||||||||||||||| |||||||||||||||||||||||||||||||| |||
SEQ ID NO:43   623  TGCACACCGTCCTCATCTCCACCCAGCACATGATGAGACCGTCACCAACGATGAGATCGCTG  682

SEQ ID NO:42   701  CGGACCTCAAGGAGCATGTCATCAAGCCGGTGATCCCCGAAAGTACCTCGATGAGAACA   760
                    | |||||||||||||||||||||||||||| ||||    |||  ||||||||||||||| 
SEQ ID NO:43   683  CAGACCTCAAGGAGCATGTCATCAAGCCGGTGATTCCCGGAAGTACCTCGATGAGAACA   742

SEQ ID NO:42   761  CCATCTTCCACCTGAACCCGTCTGGCCGCTTCGTCATCGGCGGCCCCCACGGTGACGCCG  820
                    |||||||||||| |||||||||  | ||||||||||||||| |||||||||||| ||||
SEQ ID NO:43   743  CCATCTTCCACCTGAACCCGCTTTGTCATCGGTCATCGGCGGCCCTCACGGCGATGCCG  802

SEQ ID NO:42   821  GTCTCACCGGCCGCAAGATCATCGACACCTATGGTGGCTGGGAGCCCACGGCGGCG     880
                    ||||||||| | |||||||||||||||||| |||||||||||||| ||||||| ||
SEQ ID NO:43   803  GTCTCACCGCCCGCAAGATCATCGACACCTATGGTGGGGAGCCCACGGCGGCG       862

SEQ ID NO:42   881  GTGCCTTCTCTGGCAAGGACCCAACCAAGGTCGACCGYAGTGGCGCCTACATTGCCAGGC  940
                    ||||||||||||||||||||||| ||||||||||||| ||||||||||||||||||||||
SEQ ID NO:43   863  GTGCCTTCTCTGGCAAGGACCCTACCAAGGTCGACCGCAGTGGCGCCGCCTACATTGCCAGGC  922
```

FIG. 8C

```
SEQ ID NO:42   941 ARGCCGCCAAGAGCATCATCGCCAGCGGCCTCGCACGCCGCTGCATTGTGCAGATCTCAT 1000
                   | ||  |||||||||||||||||||||| ||||||||| |||||||||||||||||||||
SEQ ID NO:43   923 AGGCTGCCAAGAGCATCATCGCCAGCGGCCTCGCACGCCGCTGCATTGTGCAGATCTCAT 982

SEQ ID NO:42  1001 ACGCCATCGGTGTGCCTGAGCCTTTGTCTGTTCGTCGACTCCTACGGCACCGGCCAAGA 1060
                   | |||||||||||||||| ||||||| ||||||| |||||||||||||||| ||||||||
SEQ ID NO:43   983 ATGCCATCGGTGTACCTGTGCCTTTGTCTGTTCGTCGACTCCTACGGCACTGGCCAAGA 1042

SEQ ID NO:42  1061 TCCCCGACAGGAGAGATCCTCAAGCTCGTGAAGGAGAACTTTGACTTCAGGCCCGGGATGA 1120
                   ||||  ||||| ||||||||||||||||||||||||||||||||||||||| ||||||||
SEQ ID NO:43  1043 TCCCTGACACAGGAGATCCTCAAGCTCGTGAAGGAGAACTTTGACTTCAGACCCGGGATGA 1102

SEQ ID NO:42  1121 TCAGCATCAACCTGGACTTGAAGAAGGTGGAAAACAGGTTCATCAAGACCGCTGCTTACG 1180
                   |||  |||||||||||||||||||||||||||||||||||||||||||||||||| |||||
SEQ ID NO:43  1103 TCACGATCAACCTCGACTTGAAGAAGGTGGAAAACAGGTTCATCAAGACAGCTGCTTACG 1162

SEQ ID NO:42  1181 GTCACTTTGGCCGTGATGATGCCGACTTCACCTGGGAGGTGGTGAAGCCCCTCAAGTTCG 1240
                   |||||||||||| |||||||||| |||||||||||||||||||| ||||||||||||||||
SEQ ID NO:43  1163 GTCACTTTGGCCGCGATGATGATGCTGACTTCACCTGGGAGGTGGTGAAGCCCCCTCAAGTTCG 1222

SEQ ID NO:42  1241 ACAAGGCATCTGCCTAAGAGCATGGCAT 1268
                   |||||||||||||| |||  |||||
SEQ ID NO:43  1223 ACAAGGCATCTGCTTAAGAAGAAGACAT 1250

SEQ ID NO:42  1271 TCTTGGTCTCGCCGCCTCTCAAGTTCGTCAAGACGGGATCATGTTGCTCCTGGGAAGTGGG 1330
                   |||||||||||||||||||||||||||||| ||| ||||||  | || || ||||||| |
SEQ ID NO:43  1266 TCTTGGTCTGATGCCTCTCAAGTTCGGCAAGGCGGGGATCCTTTTGCTCCTCCTCGGAAGTAAG 1325

SEQ ID NO:42  1331 AAGAAGCATTAGACATTG 1348
                   |||||||||||  |  |
SEQ ID NO:43  1326 AAGAAGCATTCAACATCG 1343
```

Figure 9A

```
                       10         20         30         40         50         60
                ----+----|----+----|----+----|----+----|----+----|----+----|
SEQ ID NO 45   MAA-----AASMSFLLSHPQSRSATP------SRHLPLRPAARRVRCATDAAALSPAVT      48
SEQ ID NO 47   MATFTAA--SSLSLLFSHPHSHSRQPSAQGPTASSHLHLHPRASRARCAS---S--DTTA     53
SEQ ID NO 49   MASSSL----FQSLPFSLQTSKPYAPPKPAAHFVV------RAQSPLTQNNN---SS        44
SEQ ID NO 51   MASSSL----FQSLPFSLKTTKPYALPKPAANFVI------RAQSPLTQNTNAASSA        47
SEQ ID NO 53   HEATPAATTSSLSLLFAHPHFHHPSTKQRLDRSHLRLPLRAAAHRTRCATEGAS--ASTA    58
SEQ ID NO 54   MAT-ATA--SSLSLLFAHPHSSNPRPFAGGPHLRRPLRAAPH--RARCASD-A--ATTA      51
SEQ ID NO 55   MAASCMLRSSFISPGLPQLHHQSTSKPNNGIHFFT----------PIKATATND---AISQ    48

70         80         90        100        110        120
                ----+----|----+----|----+----|----+----|----+----|----+----|
SEQ ID NO 45   TKHRRAADENIREEAARHPAPKQG---LSAWYEPFPPAPNGDPN-ERYSLDEIVYRSSSGG   105
SEQ ID NO 47   TKHRRPAEENIREEAARLRGPAQG---FSAWYEPFPPAPGGDPN-ERYSLDEVVYRSSSGG   110
SEQ ID NO 49   SKHRRPADENIRDEARRINAPHDHHLFSAKYVPFNADSSSSSTESYSLDEIVYRSQSGG    104
SEQ ID NO 51   SKHRRPADENIRDEARRINAPHDHHLFSAKYVPFNADPSSST-TESYSLDEIVYRSQSGG    106
SEQ ID NO 53   TKHRRPAEENIREEAARLRGPATT---FSAWYEPFPPASDGDPN-ERYSLDEVVYRSTSGG   115
SEQ ID NO 54   TRHRRPAEENIREEAARLRGPGND---FSAWYVPFPPTPEDDPD-ERYSLDEVVYRSSSGG   108
SEQ ID NO 55   QKHRRPADENIREEARRHCSSHN---FSARYVPFNAGPN---SDEWYSLDEIVYRSRSGG    102
```

Figure 9B

```
                   130       140       150       160       170       180
                 ---+---------+---------+---------+---------+---------+
SEQ ID NO 45     LLDVRHDMEALSRFSGAYWRDLFDSRIGRTTWPYGSGVWSKKEFVLPEIEPD-HIVSLFE    164
SEQ ID NO 47     LLDVRHDMEALARYPGSYWRDLFDSRVGRTAWPYGSGVWSKKEFVLPEIDSD-HIVSLFE    169
SEQ ID NO 49     LLDVQHDMDALKRFDGEYWRNLFDSRVGKTTWPYGSGVWSKKEWVLPEIHDD-DIVSAFE    163
SEQ ID NO 51     LLDVQHDMDALKRFDGEYWRNLFDSRVGKTTWPYGSGVWSKKEWVLPEIHDD-DIVSAFE    165
SEQ ID NO 53     LLDVRHDMDALARFPGSYWRDLFDSRVGRTTWPYGSGVWSKKEFVLPEIDSD-HIVSLFE    174
SEQ ID NO 54     LLDVCHDMEALARFPGSYWRDLFDSRVGRTAWPYGSGVWSKKEFVLPEIDSD-HIVSLFE    167
SEQ ID NO 55     LLDVQHDMDALKKFDGQYWRSLFDSRVGKTTWPYGSGVWSKKEWVLPEIDSD-DIVSAFE    161

190       200       210       220       230       240
                 ---+---------+---------+---------+---------+---------+
SEQ ID NO 45     GNSNLFWAERLGRDHLGGMNDLWVKHCGISHTGSFKDLGMTVLVSQVNRLRRAPLSRPIA    224
SEQ ID NO 47     GNSNLFWAERLGREHLGGMNDLWVKHCGISHTGSFKDLGMTVLVSQVNRLRRAPLSRPIA    229
SEQ ID NO 49     GNSNLFWAERFGKQFLG-MNDLWVKHCGISHTGSFKDLGMTVLVSQVNRLRK--MNRPVV    220
SEQ ID NO 51     GNSNLFWAERFGKQFLG-MNDLWVKHCGISHTGSFKDLGMTVLVSQVNRLRK--MNRPVV    222
SEQ ID NO 53     GNSNLFWAERLGREHLGGMNDLWVKQCGISHTGSFKDLGMTALVSQVNRLRRAPLSRPIN    234
SEQ ID NO 54     GNSNLFWAERLGREHLGGMTDLWVKHCGISHTGSFKDLGMTVLVSQVNRLRRAPLSRPIN    227
SEQ ID NO 55     GNSNLFWAERFGKQFLG-MTDLWVKHCGISHTGSFKDLGMTVLVSQVNRLRK--MHKPVV    218
```

Figure 9C

```
                             250         260         270         280         290         300
                      ----+----|----+----|----+----|----+----|----+----|----+----|
SEQ ID NO 45   GVGCASTGDTSAALSAYCAAAGIPAIVFLPANRISL---EQLIQPIANGATVLSLDTDFD   281
SEQ ID NO 47   GVGCASTGDTSAALSAYCAAAGIPAIVFLPADRISL---QQLIQPIANGATVLSLDTDFD   286
SEQ ID NO 49   GVGCASTGDTSAALSAYCASAAIPSIVFLPANKISL---AQLVQPIANGAFVLSIDTDFD   277
SEQ ID NO 51   GVGCASTGDTSAALSAYCASAAIPSIVFLPANKISL---AQLVQPIANGAFVLSIDTDFD   279
SEQ ID NO 53   GVGCASTGDTSAALSAYCAAAGIPAIVFLPADRISL---QQLIQPIANGATVLSLDTDFD   291
SEQ ID NO 54   GVGCASTGDTSAALSAYCAAAGIPAIVFLPADRISL---QQLIQPIANGATVLSLDTDFD   284
SEQ ID NO 55   GVGCASTGDTSAALSAYCASAGIPSIVFLPANKISM---AQLVQPIANGAFVLSIDTDFD   275

310         320         330         340         350         360
                      ----+----|----+----|----+----|----+----|----+----|----+----|
SEQ ID NO 45   GCMRLIREVTAE------LPIYLANSLNSLRLEGQKTAAIEILQQFDWEVPD--------   327
SEQ ID NO 47   GCMRLIREVTAE------LPIYLANSLNPLRLEGQKTAAIEILQQFDWEVPD--------   332
SEQ ID NO 49   GCMQLIREVTAE------LPIYLANSLNSLKLEGQKTAAIEILQQFNWQVPD--------   323
SEQ ID NO 51   GCMQLIREVTAE------LPIYLANSLNSLRLEGQKTAAIEILQQFDWQVPD--------   325
SEQ ID NO 53   GCMRLIREVTAE------LPIYLANSLNSLRLEGQKTAAIEILQQFDWQVPD--------   337
SEQ ID NO 54   GCMRLIREVTAE------LPIYLANSLNSLRLEGQKTAAIEILQQFNWQVPD--------   330
SEQ ID NO 55   GCMQLIREVTAE------LPIYLANSLNSLRLEGQKTAAIEILQQFDWEVPE--------   321
```

Figure 9D

```
                    370       380       390       400       410       420
                    +---------+---------+---------+---------+---------+
SEQ ID NO 45  WVIVPGGNLGNIYAFYKGFEMCRVLGLVDRVPRLVCAQAANANPLYGYYKTGWTEFQPQV  387
SEQ ID NO 47  WVIVPGGNLGNIYAFYKGFEMCRVLGLVDRVPRLVCAQAANANPLYRYYKSGWTEFEPQT  392
SEQ ID NO 49  WVIVPGSNLGNIYAFYKGFKMFQELGLVDKIPRLVCAQAANADPLYLYFKSGWKEFKPVK  383
SEQ ID NO 51  WVIVPGGNLGNIYAFYKGFKMCQELGLVDKIPRLVCAQAANADPLYLYFKSGWKEFKPVK  385
SEQ ID NO 53  WVIIPGGNLGNIYAFYKGFEMCRALGLVDRVPRLVCAQAANANPLYRYKSGWTDFQSLV   397
SEQ ID NO 54  WVIVPGGNLGNIYAFYKGFEMCRVLGLVDRVPRLVCAQAANANPLYRFYKSGWTDFQPRV  390
SEQ ID NO 55  WVIVPGGNLGNIYAFYKGFQMCKELGLVDRIPRLVCAQAANANPLYLHYKSGWKDFKPVK  381

430       440       450       460       470       480
                    +---------+---------+---------+---------+---------+
SEQ ID NO 45  ARP---------TFASAIQIGDPVSVDRAV-------------------------------  408
SEQ ID NO 47  AET---------TFASAIQIGDPVSVDRAV-------------------------------  413
SEQ ID NO 49  SST---------TFASAIQIGDPVSIDRAV-------------------------------  404
SEQ ID NO 51  SST---------TFASAIQIGDPVSIDRAV-------------------------------  406
SEQ ID NO 53  AGT---------TFASAIQIGDPVSIDRAV-------------------------------  418
SEQ ID NO 54  AET---------TFASAIQIGDPVSVDRAV-------------------------------  411
SEQ ID NO 55  ANT---------TFASAIQIGDPVSIDRAV-------------------------------  402
```

Figure 9E

```
                       490       500       510       520       530       540
                  +----+----+----+----+----+----+----+----+----+----+----+----+
SEQ ID NO 45      ---------VALKATDGIV--------------------EEATEEELMNAMSLADRTGMFAC-  441
SEQ ID NO 47      ---------VALKATDGIV--------------------EEATEEELMDATALADRTGMFAC-  446
SEQ ID NO 49      ---------HALKSCDGIV--------------------EEATEEELMDATAQADSTGMFIC-  437
SEQ ID NO 51      ---------HALKSCDGIV--------------------EEATEEELMDATAQADSTGMFIC-  439
SEQ ID NO 53      ---------VALKATDGIV--------------------EEATEEELMDATALADLTGMFAC-  451
SEQ ID NO 54      ---------VALKATDGIV--------------------EEATEEELMDAMSLADRTGMFAC-  444
SEQ ID NO 55      ---------FALQQCNGIV--------------------EEATEEELMDAMAQADSTGMFIC-  435

550       560       570       580       590       600
                  +----+----+----+----+----+----+----+----+----+----+----+----+
SEQ ID NO 45      PHTGVALAALFKLRDQRVIGTNDRT-VVVSTAHGLKFSQSKIDYHDSKIED------MA  493
SEQ ID NO 47      PHTGVALAALFKLQGQRIIGPNDRT-VVVSTAHGLKFTQSKIDYSKIDKNIKD-----MV  498
SEQ ID NO 49      PHTGVALTALFKLRNSGVIKATDRT-VVVSTAHGLKFTQSKIDYSKDIKD--------MA  489
SEQ ID NO 51      PHTGVALTALFKLRNSGLIKATDRT-VVVSTAHGLKFTQSKIDYHSKDIKD-------MA  491
SEQ ID NO 53      PHTGVALAALFKLRDQGMIGTNDRT-VVVSTAHGLKFTQSKIDYHDKNIKD-------ML  503
SEQ ID NO 54      PHTGVALAALFKLRDQRIIGPNDRT-VVVSTAHGLKFTQSKIDYHDRNIKD-------ML  496
SEQ ID NO 55      PHTGVALTALFKLRNSGVIAPTDRT-VVVSTAHGLKFTQSKIDYHSKEIKD-------ME  487
```

Figure 9F

```
                   610         620         630         640
          ----+----|----+----|----+----|----+----|----+----|----+----
SEQ ID NO 45  CKYS------NPPVSVKADFGAVMDVLKKRL-----KGKL        522
SEQ ID NO 47  CQYA------NPPISVKADFGSVMDVLQKNL-----NGKI        527
SEQ ID NO 49  CRYA------NPPMQVKADFGSVMDVLKTYL-----QSKAH       519
SEQ ID NO 51  CRYA------NPPMQVKADFGSVMDVLKTYL-----QSKTH       521
SEQ ID NO 53  CQYA------NPPISVKPDFGSVMDVLQKKL-----NGKI        532
SEQ ID NO 54  CQYA------NPPINVKADFASVMDVLQNKL-----NGKI        525
SEQ ID NO 55  CRFA------NPPVEVKADFGSVMDVLKSYL---LSQNSKL       519
```

Figure 10A

```
                          10        20        30        40        50        60
                 ----+----+----+----+----+----+----+----+----+----+----+----+
SEQ ID NO 57  MATFTAASSLSLLF-SHPHSHSRQPSAQGPTASSHLHLHPRASRARCAS---------------  48
SEQ ID NO 59  M---AAAASMSFLL-SHPQSRSATP------SRHLPLRPAARRVRCATDAAA-----------  42
SEQ ID NO 61  M---ASSSL-----FQSLPFSLQTSKPYAPPKPAAHFVVRAQSP----LTQN-----------  40
SEQ ID NO 63  M---ASSSL-----FQSLPFSLKTTKPYALPKPAANFVIRAQSP----LTQNTNA--------  43
SEQ ID NO 65  ATPAATTSSLSLLF-AHPHFHHPSTKQRLDRSHLRLPLRAAAHRTRCATEGA-----------  51
SEQ ID NO 54  MAT-ATASSLSLLF-AHPHSSNPRPFAGGPHLRRPLRAAPH--RARCASDAATTATRHRR---  56
SEQ ID NO 55  M---AASCMLRSSFISPGLPQLHHQSTSKPNNGIHFFTPIKAT----ATNDAISQQKHRR---  53

70        80        90       100       110       120
                 ----+----+----+----+----+----+----+----+----+----+----+----+
SEQ ID NO 57  ----------------SAWYEPFPPAPGGDPN-ERYSLDEVVYRSSSGGLLDVRHD         87
SEQ ID NO 59  ----------------LSAWYEPFPPAPNGDPN-ERYSLDEIVYRSSSGGLLDVRHD        82
SEQ ID NO 61  ----------------AKYVPFNADSSSSSTESYSLDEIVYRSQSGGLLDVQHD          79
SEQ ID NO 63  ----------------AKYVPFNADPSSST-TESYSLDEIVYRSQSGGLLDVQHD         81
SEQ ID NO 65  ----------------SAWYEPFPPASDGDPN-ERYSLDEVVYRSTSGGLLDVRHD        90
SEQ ID NO 54  PAEENIREEAARLRGPGNDFSAWYVPFPPTPEDDPD-ERYSLDEVVYRSSSGGLLDVCHD   115
SEQ ID NO 55  PADENIREEARR--HCSSHNFSARYVPFNAGPN--SDEWYSLDEIVYRSRSGGLLDVQHD   109
```

Figure 10B

```
                           130       140       150       160       170       180
                  ----+----+----+----+----+----+----+----+----+----+----+----+
SEQ ID NO 57     MEALARYPGSYWRDLFDSRVGRTAWPYGSGVWSKKEFVLPEIDSDHIVSLFEGNSNLFWA    147
SEQ ID NO 59     MEALSRFSGAYWRDLFDSRIGRTTWPYGSGVWSKKEFVLPEIEPDHIVSLFEGNSNLFWA    142
SEQ ID NO 61     MDALKRFDGEYWRNLFDSRVGKTTWPYGSGVWSKKEWVLPEIHDDDIVSAFEGNSNLFWA    139
SEQ ID NO 63     MDALKRFDGEYWRNLFDSRVGKTTWPYGSGVWSKKEWVLPEIHDDDIVSAFEGNSNLFWA    141
SEQ ID NO 65     MDALARFPGSYWRDLFDSRVGRTTWPYGSGVWSKKEFVLPEIDSDHIVSLFEGNSNLFWA    150
SEQ ID NO 54     MEALARFPGSYWRDLFDSRVGRTAWPYGSGVWSKKEFVLPEIDSDHIVSLFEGNSNLFWA    175
SEQ ID NO 55     MDALKKFDGQYWRSLFDSRVGKTTWPYGSGVWSKKEWVLPEIDSDDIVSAFEGNSNLFWA    169

190       200       210       220       230       240
                  ----+----+----+----+----+----+----+----+----+----+----+----+
SEQ ID NO 57     ERLGREHLGGMNDLWVKHCGISHTGSFKDLGMTVLVSQVNRLRRAPLSRPIAGVGCASTG    207
SEQ ID NO 59     ERLGRDHLGGMNDLWVKHCGISHTGSFKDLGMTVLVSQVNRLRRAPLSRPIAGVGCASTG    202
SEQ ID NO 61     ERFGKQFLG-MNDLWVKHCGISHTGSFKDLGMTVLVSQVNRLRK--MNRPVVGVGCASTG    196
SEQ ID NO 63     ERFGKQFLG-MNDLWVKHCGISHTGSFKDLGMTVLVSQVNRLRK--MNRPVVGVGCASTG    198
SEQ ID NO 65     ERLGREHLGGMNDLWVKQCGISHTGSFKDLGMTALVSQVNRLRRAPLSRPINGVGCASTG    210
SEQ ID NO 54     ERLGREHLGGMTDLWVKHCGISHTGSFKDLGMTVLVSQVNRLRRAPLSRPINGVGCASTG    235
SEQ ID NO 55     ERFGKQFLG-MTDLWVKHCGISHTGSFKDLGMTVLVSQVNRLRK--MHKPVVGVGCASTG    226
```

Figure 10C

```
                      250         260         270         280         290        300
                      ----+----|----+----|----+----|----+----|----+----|----+----|
SEQ ID NO 57  DTSAALSAYCAAAGIPAIVFLPADRISLQQLIQPIANGATVLSLDTDFDGCMRLIREVTA  267
SEQ ID NO 59  DTSAALSAYCAAAGIPAIVFLPANRISLEQLIQPIANGATVLSLDTDFDGCMRLIREVTA  262
SEQ ID NO 61  DTSAALSAYCASAAIPSIVFLPANKISLAQLVQPIANGAFVLSIDTDFDGCMQLIREVTA  256
SEQ ID NO 63  DTSAALSAYCASAAIPSIVFLPANKISLAQLVQPIANGAFVLSIDTDFDGCMQLIREVTA  258
SEQ ID NO 65  DTSAALSAYCAAAGIPAIVFLPADRISLQQLIQPIANGATVLSLDTDFDGCMRLIREVTA  270
SEQ ID NO 54  DTSAALSAYCAAAGIPAIVFLPADRISLQQLIQPIANGATVLSLDTDFDGCMRLIREVTA  295
SEQ ID NO 55  DTSAALSAYCASAGIPSIVFLPANKISMAQLVQPIANGAFVLSIDTDFDGCMQLIREVTA  286

310         320         330         340         350        360
                      ----+----|----+----|----+----|----+----|----+----|----+----|
SEQ ID NO 57  ELPIYLANSLNPLRLEGQKTAAIEILQQFNWQVPDWVIVPGGNLGNIYAFYKGFEMCRVL  327
SEQ ID NO 59  ELPIYLANSLNSLRLEGQKTAAIEILQQFDWEVPDWVIVPGGNLGNIYAFYKGFEMCRVL  322
SEQ ID NO 61  ELPIYLANSLNSLRLEGQKTAAIEILQQFDWQVPDWVIVPGSNLGNIYAFYKGFKMFQEL  316
SEQ ID NO 63  ELPIYLANSLNSLRLEGQKTAAIEILQQFDWQVPDWVIVPGGNLGNIYAFYKGFKMCQEL  318
SEQ ID NO 65  ELPIYLANSLNSLRLEGQKTAAIEILQQFNWQVPDWVIPGGNLGNIYAFYKGFEMCRAL  330
SEQ ID NO 54  ELPIYLANSLNSLRLEGQKTAAIEILQQFDWEVPDWVIVPGGNLGNIYAFYKGFEMCRVL  355
SEQ ID NO 55  ELPIYLANSLNSLRLEGQKTAAIEILQQFDWEVPEWVIVPGGNLGNIYAFYKGFQMCKEL  346
```

Figure 10D

```
                          +----+----+----+----+----+----+----+
                         370       380       390       400       410       420
                          +----+----+----+----+----+----+----+
SEQ ID NO 57  GLVDRVPRLVCAQAANANPLYRYKSGWTEFEPQTAETTFASAIQIGDPVSVDRAVVALK   387
SEQ ID NO 59  GLVDRVPRLVCAQAANANPLYGYYKTGWTEFQPQVARPTFASAIQIGDPVSVDRAVVALK   382
SEQ ID NO 61  GLVDKIPRLVCAQAANADPLYLYFKSGWKEFKPVKSSTTFASAIQIGDPVSIDRAVHALK   376
SEQ ID NO 63  GLVDKIPRLVCAQAANADPLYLYFKSGWKEFKPVKSSTTFASAIQIGDPVSIDRAVHALK   378
SEQ ID NO 65  GLVDRVPRLVCAQAANANPLYRYKSGWTDFQSLVAGTTFASAIQIGDPVSIDRAVVALK   390
SEQ ID NO 54  GLVDRVPRLVCAQAANANPLYRFYKSGWTDFQPRVAETTFASAIQIGDPVSVDRAVVALK   415
SEQ ID NO 55  GLVDRIPRLVCAQAANANPLYLHYKSGWKDFKPVKANTTFASAIQIGDPVSIDRAVFALQ   406

+----+----+----+----+----+----+----+
                         430       440       450       460       470       480
                          +----+----+----+----+----+----+----+
SEQ ID NO 57  ATDGIVEEATEEELMDATALADRTGMFACPHTGVALAALFKLQGQRIIGPNDRTVVVSTA   447
SEQ ID NO 59  ATDGIVEEATEEELMNAMSLADRTGMFACPHTGVALAALFKLRDQRVIGTNDRTVVVSTA   442
SEQ ID NO 61  SCDGIVEEATEEELMDATAQADSTGMFICPHTGVALTALFKLRNSGVIKATDRTVVVSTA   436
SEQ ID NO 63  SCDGIVEEATEEELMDATALADLTGMFACPHTGVALTALFKLRNSGLIKATDRTVVVSTA   438
SEQ ID NO 65  ATDGIVEEATEEELMDATALADLTGMFACPHTGVALAALFKLRDQGMIGTNDRTVVVSTA   450
SEQ ID NO 54  ATDGIVEEATEEELMDAMSLADRTGMFACPHTGVALAALFKLRDQRIIGPNDRTVVVSTA   475
SEQ ID NO 55  QCNGIVEEATEEELMDAMAQADSTGMFICPHTGVALTALFKLRNSGVIAPTDRTVVVSTA   466
```

Figure 10E

```
                                490       500       510       520       530
                       ----+----|----+----|----+----|----+----|----+----|----+----
SEQ ID NO 57  HGLKFTQSKIDYHDKNIKDMVCQYANPPISVKADFGSVMDVLQKNL--NGKI     497
SEQ ID NO 59  HGLKFSQSKIDYHDSKIEDMACKYSNPPVSVKADFGAVMDVLKKRL--KGKL     492
SEQ ID NO 61  HGLKFTQSKIDYHSKDIKDMACRYANPPMQVKADFGSVMDVLKTYL--QSKAH    487
SEQ ID NO 63  HGLKFTQSKIDYHSKDIKDMACRYANPPMQVKADFGSVMDVLKTYL--QSKTH    489
SEQ ID NO 65  HGLKFTQSKIDYHDKNIKDMLCQYANPPISVKPDFGSVMDVLQKKL--NGKI     500
SEQ ID NO 54  HGLKFTQSKIDYHDRNIKDMLCQYANPPINVKADFASVMDVLQNKL--NGKI     525
SEQ ID NO 55  HGLKFTQSKIDYHSKEIKDMECRFANPPVEVKADFGSVMDVLKSYLLSQNSKL    519
```

SEQUENCE LISTING

<160> NUMBER OF SEQ ID NOS: 69

<210> SEQ ID NO 1
<211> LENGTH: 908
<212> TYPE: DNA
<213> ORGANISM: Zea mays

<400> SEQUENCE: 1

```
acgcgggaca gataagtggc atggacgagc cgctggagat ccctgtgctg aacgacctca      60
ccatggttct gggctccata gcgcagtcga gagcaaccgg cgtggtggtc gacttcagcg     120
agccttcagc tgtttacgac aatgtcaagc aggcagcggc gtttggtctg agcagcgtcg     180
```

```
tctacgttcc gaaaatcgag ctagagacag tgactgaact gtcagcgttc tgcgagaagg    240
caagcggctg cttggttgcg ccaacgctgt cgattgggtc cgtgctcctt cagcaagcgg    300
ctatacaggc ctcgttccac tacagcaacg ttgagattgt ggaatcgaga ccaaacccat    360
cggatcttcc atcgcaagat gcaatccaga ttgcaaacaa catatcagac cttggtcaga    420
tatacaacag gaagatatg gattccagca gtccagccag aggccagctg ctcggggaag     480
acggagtgcg cgtgcacagc atggttctcc ctggtctcgt ctccagcacg tcgatcaact    540
tctctggccc aggagagatg tacaccttac ggcatgacgt tgcgaatgtt cagtgcctga    600
tgccaggact gatcctggcg atacggaagg tggtgcggtt caagaacttg atttatgggc    660
tagagaagtt cttgtagtga acaacaaaca accaatgcaa acatcgaca ggcaacaggc     720 aaggcagata tcatctgacg tcgcaacaac caaaacgaca gagatttgga aaataaaggc    780
tgcacagaag acgtctgggg ttttgtgtgc accaggctgc gcagagaacg tctgtcattt    840
tgtgtgcacc actacggcac tacctgctga gcgcgatttt tataaaaaag gcatgggagg    900
gagatcat                                                            908
```

<210> SEQ ID NO 2
<211> LENGTH: 224
<212> TYPE: PRT
<213> ORGANISM: Zea mays

<400> SEQUENCE: 2

```
Ala Gly Gln Ile Ser Gly Met Asp Glu Pro Leu Glu Ile Pro Val Leu
1               5                   10                  15

Asn Asp Leu Thr Met Val Leu Gly Ser Ile Ala Gln Ser Arg Ala Thr
            20                  25                  30

Gly Val Val Val Asp Phe Ser Glu Pro Ser Ala Val Tyr Asp Asn Val
        35                  40                  45

Lys Gln Ala Ala Ala Phe Gly Leu Ser Ser Val Val Tyr Val Pro Lys
    50                  55                  60

Ile Glu Leu Glu Thr Val Thr Glu Leu Ser Ala Phe Cys Glu Lys Ala
65                  70                  75                  80

Ser Gly Cys Leu Val Ala Pro Thr Leu Ser Ile Gly Ser Val Leu Leu
                85                  90                  95

Gln Gln Ala Ala Ile Gln Ala Ser Phe His Tyr Ser Asn Val Glu Ile
            100                 105                 110

Val Glu Ser Arg Pro Asn Pro Ser Asp Leu Pro Ser Gln Asp Ala Ile
        115                 120                 125

Gln Ile Ala Asn Asn Ile Ser Asp Leu Gly Gln Ile Tyr Asn Arg Glu
    130                 135                 140

Asp Met Asp Ser Ser Pro Ala Arg Gly Gln Leu Leu Gly Glu Asp
145                 150                 155                 160

Gly Val Arg Val His Ser Met Val Leu Pro Gly Leu Val Ser Ser Thr
                165                 170                 175

Ser Ile Asn Phe Ser Gly Pro Gly Glu Met Tyr Thr Leu Arg His Asp
            180                 185                 190

Val Ala Asn Val Gln Cys Leu Met Pro Gly Leu Ile Leu Ala Ile Arg
        195                 200                 205

Lys Val Val Arg Phe Lys Asn Leu Ile Tyr Gly Leu Glu Lys Phe Leu
    210                 215                 220
```

<210> SEQ ID NO 3

<211> LENGTH: 339
<212> TYPE: DNA
<213> ORGANISM: Oryza sativa

<400> SEQUENCE: 3

```
aagattggca ggagaaatgc agcaaaggtc ctctgctcaa cgcagatgcc gccatctcag    60
agcacaatca aggttgttat cattggggcg acaaaagaga ttggaagaac ggcaatagcg   120
gcagtaagta aagcaagggg aatggagctt gcagggccca tagattctca gtgtataggc   180
ctagatgcag agagataag tggcatggga agaaccctgg aaattccggt gctcaatgat   240
ctcacaatgg ttctgggctc aattgcacaa accagagcaa ctggagtggt ggttgatttt   300
agtgaacctt caactgttta tgataatgtc aaacaggca                          339
```

<210> SEQ ID NO 4
<211> LENGTH: 113
<212> TYPE: PRT
<213> ORGANISM: Oryza sativa

<400> SEQUENCE: 4

```
Lys Ile Gly Arg Arg Asn Ala Ala Lys Val Leu Cys Ser Thr Gln Met
 1               5                  10                  15
Pro Pro Ser Gln Ser Thr Ile Lys Val Val Ile Gly Ala Thr Lys
             20                  25                  30
Glu Ile Gly Arg Thr Ala Ile Ala Ala Val Ser Lys Ala Arg Gly Met
         35                  40                  45
Glu Leu Ala Gly Ala Ile Asp Ser Gln Cys Ile Gly Leu Asp Ala Gly
     50                  55                  60
Glu Ile Ser Gly Met Gly Arg Thr Leu Glu Ile Pro Val Leu Asn Asp
65                  70                  75                  80
Leu Thr Met Val Leu Gly Ser Ile Ala Gln Thr Arg Ala Thr Gly Val
                 85                  90                  95
Val Val Asp Phe Ser Glu Pro Ser Thr Val Tyr Asp Asn Val Lys Gln
            100                 105                 110
Ala
```

<210> SEQ ID NO 5
<211> LENGTH: 275
<212> TYPE: PRT
<213> ORGANISM: Synechocystus sp

<400> SEQUENCE: 5

```
Met Ala Asn Gln Asp Leu Ile Pro Val Val Asn Gly Ala Ala Gly
 1               5                  10                  15
Lys Met Gly Arg Glu Val Ile Lys Ala Val Ala Gln Ala Pro Asp Leu
             20                  25                  30
Gln Leu Val Gly Ala Val Asp His Asn Pro Ser Leu Gln Gly Gln Asp
         35                  40                  45
Ile Gly Glu Val Val Gly Ile Ala Pro Leu Glu Val Pro Val Leu Ala
     50                  55                  60
Asp Leu Gln Ser Val Leu Val Leu Ala Thr Gln Glu Lys Ile Gln Gly
65                  70                  75                  80
Val Met Val Asp Phe Thr His Pro Ser Gly Val Tyr Asp Asn Val Arg
                 85                  90                  95
Ser Ala Ile Ala Tyr Gly Val Arg Pro Val Val Gly Thr Thr Gly Leu
            100                 105                 110
Ser Glu Gln Gln Ile Gln Asp Leu Gly Asp Phe Ala Glu Lys Ala Ser
```

```
                115              120              125
Thr Gly Cys Leu Ile Ala Pro Asn Phe Ala Ile Gly Val Leu Leu Met
        130                 135                 140
Gln Gln Ala Ala Val Gln Ala Cys Gln Tyr Phe Asp His Val Glu Ile
145                 150                 155                 160
Ile Glu Leu His His Asn Gln Lys Ala Asp Ala Pro Ser Gly Thr Ala
                165                 170                 175
Ile Lys Thr Ala Gln Met Leu Ala Glu Met Gly Lys Thr Phe Asn Pro
                180                 185                 190
Pro Ala Val Glu Glu Lys Glu Thr Ile Ala Gly Ala Lys Gly Gly Leu
                195                 200                 205
Gly Pro Gly Gln Ile Pro Ile His Ser Ile Arg Leu Pro Gly Leu Ile
        210                 215                 220
Ala His Gln Glu Val Leu Phe Gly Ser Pro Gly Gln Leu Tyr Thr Ile
225                 230                 235                 240
Arg His Asp Thr Thr Asp Arg Ala Cys Tyr Met Pro Gly Val Leu Leu
                245                 250                 255
Gly Ile Arg Lys Val Val Glu Leu Lys Gly Leu Val Tyr Gly Leu Glu
                260                 265                 270
Lys Leu Leu
        275

<210> SEQ ID NO 6
<211> LENGTH: 1012
<212> TYPE: DNA
<213> ORGANISM: Zea mays

<400> SEQUENCE: 6
tattgccaga gatgtgtggt aatggagtcc gttgcttcgc tcggtttata gccgagattg      60
aaaatctgca ggggacaaat agattcacta ttcatactgg tgctggaaag atcgttcctg     120
aaatacaaag tgatgggcag gtaaaggttg atatgggcga gcctatcctt tctggactag     180
acatccccac aaaactgcta gctaccaaga acaaagctgt tgttcaagct gaattggcag     240
ttgagggctt aacatggcat gtcacatgtg ttagcatggg aaaccctcac tgtgtcacat     300
ttggtgcaaa tgagttaaag gtattgcagg tcgacgattt aaaacttagc gaaattgggc     360
ctaaatttga gcatcatgaa atgtttcctg ctcgcacaaa cacagaattc gtacaggttt     420
tgtctcgctc acacctcaaa atgcgggtct gggaacgtgg tgctggagca actcttgcct     480
gtggtactgg tgcttgtgca gtggttgttg cagctgttct tgagggtcga gctgagcgga     540
aatgtgtagt tgatttgcct ggcgggccat tggaaattga gtggagggag atgacaatc      600 atgtttacat gactggtcct gcagaggtcg tcttttatgg atctgttgtt cactaggtac     660
tggggaccaa gatagaaggg ttggctgcca ctcagagctt gtgagattgg ttatagtatc     720
catgaaacag agtgttctgg taccagtaca cttgttcaga tattcttaat tatgattgct     780
tgatttgggt agcmgtagag gcttcctttt gaagcattct agtgttcmcc ttttgtactc     840
ctttagtttg tcaggtttga acactacatg ggtaacatg cyttcccacc attttcygtt      900
tcttttcttt gtaagtgaac gccaatgcag tttagtatt gttttctata gatttgtctt      960
gatgcactgg gcttactact tatttctgg tatgaatgct gcctatttcc tg             1012

<210> SEQ ID NO 7
<211> LENGTH: 217
<212> TYPE: PRT
<213> ORGANISM: Zea mays
```

<400> SEQUENCE: 7

Leu Pro Glu Met Cys Gly Asn Gly Val Arg Cys Phe Ala Arg Phe Ile
1               5                   10                  15
Ala Glu Ile Glu Asn Leu Gln Gly Thr Asn Arg Phe Thr Ile His Thr
            20                  25                  30
Gly Ala Gly Lys Ile Val Pro Glu Ile Gln Ser Asp Gly Gln Val Lys
        35                  40                  45
Val Asp Met Gly Glu Pro Ile Leu Ser Gly Leu Asp Ile Pro Thr Lys
    50                  55                  60
Leu Leu Ala Thr Lys Asn Lys Ala Val Val Gln Ala Glu Leu Ala Val
65                  70                  75                  80
Glu Gly Leu Thr Trp His Val Thr Cys Val Ser Met Gly Asn Pro His
                85                  90                  95
Cys Val Thr Phe Gly Ala Asn Glu Leu Lys Val Leu Gln Val Asp Asp
            100                 105                 110
Leu Lys Leu Ser Glu Ile Gly Pro Lys Phe Glu His His Glu Met Phe
        115                 120                 125
Pro Ala Arg Thr Asn Thr Glu Phe Val Gln Val Leu Ser Arg Ser His
    130                 135                 140
Leu Lys Met Arg Val Trp Glu Arg Gly Ala Gly Ala Thr Leu Ala Cys
145                 150                 155                 160
Gly Thr Gly Ala Cys Ala Val Val Ala Ala Val Leu Glu Gly Arg
                165                 170                 175
Ala Glu Arg Lys Cys Val Val Asp Leu Pro Gly Gly Pro Leu Glu Ile
            180                 185                 190
Glu Trp Arg Glu Asp Asp Asn His Val Tyr Met Thr Gly Pro Ala Glu
        195                 200                 205
Val Val Phe Tyr Gly Ser Val Val His
    210                 215

<210> SEQ ID NO 8
<211> LENGTH: 481
<212> TYPE: DNA
<213> ORGANISM: Oryza sativa

<400> SEQUENCE: 8
tgtatccggc gccgacggtg tgatcttcgt catgccgggg gtcaatggcg cggactacac      60
catgaggatc ttcaactcgg acggcagtga gccggagatg tgtggcaatg gagtccgttg     120
ctttgcccgg tttatagctg agcttgaaaa cctacaggga acacatagct tcaaaattca     180
cactggcgct gggctaatca ttcctgaaat acaaaatgat ggcaaggtaa aggttgatat     240
gggccagccc attctctctg gaccagatat tccaacaaaa ctgccatcca ccaagaatga     300
agccgttgtc caagctgatt tgggcagttg atggctcaac atggcaagta acctgtgtta     360
gcatgggcaa tccacattgt gtcacatttg cacaaagga gctcaaggtt ttgcatgttg     420
atgattaaag cttaatgata ttggggccta aattcagcat catgaaatgt tcctgcccca     480
c                                                                    481

<210> SEQ ID NO 9
<211> LENGTH: 85
<212> TYPE: PRT
<213> ORGANISM: Oryza sativa

<400> SEQUENCE: 9

```
Val Ser Gly Ala Asp Gly Val Ile Phe Val Met Pro Gly Val Asn Gly
1               5                   10                  15

Ala Asp Tyr Thr Met Arg Ile Phe Asn Ser Asp Gly Ser Glu Pro Glu
            20                  25                  30

Met Cys Gly Asn Gly Val Arg Cys Phe Ala Arg Phe Ile Ala Glu Leu
            35                  40                  45

Glu Asn Leu Gln Gly Thr His Ser Phe Lys Ile His Thr Gly Ala Gly
            50                  55                  60

Leu Ile Ile Pro Glu Ile Gln Asn Asp Gly Lys Val Lys Val Asp Met
65              70                  75                  80

Gly Gln Pro Ile Leu
                85

<210> SEQ ID NO 10
<211> LENGTH: 1301
<212> TYPE: DNA
<213> ORGANISM: Glycine max

<400> SEQUENCE: 10
atcccttatt aagcaggggt ttcgcggcgc gagacggtga cactggcaga gtggaatttc      60
cgccgccatt cgaagctaca gcgatggcca taaccgccac catttccgtt cccctcacat     120
cccccagtcg ccgcactctc acctccgtca atagcctctc tccccttcct acccgatcca     180
ctttgcccac accgcaacgc actttcaaat accctaattc gcgcctcgtc gtgtcttcca     240
tgagcaccga aacagccgtc aaaacttcat ccgcctcctt cctcaaccgc aaggagtccg     300
gcttcctcca tttcgccaag taccacggcc tcggaaacga cttcgttttg attgacaata     360
gagactcctc cgagcccaag atcagtgctg agaaagcggt gcaactgtgt gatcggaact     420
tcggcgttgg agctgacgga gttatctttg tcttgcctgg catcagtggc accgattata     480
ccatgaggat tttaactctc gatggtagtg agcctgagat gtgtggcaat ggagttcgat     540
gctttgccaa atttgtttct cagcttgaga atttacatgg gaggcatagt tttaccattc     600
atactggtgc tggtctgatt attcctgaag tcttggagga tggaaatgtc agagttgata     660
tgggggagcc agttcttaaa gccttggatg tgcctactaa attacctgca aataaggata     720
atgctgttgt taaatcacag ctagtttag atggagttat ttggcatgtg acctgtgtta     780
gcatggggaa tccacactgt gtaactttca gtagagaagg aagccagaat ttgcttgttg     840
atgaattgaa gctagcagaa attgggccaa aatttgaaca tcatgaggtg ttccctgcac     900
gaactaacac agagtttgtg caagtattat ctaactctca cttgaaaatg cgtgtttggg     960
agcggggagc aggagcaacc ctagcctgtg gaactggagc ttgtgctact gttgttgcag    1020
cagttcttga gggtcgtgct gggaggaatt gcacggttga tctacctgga gggcctcttc    1080
agattgagtg gagggaggaa gataatcatg tttatatgac aggctcagcc gatgtagttt    1140
attatggttc tttgccccctt tgatatgttg ccccccattg taaacccaat atggaattag    1200
gaattggtga ataatatttg tatgagaggt ggactttctg cttgttccta atattttgcc    1260
acgtctttat aaaaaaaaaa aaaaaaaaaa aaaaaaaaa a                         1301

<210> SEQ ID NO 11
<211> LENGTH: 359
<212> TYPE: PRT
<213> ORGANISM: Glycine max

<400> SEQUENCE: 11

Met Ala Ile Thr Ala Thr Ile Ser Val Pro Leu Thr Ser Pro Ser Arg
```

```
                1               5              10              15

Arg Thr Leu Thr Ser Val Asn Ser Leu Ser Pro Leu Ser Thr Arg Ser
               20                  25                  30

Thr Leu Pro Thr Pro Gln Arg Thr Phe Lys Tyr Pro Asn Ser Arg Leu
               35                  40                  45

Val Val Ser Ser Met Ser Thr Glu Thr Ala Val Lys Thr Ser Ser Ala
               50                  55                  60

Ser Phe Leu Asn Arg Lys Glu Ser Gly Phe Leu His Phe Ala Lys Tyr
 65                  70                  75                  80

His Gly Leu Gly Asn Asp Phe Val Leu Ile Asp Asn Arg Asp Ser Ser
                   85                  90                  95

Glu Pro Lys Ile Ser Ala Glu Lys Ala Val Gln Leu Cys Asp Arg Asn
                  100                 105                 110

Phe Gly Val Gly Ala Asp Gly Val Ile Phe Val Leu Pro Gly Ile Ser
                  115                 120                 125

Gly Thr Asp Tyr Thr Met Arg Ile Phe Asn Ser Asp Gly Ser Glu Pro
    130                 135                 140

Glu Met Cys Gly Asn Gly Val Arg Cys Phe Ala Lys Phe Val Ser Gln
145                 150                 155                 160

Leu Glu Asn Leu His Gly Arg His Ser Phe Thr Ile His Thr Gly Ala
                    165                 170                 175

Gly Leu Ile Ile Pro Glu Val Leu Glu Asp Gly Asn Val Arg Val Asp
                    180                 185                 190

Met Gly Glu Pro Val Leu Lys Ala Leu Asp Val Pro Thr Lys Leu Pro
        195                 200                 205

Ala Asn Lys Asp Asn Ala Val Val Lys Ser Gln Leu Val Val Asp Gly
    210                 215                 220

Val Ile Trp His Val Thr Cys Val Ser Met Gly Asn Pro His Cys Val
225                 230                 235                 240

Thr Phe Ser Arg Glu Gly Ser Gln Asn Leu Leu Val Asp Glu Leu Lys
                    245                 250                 255

Leu Ala Glu Ile Gly Pro Lys Phe Glu His His Glu Val Phe Pro Ala
                    260                 265                 270

Arg Thr Asn Thr Glu Phe Val Gln Val Leu Ser Asn Ser His Leu Lys
        275                 280                 285

Met Arg Val Trp Glu Arg Gly Ala Gly Ala Thr Leu Ala Cys Gly Thr
    290                 295                 300

Gly Ala Cys Ala Thr Val Val Ala Ala Val Leu Glu Gly Arg Ala Gly
305                 310                 315                 320

Arg Asn Cys Thr Val Asp Leu Pro Gly Gly Pro Leu Gln Ile Glu Trp
                    325                 330                 335

Arg Glu Glu Asp Asn His Val Tyr Met Thr Gly Ser Ala Asp Val Val
                    340                 345                 350

Tyr Tyr Gly Ser Leu Pro Leu
        355

<210> SEQ ID NO 12
<211> LENGTH: 602
<212> TYPE: DNA
<213> ORGANISM: Triticum aestiva
<220> FEATURE:
<221> NAME/KEY: unsure
<222> LOCATION: (366)..(366)
<223> OTHER INFORMATION: N = A, C, G or T
<220> FEATURE:
<221> NAME/KEY: unsure
```

```
<222> LOCATION: (370)..(370)
<223> OTHER INFORMATION: N = A, C, G or T
<220> FEATURE:
<221> NAME/KEY: unsure
<222> LOCATION: (415)..(415)
<223> OTHER INFORMATION: N = A, C, G or T
<220> FEATURE:
<221> NAME/KEY: unsure
<222> LOCATION: (436)..(436)
<223> OTHER INFORMATION: N = A, C, G or T
<220> FEATURE:
<221> NAME/KEY: unsure
<222> LOCATION: (464)..(464)
<223> OTHER INFORMATION: N = A, C, G or T
<220> FEATURE:
<221> NAME/KEY: unsure
<222> LOCATION: (466)..(466)
<223> OTHER INFORMATION: N = A, C, G or T
<220> FEATURE:
<221> NAME/KEY: unsure
<222> LOCATION: (472)..(472)
<223> OTHER INFORMATION: N = A, C, G or T
<220> FEATURE:
<221> NAME/KEY: unsure
<222> LOCATION: (479)..(479)
<223> OTHER INFORMATION: N = A, C, G or T
<220> FEATURE:
<221> NAME/KEY: unsure
<222> LOCATION: (482)..(482)
<223> OTHER INFORMATION: N = A, C, G or T
<220> FEATURE:
<221> NAME/KEY: unsure
<222> LOCATION: (506)..(506)
<223> OTHER INFORMATION: N = A, C, G or T
<220> FEATURE:
<221> NAME/KEY: unsure
<222> LOCATION: (513)..(513)
<223> OTHER INFORMATION: N = A, C, G or T
<220> FEATURE:
<221> NAME/KEY: unsure
<222> LOCATION: (536)..(536)
<223> OTHER INFORMATION: N = A, C, G or T
<220> FEATURE:
<221> NAME/KEY: unsure
<222> LOCATION: (558)..(558)
<223> OTHER INFORMATION: N = A, C, G or T
<220> FEATURE:
<221> NAME/KEY: unsure
<222> LOCATION: (563)..(563)
<223> OTHER INFORMATION: N = A, C, G or T
<220> FEATURE:
<221> NAME/KEY: unsure
<222> LOCATION: (586)..(586)
<223> OTHER INFORMATION: N = A, C, G or T
<220> FEATURE:
<221> NAME/KEY: unsure
<222> LOCATION: (592)..(592)
<223> OTHER INFORMATION: N = A, C, G or T

<400> SEQUENCE: 12
ctccaccgcc ccctcctcgg gcggtcgcct cctccgtccg ttctgtggga atccgcgccc      60
ccgccgcgcc gtcgcctcga tggccgtgtc cgctcccaag tcgccagccg ccgcctcgtt     120
cctcgagcgc cgcgagtccg agcgcgcgct ccacttcgtg aagtaccagg gcctcggcaa     180
cgacttcata atggtcgaca cagggattc ggccgtaccg aaggtgacac cggaggaggc      240
ggcgaagcta tgcgaccgaa actttgggta ttgggtgctg atggcgtcat cttcgtcctg     300 ccggggtca acggcgcgga ctacactatg aggatattca actccgatgg cagcaaccgg     360
aatgtntggn atggattcgt tgcttgctcg ctttatacgg agttgaaatc tacanggaaa    420
catacttcaa aacaanaggg ggctggatta atatcctgaa atananacat gnaagttang    480
tnatatgggc aacaatctta tggcanattt canaaaatgc atcacaagat aacttntaaa    540
```

```
acgattgaat taggcaanag aantaccgtt ataggaaccc atgaancttg tnaaattaag    600
gt                                                                  602
```

<210> SEQ ID NO 13
<211> LENGTH: 80
<212> TYPE: PRT
<213> ORGANISM: Triticum aestiva
<220> FEATURE:
<221> NAME/KEY: UNSURE
<222> LOCATION: (42)..(42)
<223> OTHER INFORMATION: Xaa = any amino acid
<220> FEATURE:
<221> NAME/KEY: UNSURE
<222> LOCATION: (75)..(75)
<223> OTHER INFORMATION: Xaa = any amino acid

<400> SEQUENCE: 13

```
Ala Leu His Phe Val Lys Tyr Gln Gly Leu Gly Asn Asp Phe Ile Met
1               5                   10                  15

Val Asp Asn Arg Asp Ser Ala Val Pro Lys Val Thr Pro Glu Glu Ala
            20                  25                  30

Ala Lys Leu Cys Asp Arg Asn Phe Gly Xaa Gly Ala Asp Gly Val Ile
        35                  40                  45

Phe Val Leu Pro Gly Val Asn Gly Ala Asp Tyr Thr Met Arg Ile Phe
    50                  55                  60

Asn Ser Asp Gly Ser Asn Arg Asn Val Trp Xaa Gly Phe Val Ala Cys
65                  70                  75                  80
```

<210> SEQ ID NO 14
<211> LENGTH: 279
<212> TYPE: PRT
<213> ORGANISM: Synechocystus sp

<400> SEQUENCE: 14

```
Met Ala Leu Ser Phe Ser Lys Tyr His Gly Leu Gly Asn Asp Phe Ile
1               5                   10                  15

Leu Val Asp Asn Arg Gln Ser Thr Glu Pro Cys Leu Thr Pro Asp Gln
            20                  25                  30

Ala Gln Gln Leu Cys Asp Arg His Phe Gly Ile Gly Ala Asp Gly Val
        35                  40                  45

Ile Phe Ala Leu Pro Gly Gln Gly Gly Thr Asp Tyr Thr Met Arg Ile
    50                  55                  60

Phe Asn Ser Asp Gly Ser Glu Pro Glu Met Cys Gly Asn Gly Ile Arg
65                  70                  75                  80

Cys Leu Ala Lys Phe Leu Ala Asp Leu Glu Gly Val Glu Glu Lys Thr
                85                  90                  95

Tyr Arg Ile His Thr Leu Ala Gly Val Ile Thr Pro Gln Leu Leu Ala
            100                 105                 110

Asp Gly Gln Val Lys Val Asp Met Gly Glu Pro Gln Leu Leu Ala Glu
        115                 120                 125

Leu Ile Pro Thr Thr Leu Ala Pro Ala Gly Glu Lys Val Val Asp Leu
    130                 135                 140

Pro Leu Ala Val Ala Gly Gln Thr Trp Ala Val Thr Cys Val Ser Met
145                 150                 155                 160

Gly Asn Pro His Cys Leu Thr Phe Val Asp Val Asp Ser Leu Asn
                165                 170                 175

Leu Thr Glu Ile Gly Pro Leu Phe Glu His His Pro Gln Phe Ser Gln
            180                 185                 190
```

```
Arg Thr Asn Thr Glu Phe Ile Gln Val Leu Gly Ser Asp Arg Leu Lys
        195                 200                 205

Met Arg Val Trp Glu Arg Gly Ala Gly Ile Thr Leu Ala Cys Gly Thr
    210                 215                 220

Gly Ala Cys Ala Thr Val Val Ala Ala Val Leu Thr Gly Arg Gly Asp
225                 230                 235                 240

Arg Arg Cys Thr Val Glu Leu Pro Gly Gly Asn Leu Glu Ile Glu Trp
                245                 250                 255

Ser Ala Gln Asp Asn Arg Leu Tyr Met Thr Gly Pro Ala Gln Arg Val
            260                 265                 270

Phe Ser Gly Gln Ala Glu Ile
            275
```

<210> SEQ ID NO 15
<211> LENGTH: 1160
<212> TYPE: DNA
<213> ORGANISM: Zea mays

<400> SEQUENCE: 15

```
gtcggctgcg cgtccacggg agacacctcc gccgcgctct cggcctactg cgcagccgcg      60
ggaatccccg ccatcgtgtt cctgccagcg accgcatct cgctgcagca gctcatccag     120
ccgatcgcca acggcgccac cgtgctctct ctagacactg attttgatgg ctgcatgcgg    180
ctcattcgcg aggtcactgc agagctgcca atctaccttg ccaattcgct caacccgctc    240
cgccttgagg ggcagaagac agcggccatc gagatattgc agcagttcaa ttggcaggtg    300
ccagattggg tcattgttcc aggaggcaat cttgggaata tctatgcatt ctacaagggg    360
tttgagatgt gccgcgttct tggacttgtt gatcgcgtgc cacggcttgt ctgcgcacag    420
gctgcaaatg caaatccatt gtaccggtac tacaagtcag gttggactga gtttgagcca    480
caaactgccg agactacatt tgcatctgcg atacagattg gtgatcctgt atctgttgac    540
cgtgcggtgg tcgcgctgaa ggccactgac ggtattgtgg aggaggctac agaggaggag    600
ctaatggatg caacggcgct tgctgaccgc actgggatgt tgcttgcccc acatactggg    660
gttgcacttg ctgctttgtt taagcttcag ggtcagcgta taattggccc taatgaccgc    720
actgtggttg ttagcacagc tcatgggctg aagttcacgc agtcaaagat tgactaccat    780
gacaaaaaca tcaaagacat ggtttgccag tatgctaatc caccgatcag tgtgaaggct    840
gactttggtt ctgtgatgga tgttctccag aaaaatctca atggtaagat ataaagttat    900
atgattaatt aaccctccaa actgtttttt tttgtttttt cgttccagga attttattcc    960
tgagtctttc aactttgttt ggtgaacatg gtatggtgct aaaatctaga cctaatacct   1020
tgtagtacta gttctggagg ctcttttggt tgtaggtcga agtggataga gctgttcctt   1080
gtactttatc tgtttcatgt aatatgaata ataaattatg gtctaaatat ttgaataaaa   1140
aatcgtttgg aatgacccac                                              1160
```

<210> SEQ ID NO 16
<211> LENGTH: 297
<212> TYPE: PRT
<213> ORGANISM: Zea mays

<400> SEQUENCE: 16

```
Val Gly Cys Ala Ser Thr Gly Asp Thr Ser Ala Ala Leu Ser Ala Tyr
1               5                  10                  15

Cys Ala Ala Ala Gly Ile Pro Ala Ile Val Phe Leu Pro Ala Asp Arg
            20                  25                  30
```

-continued

```
Ile Ser Leu Gln Gln Leu Ile Gln Pro Ile Ala Asn Gly Ala Thr Val
            35                  40                  45
Leu Ser Leu Asp Thr Asp Phe Asp Gly Cys Met Arg Leu Ile Arg Glu
 50                  55                  60
Val Thr Ala Glu Leu Pro Ile Tyr Leu Ala Asn Ser Leu Asn Pro Leu
 65                  70                  75                  80
Arg Leu Glu Gly Gln Lys Thr Ala Ala Ile Glu Ile Leu Gln Gln Phe
                 85                  90                  95
Asn Trp Gln Val Pro Asp Trp Val Ile Val Pro Gly Gly Asn Leu Gly
            100                 105                 110
Asn Ile Tyr Ala Phe Tyr Lys Gly Phe Glu Met Cys Arg Val Leu Gly
            115                 120                 125
Leu Val Asp Arg Val Pro Arg Leu Val Cys Ala Gln Ala Ala Asn Ala
        130                 135                 140
Asn Pro Leu Tyr Arg Tyr Tyr Lys Ser Gly Trp Thr Glu Phe Glu Pro
145                 150                 155                 160
Gln Thr Ala Glu Thr Thr Phe Ala Ser Ala Ile Gln Ile Gly Asp Pro
                165                 170                 175
Val Ser Val Asp Arg Ala Val Val Ala Leu Lys Ala Thr Asp Gly Ile
            180                 185                 190
Val Glu Glu Ala Thr Glu Glu Leu Met Asp Ala Thr Ala Leu Ala
            195                 200                 205
Asp Arg Thr Gly Met Phe Ala Cys Pro His Thr Gly Val Ala Leu Ala
        210                 215                 220
Ala Leu Phe Lys Leu Gln Gly Gln Arg Ile Ile Gly Pro Asn Asp Arg
225                 230                 235                 240
Thr Val Val Val Ser Thr Ala His Gly Leu Lys Phe Thr Gln Ser Lys
                245                 250                 255
Ile Asp Tyr His Asp Lys Asn Ile Lys Asp Met Val Cys Gln Tyr Ala
            260                 265                 270
Asn Pro Pro Ile Ser Val Lys Ala Asp Phe Gly Ser Val Met Asp Val
        275                 280                 285
Leu Gln Lys Asn Leu Asn Gly Lys Ile
290                 295
```

<210> SEQ ID NO 17
<211> LENGTH: 325
<212> TYPE: DNA
<213> ORGANISM: Zea mays
<220> FEATURE:
<221> NAME/KEY: unsure
<222> LOCATION: (325)..(325)
<223> OTHER INFORMATION: N = A, C, G or T

<400> SEQUENCE: 17

```
atggcttgca agtactccaa cccgcctgtg agcgtgaagg ctgactttgg cgccgtgatg      60
gatgtgctga agaagaggct caagggcaag ctctgagcgc ctgtgcctgg ctaatgcaat     120
caactgattg gaatgcagtg gtttcgtcgg tatcgggggg tcttttaggc ttcagaaatt     180
ctgtctgggt tagactattt gtttgtggag tttagcagga gaatggctat ctctcctgca     240
agactggcgc tctttcttgt gctacgaatg tgttaccatg gataataagt gtagtcgctg     300
tcggattgaa taatcaaaaa aaaan                                           325
```

<210> SEQ ID NO 18
<211> LENGTH: 31

-continued

```
<212> TYPE: PRT
<213> ORGANISM: Zea mays

<400> SEQUENCE: 18

Met Ala Cys Lys Tyr Ser Asn Pro Pro Val Ser Val Lys Ala Asp Phe
1               5                   10                  15

Gly Ala Val Met Asp Val Leu Lys Lys Arg Leu Lys Gly Lys Leu
            20                  25                  30

<210> SEQ ID NO 19
<211> LENGTH: 528
<212> TYPE: DNA
<213> ORGANISM: Oryza sativa
<220> FEATURE:
<221> NAME/KEY: unsure
<222> LOCATION: (490)..(490)
<223> OTHER INFORMATION: N = A, C, G or T
<220> FEATURE:
<221> NAME/KEY: unsure
<222> LOCATION: (508)..(508)
<223> OTHER INFORMATION: N = A, C, G or T

<400> SEQUENCE: 19
acacccaaca cgcagacttg acagattctg ctactacaaa tcctgcatat ttaacagcgc      60
tgcaactcga cgatggagaa cggtgctgca accaacgggg cgtcggagaa gtcgcactct    120
ccttcacaga cctacctctc cacaagggga gacgattatg gctctcatt cgagaccgtc    180
gtcctcaaag gtcttgcggc tgacgggggt cttttcctgc cgaggaagt gcccgcggca    240
accgagtggc aaagctggaa agacctgccc tacaccgagc ttgccgtcaa ggttctcagc    300
ttgtacatct cccccgccga ggtgccgacg aagacctca gggcgctcgt cgagcgcagc    360
tactcgacct tccgatccaa ggaggttgtg ccgctggtga agctggagga caaccttcac    420
ctgctggagc tattccacgg ccccaactac tcgttcaagg actgcgcgct gcaattcctt    480
ggtaacctcn tcgagtactt ttgactcnca agaacaaggg aaaggagg                528

<210> SEQ ID NO 20
<211> LENGTH: 143
<212> TYPE: PRT
<213> ORGANISM: Oryza sativa
<220> FEATURE:
<221> NAME/KEY: UNSURE
<222> LOCATION: (140)..(140)
<223> OTHER INFORMATION: Xaa = any amino acid

<400> SEQUENCE: 20

Met Glu Asn Gly Ala Ala Thr Asn Gly Ala Ser Glu Lys Ser His Ser
1               5                   10                  15

Pro Ser Gln Thr Tyr Leu Ser Arg Gly Asp Asp Tyr Gly Leu Ser
            20                  25                  30

Phe Glu Thr Val Val Leu Lys Gly Leu Ala Ala Asp Gly Leu Phe
        35                  40                  45

Leu Pro Glu Glu Val Pro Ala Ala Thr Glu Trp Gln Ser Trp Lys Asp
    50                  55                  60

Leu Pro Tyr Thr Glu Leu Ala Val Lys Val Leu Ser Leu Tyr Ile Ser
65                  70                  75                  80

Pro Ala Glu Val Pro Thr Glu Asp Leu Arg Ala Leu Val Glu Arg Ser
                85                  90                  95

Tyr Ser Thr Phe Arg Ser Lys Glu Val Val Pro Leu Val Lys Leu Glu
            100                 105                 110

Asp Asn Leu His Leu Leu Glu Leu Phe His Gly Pro Asn Tyr Ser Phe
```

-continued

```
                115                 120                 125
Lys Asp Cys Ala Leu Gln Phe Leu Gly Asn Leu Xaa Glu Tyr Phe
    130                 135                 140

<210> SEQ ID NO 21
<211> LENGTH: 571
<212> TYPE: DNA
<213> ORGANISM: Glycine max
<220> FEATURE:
<221> NAME/KEY: unsure
<222> LOCATION: (369)..(369)
<223> OTHER INFORMATION: N = A, C, G or T
<220> FEATURE:
<221> NAME/KEY: unsure
<222> LOCATION: (468)..(468)
<223> OTHER INFORMATION: N = A, C, G or T
<220> FEATURE:
<221> NAME/KEY: unsure
<222> LOCATION: (496)..(496)
<223> OTHER INFORMATION: N = A, C, G or T
<220> FEATURE:
<221> NAME/KEY: unsure
<222> LOCATION: (557)..(557)
<223> OTHER INFORMATION: N = A, C, G or T
<220> FEATURE:
<221> NAME/KEY: unsure
<222> LOCATION: (562)..(562)
<223> OTHER INFORMATION: N = A, C, G or T
<220> FEATURE:
<221> NAME/KEY: unsure
<222> LOCATION: (571)..(571)
<223> OTHER INFORMATION: N = A, C, G or T

<400> SEQUENCE: 21
ggatgcaatg gtgcaggctg attccactgg aatgttcata tgtccacaca ctggggtggc      60
tctggcggcg cttattaagc tgaggaatcg tggggttatc ggtgccggtg agagggttgt     120
ggtggtgagc actgcacatg gattgaagtt tgcacagagc aagattgatt atcattctgg     180
gctcattcct ggaatgggcc gctatgctaa cccgctggtt tcggttaagg cggattttgg     240
atcggtcatg gatgttctca aggattcttg cacaacaagt cccccgactt taacaagtct     300
tgacgttgcc aagtaagttt tagttcgggg ttttttctga ttaaagatgt ttttaaacat     360
gtttgtgtnc actttcggtc gttattatgg atttgtaaga ttgggcccaa gtattcgagg     420
gtttgatttc aaacaacatg cttctggtga cgcaatgcaa atttcggngc ataacatcat     480
tgtcgaagat ggatcncgac cgatgaaact gtgtggcaag taatgagaag aaaatagggc     540
acttgtacag agatttnaaa gnttaatttc n                                    571

<210> SEQ ID NO 22
<211> LENGTH: 104
<212> TYPE: PRT
<213> ORGANISM: Glycine max

<400> SEQUENCE: 22

Asp Ala Met Val Gln Ala Asp Ser Thr Gly Met Phe Ile Cys Pro His
1               5                   10                  15

Thr Gly Val Ala Leu Ala Ala Leu Ile Lys Leu Arg Asn Arg Gly Val
            20                  25                  30

Ile Gly Ala Gly Glu Arg Val Val Val Ser Thr Ala His Gly Leu
        35                  40                  45

Lys Phe Ala Gln Ser Lys Ile Asp Tyr His Ser Gly Leu Ile Pro Gly
    50                  55                  60

Met Gly Arg Tyr Ala Asn Pro Leu Val Ser Val Lys Ala Asp Phe Gly
65                  70                  75                  80
```

Ser Val Met Asp Val Leu Lys Asp Ser Cys Thr Thr Ser Pro Pro Thr
            85                  90                  95

Leu Thr Ser Leu Asp Val Ala Lys
            100

<210> SEQ ID NO 23
<211> LENGTH: 2191
<212> TYPE: DNA
<213> ORGANISM: Glycine max

<400> SEQUENCE: 23

| | | | | | |
|---|---|---|---|---|---|
| gcttcctctt | ctctgtttca | gtctctccct | ttctctctcc | aaacctctaa | accctacgcg | 60 |
| cctcccaaac | ccgccgccca | cttcgttgtc | cgcgcccaat | cccccctcac | tcagaacaac | 120 |
| aactcctcct | ccaagcatcg | ccgccccgcc | gacgagaaca | tccgcgacga | ggcccgccgc | 180 |
| atcaatgcgc | cccacgacca | ccacctcttc | tcggccaagt | acgtccccttt | caacgccgac | 240 |
| tcctcctcct | cctcctccac | ggagtcctac | tcgctcgacg | agatcgtcta | ccgctcccaa | 300 |
| tccggcggcc | tcctggacgt | ccagcacgac | atggatgccc | tcaagcgttt | cgacggcgag | 360 |
| tactggcgca | acctcttcga | ctcgcgcgtg | ggcaaaacca | cctggcctta | cggctccggc | 420 |
| gtctggagca | aaaagaatg | ggtcctcccc | gagatccacg | acgacgatat | cgtctccgcc | 480 |
| ttcgaggta | actccaacct | cttctgggcc | gagcgtttcg | gcaaacagtt | cctcggcatg | 540 |
| aacgatttgt | gggtcaaaca | ctgcggaatc | agccacacgg | gcagcttcaa | ggatctcggc | 600 |
| atgaccgtcc | tcgtcagcca | ggtcaatcgc | ttgagaaaaa | tgaaccgccc | cgtcgtcggt | 660 |
| gttggttgcg | cctccaccgg | tgacacatcg | gccgctttat | ccgcctattg | cgcttccgct | 720 |
| gccattcctt | ccattgtgtt | tttgcctgct | aataaaatct | ctcttgccca | acttgttcag | 780 |
| cctattgcca | atggagcctt | tgtgttgagt | atcgacactg | attttgatgg | ttgcatgcag | 840 |
| ttgatcagag | aagtcactgc | tgaattgcct | atttatttgg | ctaactctct | caacagtttg | 900 |
| aagttggaag | ggcagaaaac | tgctgctatt | gagattctgc | agcagtttga | ttggcaggtt | 960 |
| cctgattggg | tcattgtgcc | tggaagcaac | cttggcaaca | tttatgcctt | ttacaaaggg | 1020 |
| tttaagatgt | ttcaagagct | tgggcttgtg | gataagattc | caaggcttgt | ttgtgctcag | 1080 |
| gctgccaatg | ctgatccttt | gtatttgtac | tttaaatccg | ggtggaagga | gtttaagcct | 1140 |
| gtgaagtcga | gcactacatt | tgcttctgcc | attcaaattg | gtgatcctgt | tccattgac | 1200 |
| agggcggttc | acgcgctaaa | gagttgcgat | gggattgtgg | aggaggccac | ggaggaggag | 1260 |
| ttgatggatg | ctacagcgca | ggcggattct | actgggatgt | ttatttgccc | ccacaccggg | 1320 |
| gttgctttaa | ctgcattgtt | taagctcagg | aacagcgggg | ttattaaggc | cactgatagg | 1380 |
| actgtggtgg | ttagcactgc | tcatggcttg | aagttcactc | agtccaagat | tgattaccat | 1440 |
| tctaaggaca | tcaaggacat | ggcttgccgc | tatgctaacc | cgcccatgca | agtgaaggca | 1500 |
| gactttggct | cggttatgga | tgttttgaag | acgtatttgc | agagtaaggc | tcattaggtt | 1560 |
| agcattgcaa | gttttgctcc | tcctgagttt | gctcattatt | tacttacttt | taggcactac | 1620 |
| tgctgtattg | tcttttctat | gagctaggtt | tgagtgttgt | aataatttgc | ttgctgcatt | 1680 |
| atgtatgccg | tctagtgttc | catattgggc | atcatcctta | gtatttgttg | tagattttct | 1740 |
| ttgctgagca | tttgatataa | tagctcaagt | aggaaaatga | attgggtact | atgaggaatg | 1800 |
| catatcattg | gcttgttatt | actggattcc | agaccacccc | aaaagaaaat | aattccaaaa | 1860 |
| aatataatta | gaacaaattt | cgtccttgtt | atgctgttgg | cattaagctc | agtgtgggta | 1920 |

-continued

```
ttaccaagca actcgaaatc aagagaaaaa aaaattgaca gcaaaggagc tgcattgttg    1980
gactgagtca catcacttca ttgctatgtc gtcatatttc gttgaattac gggaaggcag    2040
catgcacagc aatatgcagc gattaactga agccacaccg cacacattga agtagtagtc    2100
aatttagaca ctccatcttg tactttctac aaaaatgaat ttttcttagc cattaagtat    2160
aatattttat tctaaaaaaa aaaaaaaaaa a                                   2191
```

<210> SEQ ID NO 24
<211> LENGTH: 518
<212> TYPE: PRT
<213> ORGANISM: Glycine max

<400> SEQUENCE: 24

```
Ala Ser Ser Ser Leu Phe Gln Ser Leu Pro Phe Ser Leu Gln Thr Ser
1               5                   10                  15

Lys Pro Tyr Ala Pro Lys Pro Ala Ala His Phe Val Val Arg Ala
            20                  25                  30

Gln Ser Pro Leu Thr Gln Asn Asn Ser Ser Lys His Arg Arg
        35                  40                  45

Pro Ala Asp Glu Asn Ile Arg Asp Glu Ala Arg Arg Ile Asn Ala Pro
    50                  55                  60

His Asp His His Leu Phe Ser Ala Lys Tyr Val Pro Phe Asn Ala Asp
65                  70                  75                  80

Ser Ser Ser Ser Ser Thr Glu Ser Tyr Ser Leu Asp Glu Ile Val
                85                  90                  95

Tyr Arg Ser Gln Ser Gly Gly Leu Leu Asp Val Gln His Asp Met Asp
                100                 105                 110

Ala Leu Lys Arg Phe Asp Gly Glu Tyr Trp Arg Asn Leu Phe Asp Ser
            115                 120                 125

Arg Val Gly Lys Thr Thr Trp Pro Tyr Gly Ser Gly Val Trp Ser Lys
        130                 135                 140

Lys Glu Trp Val Leu Pro Glu Ile His Asp Asp Ile Val Ser Ala
145                 150                 155                 160

Phe Glu Gly Asn Ser Asn Leu Phe Trp Ala Glu Arg Phe Gly Lys Gln
                165                 170                 175

Phe Leu Gly Met Asn Asp Leu Trp Val Lys His Cys Gly Ile Ser His
                180                 185                 190

Thr Gly Ser Phe Lys Asp Leu Gly Met Thr Val Leu Ser Gln Val
            195                 200                 205

Asn Arg Leu Arg Lys Met Asn Arg Pro Val Val Gly Val Gly Cys Ala
    210                 215                 220

Ser Thr Gly Asp Thr Ser Ala Ala Leu Ser Ala Tyr Cys Ala Ser Ala
225                 230                 235                 240

Ala Ile Pro Ser Ile Val Phe Leu Pro Ala Asn Lys Ile Ser Leu Ala
                245                 250                 255

Gln Leu Val Gln Pro Ile Ala Asn Gly Ala Phe Val Leu Ser Ile Asp
            260                 265                 270

Thr Asp Phe Asp Gly Cys Met Gln Leu Ile Arg Glu Val Thr Ala Glu
        275                 280                 285

Leu Pro Ile Tyr Leu Ala Asn Ser Leu Asn Ser Leu Lys Leu Glu Gly
    290                 295                 300

Gln Lys Thr Ala Ala Ile Glu Ile Leu Gln Gln Phe Asp Trp Gln Val
305                 310                 315                 320

Pro Asp Trp Val Ile Val Pro Gly Ser Asn Leu Gly Asn Ile Tyr Ala
```

-continued

```
                        325                 330                 335
Phe Tyr Lys Gly Phe Lys Met Phe Gln Glu Leu Gly Leu Val Asp Lys
            340                 345                 350
Ile Pro Arg Leu Val Cys Ala Gln Ala Ala Asn Ala Asp Pro Leu Tyr
        355                 360                 365
Leu Tyr Phe Lys Ser Gly Trp Lys Glu Phe Lys Pro Val Lys Ser Ser
    370                 375                 380
Thr Thr Phe Ala Ser Ala Ile Gln Ile Gly Asp Pro Val Ser Ile Asp
385                 390                 395                 400
Arg Ala Val His Ala Leu Lys Ser Cys Asp Gly Ile Val Glu Glu Ala
                405                 410                 415
Thr Glu Glu Leu Met Asp Ala Thr Ala Gln Ala Asp Ser Thr Gly
            420                 425                 430
Met Phe Ile Cys Pro His Thr Gly Val Ala Leu Thr Ala Leu Phe Lys
        435                 440                 445
Leu Arg Asn Ser Gly Val Ile Lys Ala Thr Asp Arg Thr Val Val Val
    450                 455                 460
Ser Thr Ala His Gly Leu Lys Phe Thr Gln Ser Lys Ile Asp Tyr His
465                 470                 475                 480
Ser Lys Asp Ile Lys Asp Met Ala Cys Arg Tyr Ala Asn Pro Pro Met
                485                 490                 495
Gln Val Lys Ala Asp Phe Gly Ser Val Met Asp Val Leu Lys Thr Tyr
            500                 505                 510
Leu Gln Ser Lys Ala His
        515

<210> SEQ ID NO 25
<211> LENGTH: 643
<212> TYPE: DNA
<213> ORGANISM: Triticum aestiva
<220> FEATURE:
<221> NAME/KEY: unsure
<222> LOCATION: (177)..(177)
<223> OTHER INFORMATION: N = A, C, G or T
<220> FEATURE:
<221> NAME/KEY: unsure
<222> LOCATION: (258)..(258)
<223> OTHER INFORMATION: N = A, C, G or T
<220> FEATURE:
<221> NAME/KEY: unsure
<222> LOCATION: (274)..(274)
<223> OTHER INFORMATION: N = A, C, G or T
<220> FEATURE:
<221> NAME/KEY: unsure
<222> LOCATION: (286)..(286)
<223> OTHER INFORMATION: N = A, C, G or T
<220> FEATURE:
<221> NAME/KEY: unsure
<222> LOCATION: (293)..(293)
<223> OTHER INFORMATION: N = A, C, G or T
<220> FEATURE:
<221> NAME/KEY: unsure
<222> LOCATION: (305)..(305)
<223> OTHER INFORMATION: N = A, C, G or T
<220> FEATURE:
<221> NAME/KEY: unsure
<222> LOCATION: (307)..(307)
<223> OTHER INFORMATION: N = A, C, G or T
<220> FEATURE:
<221> NAME/KEY: unsure
<222> LOCATION: (311)..(311)
<223> OTHER INFORMATION: N = A, C, G or T
<220> FEATURE:
<221> NAME/KEY: unsure
<222> LOCATION: (378)..(378)
<223> OTHER INFORMATION: N = A, C, G or T
```

```
<220> FEATURE:
<221> NAME/KEY: unsure
<222> LOCATION: (394)..(394)
<223> OTHER INFORMATION: N = A, C, G or T
<220> FEATURE:
<221> NAME/KEY: unsure
<222> LOCATION: (400)..(400)
<223> OTHER INFORMATION: N = A, C, G or T
<220> FEATURE:
<221> NAME/KEY: unsure
<222> LOCATION: (425)..(425)
<223> OTHER INFORMATION: N = A, C, G or T
<220> FEATURE:
<221> NAME/KEY: unsure
<222> LOCATION: (432)..(432)
<223> OTHER INFORMATION: N = A, C, G or T
<220> FEATURE:
<221> NAME/KEY: unsure
<222> LOCATION: (444)..(444)
<223> OTHER INFORMATION: N = A, C, G or T
<220> FEATURE:
<221> NAME/KEY: unsure
<222> LOCATION: (449)..(449)
<223> OTHER INFORMATION: N = A, C, G or T
<220> FEATURE:
<221> NAME/KEY: unsure
<222> LOCATION: (457)..(457)
<223> OTHER INFORMATION: N = A, C, G or T
<220> FEATURE:
<221> NAME/KEY: unsure
<222> LOCATION: (458)..(458)
<223> OTHER INFORMATION: N = A, C, G or T
<220> FEATURE:
<221> NAME/KEY: unsure
<222> LOCATION: (465)..(465)
<223> OTHER INFORMATION: N = A, C, G or T
<220> FEATURE:
<221> NAME/KEY: unsure
<222> LOCATION: (469)..(469)
<223> OTHER INFORMATION: N = A, C, G or T
<220> FEATURE:
<221> NAME/KEY: unsure
<222> LOCATION: (479)..(479)
<223> OTHER INFORMATION: N = A, C, G or T
<220> FEATURE:
<221> NAME/KEY: unsure
<222> LOCATION: (480)..(480)
<223> OTHER INFORMATION: N = A, C, G or T
<220> FEATURE:
<221> NAME/KEY: unsure
<222> LOCATION: (484)..(484)
<223> OTHER INFORMATION: N = A, C, G or T
<220> FEATURE:
<221> NAME/KEY: unsure
<222> LOCATION: (520)..(520)
<223> OTHER INFORMATION: N = A, C, G or T
<220> FEATURE:
<221> NAME/KEY: unsure
<222> LOCATION: (532)..(532)
<223> OTHER INFORMATION: N = A, C, G or T
<220> FEATURE:
<221> NAME/KEY: unsure
<222> LOCATION: (545)..(545)
<223> OTHER INFORMATION: N = A, C, G or T
<220> FEATURE:
<221> NAME/KEY: unsure
<222> LOCATION: (561)..(561)
<223> OTHER INFORMATION: N = A, C, G or T
<220> FEATURE:
<221> NAME/KEY: unsure
<222> LOCATION: (584)..(584)
<223> OTHER INFORMATION: N = A, C, G or T
<220> FEATURE:
<221> NAME/KEY: unsure
<222> LOCATION: (592)..(592)
<223> OTHER INFORMATION: N = A, C, G or T
<220> FEATURE:
<221> NAME/KEY: unsure
<222> LOCATION: (596)..(596)
```

```
<223> OTHER INFORMATION: N = A, C, G or T
<220> FEATURE:
<221> NAME/KEY: unsure
<222> LOCATION: (607)..(607)
<223> OTHER INFORMATION: N = A, C, G or T
<220> FEATURE:
<221> NAME/KEY: unsure
<222> LOCATION: (610)..(610)
<223> OTHER INFORMATION: N = A, C, G or T
<220> FEATURE:
<221> NAME/KEY: unsure
<222> LOCATION: (614)..(614)
<223> OTHER INFORMATION: N = A, C, G or T
<220> FEATURE:
<221> NAME/KEY: unsure
<222> LOCATION: (621)..(621)
<223> OTHER INFORMATION: N = A, C, G or T
<220> FEATURE:
<221> NAME/KEY: unsure
<222> LOCATION: (633)..(633)
<223> OTHER INFORMATION: N = A, C, G or T
<220> FEATURE:
<221> NAME/KEY: unsure
<222> LOCATION: (638)..(638)
<223> OTHER INFORMATION: N = A, C, G or T
<220> FEATURE:
<221> NAME/KEY: unsure
<222> LOCATION: (641)..(641)
<223> OTHER INFORMATION: N = A, C, G or T

<400> SEQUENCE: 25
gctcatccag cccatcgcca acggcgccac ggtgctctcg cttgacacgg atttcgacgg      60
atgcatgcgg cttatcaggg aggtgacagc tgagctgccc atatacctcg caaactcact     120
caactcgctt ccggctggag gggcagaaga ctgcagccat ccgagatatt gcaacantca     180
attggcaggt gcccggactg ggtcacatcc caaggaggca atctggggga acattttatg     240
ctttcctaca aggatttnaa tttccgtgtc cttngctagt tgattncctt ccnactcctt     300
gttantncaa naggccgcca acgcaaaccc actgtacccg tactacaatc ctggggtgac     360
tgatttccat ccacttgntt gccgggacaa tttncatccn gcaacaattt ggggattcca     420
tatcnattac cntcggtttt ttcnccctna aaggacnnat gattntccna ggaactccnn     480
aggnggatca aggatccaaa ggctttctac tcactggaan ttgcttccca anacggggtt     540
cactnccgcc cgttaaaccc ntgacaagta taatggacaa cacnccgggg tntatnacaa     600
cggcaanttn aaancaagtt natcattaga acnggaantt ncc                       643

<210> SEQ ID NO 26
<211> LENGTH: 84
<212> TYPE: PRT
<213> ORGANISM: Triticum aestiva
<220> FEATURE:
<221> NAME/KEY: UNSURE
<222> LOCATION: (44)..(44)
<223> OTHER INFORMATION: Xaa = any amino acid
<220> FEATURE:
<221> NAME/KEY: UNSURE
<222> LOCATION: (59)..(59)
<223> OTHER INFORMATION: Xaa = any amino acid
<220> FEATURE:
<221> NAME/KEY: UNSURE
<222> LOCATION: (75)..(75)
<223> OTHER INFORMATION: Xaa = any amino acid

<400> SEQUENCE: 26

Leu Ile Gln Pro Ile Ala Asn Gly Ala Thr Val Leu Ser Leu Asp Thr
1               5                   10                  15

Asp Phe Asp Gly Cys Met Arg Leu Ile Arg Glu Val Thr Ala Glu Leu
            20                  25                  30
```

```
Pro Ile Tyr Leu Ala Asn Ser Leu Asn Ser Leu Xaa Leu Glu Gly Gln
        35                  40                  45

Lys Thr Ala Ala Ile Arg Asp Ile Ala Thr Xaa Asn Trp Gln Val Pro
 50                  55                  60

Gly Leu Gly His Ile Pro Arg Arg Gln Ser Xaa Thr Phe Tyr Ala Phe
 65                  70                  75                  80

Leu Gln Gly Phe

<210> SEQ ID NO 27
<211> LENGTH: 525
<212> TYPE: PRT
<213> ORGANISM: Arabidopsis thaliana

<400> SEQUENCE: 27

Leu Ser Ser Cys Leu Phe Asn Ala Ser Val Ser Ser Leu Asn Pro Lys
 1               5                  10                  15

Gln Asp Pro Ile Arg Arg His Arg Ser Thr Ser Leu Leu Arg His Arg
                20                  25                  30

Pro Val Val Ile Ser Cys Thr Ala Asp Gly Asn Asn Ile Lys Ala Pro
        35                  40                  45

Ile Glu Thr Ala Val Lys Pro Pro His Arg Thr Glu Asp Asn Ile Arg
 50                  55                  60

Asp Glu Ala Arg Arg Asn Arg Ser Asn Ala Val Asn Pro Phe Ser Ala
 65                  70                  75                  80

Lys Tyr Val Pro Phe Asn Ala Ala Pro Gly Ser Thr Glu Ser Tyr Ser
                85                  90                  95

Leu Asp Glu Ile Val Tyr Arg Ser Arg Ser Gly Gly Leu Leu Asp Val
               100                 105                 110

Glu His Asp Met Glu Ala Leu Lys Arg Phe Asp Gly Ala Tyr Trp Arg
               115                 120                 125

Asp Leu Phe Asp Ser Arg Val Gly Lys Ser Thr Trp Pro Tyr Gly Ser
           130                 135                 140

Gly Val Trp Ser Lys Lys Glu Trp Val Leu Pro Glu Ile Asp Asp Asp
145                 150                 155                 160

Asp Ile Val Ser Ala Phe Glu Gly Asn Ser Asn Leu Phe Trp Ala Glu
               165                 170                 175

Arg Phe Gly Lys Gln Phe Leu Gly Met Asn Asp Leu Trp Val Lys His
           180                 185                 190

Cys Gly Ile Ser His Thr Gly Ser Phe Lys Asp Leu Gly Met Thr Val
           195                 200                 205

Leu Val Ser Gln Val Asn Arg Leu Arg Lys Met Lys Arg Pro Val Val
       210                 215                 220

Gly Val Gly Cys Ala Ser Thr Gly Asp Thr Ser Ala Ala Leu Ser Ala
225                 230                 235                 240

Tyr Cys Ala Ser Ala Gly Ile Pro Ser Ile Val Phe Leu Pro Ala Asn
                245                 250                 255

Lys Ile Ser Met Ala Gln Leu Val Gln Pro Ile Ala Asn Gly Ala Phe
           260                 265                 270

Val Leu Ser Ile Asp Thr Asp Phe Asp Gly Cys Met Lys Leu Ile Arg
       275                 280                 285

Glu Ile Thr Ala Glu Leu Pro Ile Tyr Leu Ala Asn Ser Leu Asn Ser
   290                 295                 300

Leu Arg Leu Glu Gly Gln Lys Thr Ala Ala Ile Glu Ile Leu Gln Gln
305                 310                 315                 320
```

```
Phe Asp Trp Gln Val Pro Asp Trp Val Ile Val Pro Gly Gly Asn Leu
            325                 330                 335
Gly Asn Ile Tyr Ala Phe Tyr Lys Gly Phe Lys Met Cys Gln Glu Leu
            340                 345                 350
Gly Leu Val Asp Arg Ile Pro Arg Met Val Cys Ala Gln Ala Ala Asn
            355                 360                 365
Ala Asn Pro Leu Tyr Leu His Tyr Lys Ser Gly Trp Lys Asp Phe Lys
            370                 375                 380
Pro Met Thr Ala Ser Thr Thr Phe Ala Ser Ala Ile Gln Ile Gly Asp
385                 390                 395                 400
Pro Val Ser Ile Asp Arg Ala Val Tyr Ala Leu Lys Lys Cys Asn Gly
            405                 410                 415
Ile Val Glu Glu Ala Thr Glu Glu Leu Met Asp Ala Met Ala Gln
            420                 425                 430
Ala Asp Ser Thr Gly Met Phe Ile Cys Pro His Thr Gly Val Ala Leu
            435                 440                 445
Thr Ala Leu Phe Lys Leu Arg Asn Gln Gly Val Ile Ala Pro Thr Asp
            450                 455                 460
Arg Thr Val Val Ser Thr Ala His Gly Leu Lys Phe Thr Gln Ser
465                 470                 475                 480
Lys Ile Asp Tyr His Ser Asn Ala Ile Pro Asp Met Ala Cys Arg Phe
            485                 490                 495
Ser Asn Pro Pro Val Asp Val Lys Ala Asp Phe Gly Ala Val Met Asp
            500                 505                 510
Val Leu Lys Ser Tyr Leu Gly Ser Asn Thr Leu Thr Ser
            515                 520                 525

<210> SEQ ID NO 28
<211> LENGTH: 1478
<212> TYPE: DNA
<213> ORGANISM: Zea mays

<400> SEQUENCE: 28
caacagtggt ccttgagggg gactcatatg atgaagctca gtcatatgca aaattgcgtt      60
gccagcagga aggccgcaca tttgtacctc cttttgacca tcctgatgtc atcactggac     120
aaggaactat cggcatggaa attgttaggc agctgcaagg tccactgcat gcaatatttg     180
tacctgttgg aagtggtgga ttaattgctg gaattgctgc ctatgtaaaa cgggttcgcc     240
cagaggtgaa ataattgga gtggaaccct cagatgcaaa tgcaatggca ttatccttgt     300
gtcatggtaa gagggtcatg ttggagcatg ttggtgggtt tgctgatggt gtagctgtca     360
aagctgttgg ggaagaaaca tttcgcctgt gcagagagct agtagatggc attgttatgg     420
tcagtcgaga tgctatttgt gcttcaataa aggatatgtt tgaggagaaa agaagtatcc     480
ttgaacctgc tggtgcccct tgcattggctg ggctgaagc ctactgcaaa tactataact     540
tgaaaggaga aactgtggtt gcaataacta gtggggcaaa tatgaacttt gatcgactta     600
gactagtaac cgagctagct gatgttggcc gaaaacggga agcagtgtta gctacatttc     660
tgccagagcg gcagggaagc ttcaaaaaat tcacagaatt ggttggcagg atgaatatta     720
ctgaattcaa atacagatac gattctaatg caaaagatgc ccttgttctt tacagtgttg     780
gcatctacac tgacaatgag cttggagcaa tgatggatcg catggaatct gcgaaactga     840
ggactgttaa cctactgac aatgatttgg caaaggacca ccttagatac tttattggag     900
gaagatcaga aataaaagat gaactggttt accggttcat tttcccggaa aggcctgggg     960
```

-continued

```
cccttatgaa attttggac acgtttagtc ctcgttggaa catcagcctt ttccattacc    1020
gtgcacaggg tgaagctgga gcaaatgtat tagttggtat acaagtgccg ccagcagaat    1080
ttgatgaatt caagagtcat gccaacaatc ttgggtacga gtacatgtca gagcacaaca    1140
atgagatata ccggttgctg ttgcgtgacc caaaggtcta atgtatatgc ctttgctccc    1200
ataataagtt ggtgacactt tcaaggaag attttgctcc aaggtagaag ttgcgagttt    1260
cttcaagttg aaatgaagcc atcaccaaat gtagcttcgg tgtgccatct gtttactcag    1320
ttagatcatg tagtgtatca gttgtgtatc tttgttgttg tgcttcgtga tctcaattta    1380
ttgctttgtg cacctagagg ttgtcaaata atgataaccg atatgttatc taaatatcta    1440
ataatgatta tgtgattgtg attaaaaagg gggggccc                           1478
```

<210> SEQ ID NO 29
<211> LENGTH: 392
<212> TYPE: PRT
<213> ORGANISM: Zea mays

<400> SEQUENCE: 29

```
Thr Val Val Leu Glu Gly Asp Ser Tyr Asp Glu Ala Gln Ser Tyr Ala
1               5                   10                  15

Lys Leu Arg Cys Gln Gln Glu Gly Arg Thr Phe Val Pro Pro Phe Asp
            20                  25                  30

His Pro Asp Val Ile Thr Gly Gln Gly Thr Ile Gly Met Glu Ile Val
        35                  40                  45

Arg Gln Leu Gln Gly Pro Leu His Ala Ile Phe Val Pro Val Gly Gly
    50                  55                  60

Gly Gly Leu Ile Ala Gly Ile Ala Ala Tyr Val Lys Arg Val Arg Pro
65                  70                  75                  80

Glu Val Lys Ile Ile Gly Val Glu Pro Ser Asp Ala Asn Ala Met Ala
                85                  90                  95

Leu Ser Leu Cys His Gly Lys Arg Val Met Leu Glu His Val Gly Gly
            100                 105                 110

Phe Ala Asp Gly Val Ala Val Lys Ala Val Gly Glu Glu Thr Phe Arg
        115                 120                 125

Leu Cys Arg Glu Leu Val Asp Gly Ile Val Met Val Ser Arg Asp Ala
    130                 135                 140

Ile Cys Ala Ser Ile Lys Asp Met Phe Glu Glu Lys Arg Ser Ile Leu
145                 150                 155                 160

Glu Pro Ala Gly Ala Leu Ala Leu Ala Gly Ala Glu Ala Tyr Cys Lys
                165                 170                 175

Tyr Tyr Asn Leu Lys Gly Glu Thr Val Val Ala Ile Thr Ser Gly Ala
            180                 185                 190

Asn Met Asn Phe Asp Arg Leu Arg Leu Val Thr Glu Leu Ala Asp Val
        195                 200                 205

Gly Arg Lys Arg Glu Ala Val Leu Ala Thr Phe Leu Pro Glu Arg Gln
    210                 215                 220

Gly Ser Phe Lys Lys Phe Thr Glu Leu Val Gly Arg Met Asn Ile Thr
225                 230                 235                 240

Glu Phe Lys Tyr Arg Tyr Asp Ser Asn Ala Lys Asp Ala Leu Val Leu
                245                 250                 255

Tyr Ser Val Gly Ile Tyr Thr Asp Asn Glu Leu Gly Ala Met Met Asp
            260                 265                 270

Arg Met Glu Ser Ala Lys Leu Arg Thr Val Asn Leu Thr Asp Asn Asp
```

-continued

```
                    275                 280                 285
Leu Ala Lys Asp His Leu Arg Tyr Phe Ile Gly Gly Arg Ser Glu Ile
        290                 295                 300

Lys Asp Glu Leu Val Tyr Arg Phe Ile Phe Pro Glu Arg Pro Gly Ala
305                 310                 315                 320

Leu Met Lys Phe Leu Asp Thr Phe Ser Pro Arg Trp Asn Ile Ser Leu
                325                 330                 335

Phe His Tyr Arg Ala Gln Gly Glu Ala Gly Ala Asn Val Leu Val Gly
            340                 345                 350

Ile Gln Val Pro Pro Ala Glu Phe Asp Glu Phe Lys Ser His Ala Asn
        355                 360                 365

Asn Leu Gly Tyr Glu Tyr Met Ser Glu His Asn Asn Glu Ile Tyr Arg
    370                 375                 380

Leu Leu Leu Arg Asp Pro Lys Val
385                 390

<210> SEQ ID NO 30
<211> LENGTH: 728
<212> TYPE: DNA
<213> ORGANISM: Glycine max
<220> FEATURE:
<221> NAME/KEY: unsure
<222> LOCATION: (501)..(501)
<223> OTHER INFORMATION: N = A, C, G or T
<220> FEATURE:
<221> NAME/KEY: unsure
<222> LOCATION: (569)..(569)
<223> OTHER INFORMATION: N = A, C, G or T
<220> FEATURE:
<221> NAME/KEY: unsure
<222> LOCATION: (581)..(581)
<223> OTHER INFORMATION: N = A, C, G or T
<220> FEATURE:
<221> NAME/KEY: unsure
<222> LOCATION: (594)..(594)
<223> OTHER INFORMATION: N = A, C, G or T
<220> FEATURE:
<221> NAME/KEY: unsure
<222> LOCATION: (603)..(603)
<223> OTHER INFORMATION: N = A, C, G or T
<220> FEATURE:
<221> NAME/KEY: unsure
<222> LOCATION: (622)..(622)
<223> OTHER INFORMATION: N = A, C, G or T
<220> FEATURE:
<221> NAME/KEY: unsure
<222> LOCATION: (631)..(631)
<223> OTHER INFORMATION: N = A, C, G or T
<220> FEATURE:
<221> NAME/KEY: unsure
<222> LOCATION: (634)..(634)
<223> OTHER INFORMATION: N = A, C, G or T
<220> FEATURE:
<221> NAME/KEY: unsure
<222> LOCATION: (639)..(639)
<223> OTHER INFORMATION: N = A, C, G or T
<220> FEATURE:
<221> NAME/KEY: unsure
<222> LOCATION: (659)..(659)
<223> OTHER INFORMATION: N = A, C, G or T
<220> FEATURE:
<221> NAME/KEY: unsure
<222> LOCATION: (668)..(668)
<223> OTHER INFORMATION: N = A, C, G or T
<220> FEATURE:
<221> NAME/KEY: unsure
<222> LOCATION: (670)..(670)
<223> OTHER INFORMATION: N = A, C, G or T
<220> FEATURE:
<221> NAME/KEY: unsure
<222> LOCATION: (697)..(697)
```

<223> OTHER INFORMATION: N = A, C, G or T
<220> FEATURE:
<221> NAME/KEY: unsure
<222> LOCATION: (699)..(699)
<223> OTHER INFORMATION: N = A, C, G or T
<220> FEATURE:
<221> NAME/KEY: unsure
<222> LOCATION: (707)..(707)
<223> OTHER INFORMATION: N = A, C, G or T
<220> FEATURE:
<221> NAME/KEY: unsure
<222> LOCATION: (726)..(726)
<223> OTHER INFORMATION: N = A, C, G or T
<220> FEATURE:
<221> NAME/KEY: unsure
<222> LOCATION: (727)..(727)
<223> OTHER INFORMATION: N = A, C, G or T

<400> SEQUENCE: 30

```
aaaatattgt agcaataacc agtggagcaa acatgaattt tgataaactt cgggttgtaa     60
ctgaacttgc taatgttggt cgtaaacaag aggctgtgct ggcaactgtt atggcagagg    120
agcctggcag tttcaaacaa ttttgtgaat tggtggggca agatgaacata acagaattca   180
aatacagata taactcaaat gagaaggcag ttgtccttta cagtgttggg gttcacacaa    240
tctccgaact aagagcaatg caggagagga tggaatcttc tcagctcaaa acttacaatc    300
tcacagaaag tgacttggtg aaagaccact tgcgttactt gatgggaggc cgatcaaacg    360
ttcagaatga ggtctttgtc gtctcacctt ccaagaaag  actggtgctt tgatgaaatt    420
tttggaccct tcagtccacg ttgggatatt agtttatcca ttaccgaggg gaggtgaaac    480
tggagcaaac tgctagttgg ntacaggtac caaaatgaga tagatgagtc catgatcgtg    540
ctaacaaact ggatatgatt ataagtggna atatgtgatg nctcagctca atcncgatgg    600
ggnttaagca ctgcatatgg gnattagggg nagntacant taaattcacg gcctcaagnt    660
aagcatantn taggaactag ctttacaggg ggctacnant taaccgngta ttttttttga    720
gatganng                                                              728
```

<210> SEQ ID NO 31
<211> LENGTH: 152
<212> TYPE: PRT
<213> ORGANISM: Glycine max
<220> FEATURE:
<221> NAME/KEY: UNSURE
<222> LOCATION: (130)..(130)
<223> OTHER INFORMATION: Xaa = any amino acid
<220> FEATURE:
<221> NAME/KEY: UNSURE
<222> LOCATION: (143)..(143)
<223> OTHER INFORMATION: Xaa = any amino acid

<400> SEQUENCE: 31

```
Asn Ile Val Ala Ile Thr Ser Gly Ala Asn Met Asn Phe Asp Lys Leu
1               5                   10                  15

Arg Val Val Thr Glu Leu Ala Asn Val Gly Arg Lys Gln Glu Ala Val
                20                  25                  30

Leu Ala Thr Val Met Ala Glu Glu Pro Gly Ser Phe Lys Gln Phe Cys
            35                  40                  45

Glu Leu Val Gly Gln Met Asn Ile Thr Glu Phe Lys Tyr Arg Tyr Asn
        50                  55                  60

Ser Asn Glu Lys Ala Val Val Leu Tyr Ser Val Gly Val His Thr Ile
65                  70                  75                  80

Ser Glu Leu Arg Ala Met Gln Glu Arg Met Glu Ser Ser Gln Leu Lys
                85                  90                  95
```

-continued

Thr Tyr Asn Leu Thr Glu Ser Asp Leu Val Lys Asp His Leu Arg Tyr
            100                 105                 110

Leu Met Gly Gly Arg Ser Asn Val Gln Asn Glu Val Phe Val Val Ser
        115                 120                 125

Pro Xaa Pro Arg Lys Thr Gly Ala Leu Met Lys Phe Leu Asp Xaa Phe
    130                 135                 140

Ser Pro Arg Trp Asp Ile Ser Leu
145                 150

<210> SEQ ID NO 32
<211> LENGTH: 572
<212> TYPE: DNA
<213> ORGANISM: Glycine max

<400> SEQUENCE: 32
aaagacctgg tgctttgatg aaattttggg accccttcag tccacgttgg aatatcagtt      60
tattccatta ccgaggggag ggtgaaactg gagcaaatgt gctagttgga atacaggtac     120
ccaaaagtga gatggatgag ttccacgatc gtgccaacaa acttggatat gattataaag     180
tggtgaataa tgatgatgac ttccagcttc taatgcactg atgatggttt taggcacttg     240
ccattattgt gtattttagt caacaagttt gccatattta atatttccac ggtcgtttct     300
aaaagttgga tggggaaaaa aggtggaaag gaagtggcct tcagacatgt cattagttga     360
ttagaggaac aactagttct ttttacctaa tgcggcgtct tattcatttt tttataatct     420
gtaatttatg tttttttgtt gttgttaaca ttggaatctt ataatgttgt tgcctggtct     480
tttgtgtctg taatataagt gtcttcaaaa ggttgtttgc taaatttcag cagcctaaaa     540
aaaaaaaaaa aaaaaaaaaa aaaaaaaaaa aa                                   572

<210> SEQ ID NO 33
<211> LENGTH: 72
<212> TYPE: PRT
<213> ORGANISM: Glycine max

<400> SEQUENCE: 33

Arg Pro Gly Ala Leu Met Lys Phe Leu Asp Pro Phe Ser Pro Arg Trp
1               5                   10                  15

Asn Ile Ser Leu Phe His Tyr Arg Gly Glu Gly Glu Thr Gly Ala Asn
            20                  25                  30

Val Leu Val Gly Ile Gln Val Pro Lys Ser Glu Met Asp Glu Phe His
        35                  40                  45

Asp Arg Ala Asn Lys Leu Gly Tyr Asp Tyr Lys Val Val Asn Asn Asp
    50                  55                  60

Asp Asp Phe Gln Leu Leu Met His
65                  70

<210> SEQ ID NO 34
<211> LENGTH: 507
<212> TYPE: PRT
<213> ORGANISM: Burkholderia capacia

<400> SEQUENCE: 34

Met Ala Ser His Asp Tyr Leu Lys Lys Ile Leu Thr Ala Arg Val Tyr
1               5                   10                  15

Asp Val Ala Phe Glu Thr Glu Leu Glu Pro Ala Arg Asn Leu Ser Ala
            20                  25                  30

Arg Leu Arg Asn Pro Val Tyr Leu Lys Arg Glu Asp Asn Gln Pro Val

-continued

```
                35                  40                  45
Phe Ser Phe Lys Leu Arg Gly Ala Tyr Asn Lys Met Ala His Ile Pro
 50                  55                  60
Ala Asp Ala Leu Ala Arg Gly Val Ile Thr Ala Ser Ala Gly Asn His
 65                  70                  75                  80
Ala Gln Gly Val Ala Phe Ser Ala Ala Arg Met Gly Val Lys Ala Val
                 85                  90                  95
Ile Val Val Pro Val Thr Thr Pro Gln Val Lys Val Asp Ala Val Arg
                100                 105                 110
Ala His Gly Gly Pro Gly Val Glu Val Ile Gln Ala Gly Glu Ser Tyr
                115                 120                 125
Ser Asp Ala Tyr Ala His Ala Leu Lys Val Gln Glu Glu Arg Gly Leu
130                 135                 140
Thr Phe Val His Pro Phe Asp Asp Pro Tyr Val Ile Ala Gly Gln Gly
145                 150                 155                 160
Thr Ile Ala Met Glu Ile Leu Arg Gln His Gln Gly Pro Ile His Ala
                165                 170                 175
Ile Phe Val Pro Ile Gly Gly Gly Gly Leu Ala Ala Gly Val Ala Ala
                180                 185                 190
Tyr Val Lys Ala Val Arg Pro Glu Ile Lys Val Ile Gly Val Gln Ala
                195                 200                 205
Glu Asp Ser Cys Ala Met Ala Gln Ser Leu Gln Ala Gly Lys Arg Val
                210                 215                 220
Glu Leu Ala Glu Val Gly Leu Phe Ala Asp Gly Thr Ala Val Lys Leu
225                 230                 235                 240
Val Gly Glu Glu Thr Phe Arg Leu Cys Lys Glu Tyr Leu Asp Gly Val
                245                 250                 255
Val Thr Val Asp Thr Asp Ala Leu Cys Ala Ala Ile Lys Asp Val Phe
                260                 265                 270
Gln Asp Thr Arg Ser Val Leu Glu Pro Ser Gly Ala Leu Ala Val Ala
                275                 280                 285
Gly Ala Lys Leu Tyr Ala Glu Arg Glu Gly Ile Glu Asn Gln Thr Leu
290                 295                 300
Val Ala Val Thr Ser Gly Ala Asn Met Asn Phe Asp Arg Met Arg Phe
305                 310                 315                 320
Val Ala Glu Arg Ala Glu Val Gly Glu Ala Arg Glu Ala Val Phe Ala
                325                 330                 335
Val Thr Ile Pro Glu Glu Arg Gly Ser Phe Lys Arg Phe Cys Ser Leu
                340                 345                 350
Val Gly Asp Arg Asn Val Thr Glu Phe Asn Tyr Arg Ile Ala Asp Ala
                355                 360                 365
Gln Ser Ala His Ile Phe Val Gly Val Gln Ile Arg Arg Arg Gly Glu
                370                 375                 380
Ser Ala Asp Ile Ala Ala Asn Phe Glu Ser His Gly Phe Lys Thr Ala
385                 390                 395                 400
Asp Leu Thr His Asp Glu Leu Ser Lys Glu His Ile Arg Tyr Met Val
                405                 410                 415
Gly Gly Arg Ser Pro Leu Ala Leu Asp Glu Arg Leu Phe Arg Phe Glu
                420                 425                 430
Phe Pro Glu Arg Pro Gly Ala Leu Met Lys Phe Leu Ser Ser Met Ala
                435                 440                 445
Pro Asp Trp Asn Ile Ser Leu Phe His Tyr Arg Asn Gln Gly Ala Asp
                450                 455                 460
```

Tyr Ser Ser Ile Leu Val Gly Leu Gln Val Pro Gln Ala Asp His Ala
465                 470                 475                 480

Glu Phe Glu Arg Phe Leu Ala Ala Leu Gly Tyr Pro Tyr Val Glu Glu
                485                 490                 495

Ser Ala Asn Pro Ala Tyr Arg Leu Phe Leu Ser
                500                 505

<210> SEQ ID NO 35
<211> LENGTH: 1582
<212> TYPE: DNA
<213> ORGANISM: Zea mays

<400> SEQUENCE: 35

| | | |
|---|---|---|
| acgagacgag tcccctcccc ccacctcgcc tcacccaacc ggaacgaaca agttaccatc | 60 |
| tcatcccaac cccgcctcga ccggatctcg tcggactcgg atccgcccga ccaccccgcg | 120 |
| ccgccgcaga tcaaagaaga tggcagctct cgacaccttc ctcttcacct cggagtctgt | 180 |
| gaacgaggga caccctgaca agctctgcga ccaggtctca gatgccgttc ttgacgcttg | 240 |
| ccttgctgag gaccctgaca gcaaggttgc ttgtgagacc tgcaccaaga ccaacatggt | 300 |
| catggtcttt ggtgagatca ccaccaaggc caatgtcgac tacgagaaga ttgtcaggga | 360 |
| gacctgccgc aacattggtt ttgtgtcaaa cgatgtcggg cttgacgctg accactgcaa | 420 |
| ggtgctcgtg aacattgagc agcagtcccc tgatattgct cagggtgtgc atggccactt | 480 |
| caccaagcgc cccgaggaga ttggagctgg tgaccaggga cacatgttcg ggtatgcgac | 540 |
| cgatgagacc cctgagttga tgcccctcag ccatgtcctt gccaccaagc taggtgctcg | 600 |
| tctcaccgag gtccgcaaga acggaacctg cccctggctc aggcctgatg ggaagaccca | 660 |
| ggtgacagtc gagtaccgca atgagggtgg tgccatggtc cccatccgtg tccacaccgt | 720 |
| cctcatctcc acccagcacg acgagacagt gaccaatgat gagatcgctg ctgacctgaa | 780 |
| ggagcatgtc atcaagccta tcatccctga gcagtacctt gacgagaaga ccatcttcca | 840 |
| ccttaaccca tccggccgct tgtcattgg tggacctcac ggcgatgctg gcctcactgg | 900 |
| ccgcaagatc atcattgaca cctacggtgg ctggggagcc catggcggtg cgctttctc | 960 |
| cggcaaggac ccaaccaagg ttgaccgcag cggagcctat gtcgcgaggc aggctgccaa | 1020 |
| gagcatcgtc gccagcggcc ttgctcgccg cgccatcgtc caggtgtcct acgccatcgg | 1080 |
| cgtgcccgag cctctctccg tgtttgtcga cacgtacggc accggcgcga tccccgacaa | 1140 |
| ggagatcctc aagattgtca aggagaactt cgatttcagg cctggcatga ttatcatcaa | 1200 |
| ccttgacctc aagaaaggcg gcaacgggcg ctacctcaag acggcagcct acggccactt | 1260 |
| cggaagggac gaccctgact tcacctggga ggtggtgaag ccactcaagt cggagaaacc | 1320 |
| ttctgcctaa gcggcctttt ttttcagtaa gaagcttttg gtggtctgct gtgcttaatc | 1380 |
| atgcttttat atggcttcta catgttgtgg ttctttcttg atctgcaccg cgcttatcgt | 1440 |
| ttgtgttgta ctgccctaat aagtggtgct tatgaggact gtttctggtt tgctgcttta | 1500 |
| tgttgtaatg ctttgaaaca atgaaagaag ctacaggcca cagctatttt gagaagtaat | 1560 |
| ggaacctcgt gccgttttga tt | 1582 |

<210> SEQ ID NO 36
<211> LENGTH: 396
<212> TYPE: PRT
<213> ORGANISM: Zea mays

<400> SEQUENCE: 36

```
Met Ala Ala Leu Asp Thr Phe Leu Phe Thr Ser Glu Ser Val Asn Glu
1               5                   10                  15

Gly His Pro Asp Lys Leu Cys Asp Gln Val Ser Asp Ala Val Leu Asp
            20                  25                  30

Ala Cys Leu Ala Glu Asp Pro Asp Ser Lys Val Ala Cys Glu Thr Cys
        35                  40                  45

Thr Lys Thr Asn Met Val Met Val Phe Gly Glu Ile Thr Thr Lys Ala
50                  55                  60

Asn Val Asp Tyr Glu Lys Ile Val Arg Glu Thr Cys Arg Asn Ile Gly
65                  70                  75                  80

Phe Val Ser Asn Asp Val Gly Leu Asp Ala Asp His Cys Lys Val Leu
                85                  90                  95

Val Asn Ile Glu Gln Gln Ser Pro Asp Ile Ala Gln Gly Val His Gly
            100                 105                 110

His Phe Thr Lys Arg Pro Glu Glu Ile Gly Ala Gly Asp Gln Gly His
        115                 120                 125

Met Phe Gly Tyr Ala Thr Asp Glu Thr Pro Glu Leu Met Pro Leu Ser
130                 135                 140

His Val Leu Ala Thr Lys Leu Gly Ala Arg Leu Thr Glu Val Arg Lys
145                 150                 155                 160

Asn Gly Thr Cys Pro Trp Leu Arg Pro Asp Gly Lys Thr Gln Val Thr
                165                 170                 175

Val Glu Tyr Arg Asn Glu Gly Gly Ala Met Val Pro Ile Arg Val His
            180                 185                 190

Thr Val Leu Ile Ser Thr Gln His Asp Glu Thr Val Thr Asn Asp Glu
        195                 200                 205

Ile Ala Ala Asp Leu Lys Glu His Val Ile Lys Pro Ile Ile Pro Glu
210                 215                 220

Gln Tyr Leu Asp Glu Lys Thr Ile Phe His Leu Asn Pro Ser Gly Arg
225                 230                 235                 240

Phe Val Ile Gly Gly Pro His Gly Asp Ala Gly Leu Thr Gly Arg Lys
                245                 250                 255

Ile Ile Ile Asp Thr Tyr Gly Gly Trp Gly Ala His Gly Gly Gly Ala
            260                 265                 270

Phe Ser Gly Lys Asp Pro Thr Lys Val Asp Arg Ser Gly Ala Tyr Val
        275                 280                 285

Ala Arg Gln Ala Ala Lys Ser Ile Val Ala Ser Gly Leu Ala Arg Arg
290                 295                 300

Ala Ile Val Gln Val Ser Tyr Ala Ile Gly Val Pro Glu Pro Leu Ser
305                 310                 315                 320

Val Phe Val Asp Thr Tyr Gly Thr Gly Ala Ile Pro Asp Lys Glu Ile
                325                 330                 335

Leu Lys Ile Val Lys Glu Asn Phe Asp Phe Arg Pro Gly Met Ile Ile
            340                 345                 350

Ile Asn Leu Asp Leu Lys Lys Gly Gly Asn Gly Arg Tyr Leu Lys Thr
        355                 360                 365

Ala Ala Tyr Gly His Phe Gly Arg Asp Asp Pro Asp Phe Thr Trp Glu
370                 375                 380

Val Val Lys Pro Leu Lys Ser Glu Lys Pro Ser Ala
385                 390                 395

<210> SEQ ID NO 37
<211> LENGTH: 2183
```

<212> TYPE: DNA
<213> ORGANISM: Oryza sativa

<400> SEQUENCE: 37

```
gaattcttat aaatgaacgg aaaatggaaa aaaaaattga ttggtgccac ttcaaagtta      60
aatatgccaa gacgaattga tatgtttctg ctgttgtttt atgctcttga ttagttgatg     120
cgcatgttca atgatttatg atgtttgtct ttgtggaaag attacatgta aagagtatag     180
tagaacccct aaaagctagc cagcgatttc gctctttttt tccaggtctc catgatatgt     240
ttaccccyaa aagtggtata tttatgtgat agttacaata catagtggac cacgattgat     300
tatgcgttta tgctgattcc ggcagaaaat tgttagattc cttgtgctct atacctgctt     360
gttgcgcttg tagagaatat tacaaatacc taacacttgc ccaaggaact taggaactta     420
gtcaactctt tgtagggaca actattttag cccaaaattg tggtcttgtc aggtgccaac     480
aaaacagcat cttggcgtac ataagctata tagaggatta aaaggaatgt tttgttcctt     540
gctactgttt ttttaacctg tttactcagg acaaattttg ttgcataaac catttgttct     600
agggatcagt attgtcctct cagtgtgtta tgtaagcatt tccagaaatc aattgtcgct     660
atcagcttcc ctcacattag ctatcactta taccccttttt tttctcatag gctcaccatg     720
tccattttat tcatgatatt tctttgtcta aagtatgtga ataccatttt tatgcagata     780
ggagaagatg gccgcacttg atacctttcct ctttacctcg gagtctgtga acgagggcca     840
ccctgacaag ctctgcgacc aagtctcaga tgctgtgctt gatgcctgcc tcgccgagga     900
ccctgacagc aaggtcgctt gtgagacctg caccaagaca acatggtca tggtctttgg     960
tgagatcacc accaaggcta acgttgacta tgagaagatt gtcagggaga catgccgtaa    1020
catcggtttt gtgtcagctg atgtcggtct cgatgctgac cactgcaagg tgcttgtgaa    1080
catcgagcag cagtcccctg acattgcaca gggtgtgcac gggcacttca ccaagcgccc    1140
tgaggagatt ggtgctggtg accagggaca catgtttgga tatgcaactg atgagacccc    1200
tgagttgatg cccctcagcc atgtccttgc taccaagctt ggcgctcgtc ttacggaggt    1260
tcgcaagaat gggacctgcg catggctcag gcctgacggg aagacccaag tgactgttga    1320
gtaccgcaat gagagcggtg ccagggtccc tgtccgtgtc cacaccgtcc tcatctctac    1380
ccagcatgat gagacagtca ccaacgatga gattgctgct gacctgaagg agcatgtcat    1440
caagcctgtc attcccgagc agtaccttga tgagaagaca atcttccatc ttaacccatc    1500
tggtcgcttc gtcattggcg gacctcatgg tgatgctggg ctcactggcc ggaagatcat    1560
cattgacact tatggtggct ggggagctca cggtggtggt gccttctctg caaggaccc     1620
aaccaaggtt gaccgcagtg gagcatacgt cgcaaggcaa gctgccaaga gcattgttgc    1680
tagtggcctt gctcgccgct gcattgtcca agtatcatac gccatcggtg tcccagagcc    1740
actgtccgta ttcgtcgaca catacggcac tggcaggatc cctgacaagg agatcctcaa    1800
gattgtgaag gagaacttcg acttcaggcc tggcatgatc atcatcaacc ttgacctcaa    1860
gaaaggcggc aacggacgct acctcaagac ggcggcttac ggtcacttcg aagggacga    1920
cccagacttc acctgggagg tggtgaagcc cctcaagtgg gagaagcctt ctgcctaaaa    1980
gctccctttc ggaggctttt gctctgtccc attatggtgt tttgtttcct cgctgctcag    2040
cattgtgatt cttaacctgc ccccgctgc catttatgcc catgcacgct actttcctaa     2100
taataagtac ttataagggt attgtgtttg aatattttac ctagaggagg aggaggattt    2160
gttatctgtt attgcttaag ctt                                             2183
```

<210> SEQ ID NO 38
<211> LENGTH: 1485
<212> TYPE: DNA
<213> ORGANISM: Glycine max

<400> SEQUENCE: 38

```
agccaagccc cactcaacca ccacaccact ctctctgctc ttcttctacc tttcaagttt      60
ttaaagtatt aagatggcag agacattcct atttacctca gagtcagtga acgagggaca    120
ccctgacaag ctctgcgacc aaatctccga tgctgtcctc gacgcttgcc ttgaacagga    180
cccagacagc aaggttgcct gcgaaacatg caccaagacc aacttggtca tggtcttcgg    240
agagatcacc accaaggcca acgttgacta cgagaagatc gtgcgtgaca cctgcaggaa    300
catcggcttc gtctcaaacg atgtgggact tgatgctgac aactgcaagg tccttgtaaa    360
cattgagcag cagagccctg atattgccca gggtgtgcac ggccaccttc caaaagaccc    420
cgaggaaatc ggtgctggag accagggtca catgtttggc tatgccacgg acgaaacccc    480
agaattgatg ccattgagtc atgttcttgc aactaaactc ggtgctcgtc tcaccgaggt    540
tcgcaagaac ggaaccctgcc catggttgag gcctgatggg aaaacccaag tgactgttga    600
gtattacaat gacaacggtg ccatggttcc agttcgtgtc cacactgtgc ttatctccac    660
ccaacatgat gagactgtga ccaacgacga aattgcagct gacctcaagg agcatgtgat    720
caagccggtg atcccggaga agtaccttga tgagaagacc attttccact gaacccctc     780
tggccgtttt gtcattggag tcctcacgg tgatgctggc tcaccgccc gcaagatcat     840
catcgatact tacgaggat ggggtgctca tggtggtggt gctttctccg ggaaggatcc    900
caccaaggtt gataggagtg gtgcttacat tgtgagacag gctgctaaga gcattgtggc    960
aagtggacta gccagaaggt gcattgtgca agtgtcttat gccattggtg tgcccgagcc   1020
tttgtctgtc tttgttgaca cctatggcac cgggaagatc catgataagg agattctcaa   1080
cattgtgaag gagaactttg atttcaggcc cggtatgatc tccatcaacc ttgatctcaa   1140
gaggggtggg aataacaggt tcttgaagac tgctgcatat ggacacttcg gcagagagga   1200
ccctgacttc acatgggaag tggtcaagcc cctcaagtgg gagaaggcct aaggccattc   1260
attccactgc aatgtgctgg gagttttta gcgttgccct tataatgtct attatccata   1320
actttccacg tcccttgctc tgtgttttc tctcgtcgtc ctcctcctat tttgtttctc   1380
ctgcctttca tttgtaattt tttacatgat caactaaaaa atgtactctc tgttttccga   1440
ccattgtgtc tcttaatatc agtatcaaaa agaatgttcc aagtt                   1485
```

<210> SEQ ID NO 39
<211> LENGTH: 392
<212> TYPE: PRT
<213> ORGANISM: Gylcine max

<400> SEQUENCE: 39

```
Met Ala Glu Thr Phe Leu Phe Thr Ser Glu Ser Val Asn Glu Gly His
1               5                  10                  15

Pro Asp Lys Leu Cys Asp Gln Ile Ser Asp Ala Val Leu Asp Ala Cys
            20                  25                  30

Leu Glu Gln Asp Pro Asp Ser Lys Val Ala Cys Glu Thr Cys Thr Lys
        35                  40                  45

Thr Asn Leu Val Met Val Phe Gly Glu Ile Thr Thr Lys Ala Asn Val
    50                  55                  60

Asp Tyr Glu Lys Ile Val Arg Asp Thr Cys Arg Asn Ile Gly Phe Val
```

65                  70                  75                  80
Ser Asn Asp Val Gly Leu Asp Ala Asp Asn Cys Lys Val Leu Val Asn
                    85                  90                  95
Ile Glu Gln Gln Ser Pro Asp Ile Ala Gln Gly Val His Gly His Leu
                100                 105                 110
Thr Lys Arg Pro Glu Glu Ile Gly Ala Gly Asp Gln Gly His Met Phe
            115                 120                 125
Gly Tyr Ala Thr Asp Glu Thr Pro Glu Leu Met Pro Leu Ser His Val
        130                 135                 140
Leu Ala Thr Lys Leu Gly Ala Arg Leu Thr Glu Val Arg Lys Asn Gly
145                 150                 155                 160
Thr Cys Pro Trp Leu Arg Pro Asp Gly Lys Thr Gln Val Thr Val Glu
                165                 170                 175
Tyr Tyr Asn Asp Asn Gly Ala Met Val Pro Arg Val His Thr Val
                180                 185                 190
Leu Ile Ser Thr Gln His Asp Glu Thr Val Thr Asn Asp Glu Ile Ala
            195                 200                 205
Ala Asp Leu Lys Glu His Val Ile Lys Pro Val Ile Pro Glu Lys Tyr
        210                 215                 220
Leu Asp Glu Lys Thr Ile Phe His Leu Asn Pro Ser Gly Arg Phe Val
225                 230                 235                 240
Ile Gly Gly Pro His Gly Asp Ala Gly Leu Thr Gly Arg Lys Ile Ile
                245                 250                 255
Ile Asp Thr Tyr Gly Gly Trp Gly Ala His Gly Gly Ala Phe Ser
                260                 265                 270
Gly Lys Asp Pro Thr Lys Val Asp Arg Ser Gly Ala Tyr Ile Val Arg
            275                 280                 285
Gln Ala Ala Lys Ser Ile Val Ala Ser Gly Leu Ala Arg Arg Cys Ile
        290                 295                 300
Val Gln Val Ser Tyr Ala Ile Gly Val Pro Glu Pro Leu Ser Val Phe
305                 310                 315                 320
Val Asp Thr Tyr Gly Thr Gly Lys Ile His Asp Lys Glu Ile Leu Asn
                325                 330                 335
Ile Val Lys Glu Asn Phe Asp Phe Arg Pro Gly Met Ile Ser Ile Asn
                340                 345                 350
Leu Asp Leu Lys Arg Gly Gly Asn Asn Arg Phe Leu Lys Thr Ala Ala
            355                 360                 365
Tyr Gly His Phe Gly Arg Glu Asp Pro Asp Phe Thr Trp Glu Val Val
        370                 375                 380
Lys Pro Leu Lys Trp Glu Lys Ala
385                 390

<210> SEQ ID NO 40
<211> LENGTH: 1479
<212> TYPE: DNA
<213> ORGANISM: Lycopersicon esculentum

<400> SEQUENCE: 40
gaattcctac aaagaggtta tttctctcaa ggggtaaaaa gattgcccct tttcgacatt    60
tataatcctc tttttctctt tgttcgccgt tgggttcttc actttcctgt ttcttgagaa   120
tggaaacttt cttattcacc tccgagtctg tgaacgaggg tcacccagac aagctctgtg   180
atcagatctc tgatgcagtt cttgatgcct gccttgagca agatcccgag agcaaagttg   240
catgtgaaac ttgcaccaag accaacttgg tcatggtctt tggtgagatc acaaccaagg   300

-continued

| | |
|---|---|
| ctattgtaga ctatgagaag attgtgcgtg acacatgccg taatattgga tttgtttctg | 360 |
| atgatgttgg tcttgatgct gacaactgca aggtccttgt ttacattgag cagcaaagtc | 420 |
| ctgatattgc tcaaggtgtc cacgccatc tgaccaaacg ccccgaggag attggtgctg | 480 |
| gtgaccaggg ccacatgttt ggctatgcaa cagatgagac ccctgaatta atgcctctca | 540 |
| gtcacgtgct tgcaactaaa cttggtgccc gtcttacaga agtccgcaag aatggcacct | 600 |
| gcgcctggtt gaggcctgat ggcaagaccc aagttactgt tgagtatagc aatgacaatg | 660 |
| gtgccatggt tccaattagg gtacacactg ttcttatctc cacccaacac gatgagaccg | 720 |
| ttaccaatga tgagattgcc cgcgacctta aggagcatgt catcaaacca gtcatcccag | 780 |
| agaagtacct tgatgagaat actatttcc accttaaccc atctggccga ttcgttattg | 840 |
| gtggacctca tggtgatgct ggtctcactg gtcgtaaaat catcatcgac acttatggtg | 900 |
| gttggggtgc tcatggtggt ggtgcttct cgggcaaaga cccaaccaag gtcgacagga | 960 |
| gtggtgcata cattgtaagg caggctgcaa agagtatcgt agctagtgga cttgctcgta | 1020 |
| gatgcatcgt gcaggtatct tatgccatcg gtgtgcctga gccattgtct gtattcgttg | 1080 |
| acacctatgg cactggaaag atccctgaca gggaaatttt gaagatcgtt aaggagaact | 1140 |
| ttgacttcag acctgaatg atgtccatta acttggattt gaagaggggt ggcaatagaa | 1200 |
| gattcttgaa aactgctgcc tatggtcact ttggacgtga tgaccccgat ttcacatggg | 1260 |
| aagttgtcaa gcccctcaag tgggaaaagc cccaagacta ataagtgctt gcctatgttt | 1320 |
| ttgttctttg ttgtttgctt gtggctttag aatctccccc gtgtttgctt gtttgtcttt | 1380 |
| gtattttctc ttttgacccct ttattttgtt attgtcctgt ttccattgtg ttggatggat | 1440 |
| atcttaggcc ttggaatatt aaggaaagaa aaggaattc | 1479 |

<210> SEQ ID NO 41
<211> LENGTH: 1380
<212> TYPE: DNA
<213> ORGANISM: Triticum aestiva

<400> SEQUENCE: 41

| | |
|---|---|
| ccctcccttc ggttcatcgg cctcccgatc gagcagtaga agcagcgcaa gggcatcgct | 60 |
| agcactaaag aaatggcagc cgagacgttc ctcttcacgt ccgagtctgt gaacgagggc | 120 |
| catcccgaca agctctgtga ccaagtctcc gacgccgtct ggatgcctg cttggcccag | 180 |
| gatgccgaca gcaaggtcgc ctgcgagacc gtcaccaaga ccaacatggt catggtcttg | 240 |
| ggcgagatca ccaccaaggc caccgtcgac tatgagaaga tcgtgcgtga cacctgccgc | 300 |
| aacatcggtt tcatctctga tgacgttggt ctcgacgccg accgttgcaa rgtgctcgtc | 360 |
| aacatcgagc agcagtcccc tgacattgcc cagggtgttc atggacactt caccaagcgt | 420 |
| cccgaagaag tcggcgccgg tgaccagggc atcatgttcg gctatgccac cgatgagacc | 480 |
| cctgagctga tgcccctcaa gcacgtgctt gccaccaagc tyggagctcg cctcacsgag | 540 |
| gtccgcaaga atggcacctg cgcctgggtc aggcctgacg gaaagaccca ggtcacagtc | 600 |
| gagtacctaa acgaggatgg tgccatggta cctgttcgtg tgcacaccgt cctcatctcc | 660 |
| acccagcacg acgagaccgt caccaacgac gagattgctg cggacctcaa ggagcatgtc | 720 |
| atcaagccgg tgatccccgc aaagtacctc gatgagaaca ccatcttcca cctgaacccg | 780 |
| tctggccgct tcgtcatcgg cggccccac ggtgacgccg gtctcaccgg ccgcaagatc | 840 |
| atcatcgaca cctatggtgg ctggggagcc cacggcggcg gtgccttctc tggcaaggac | 900 |

```
ccaaccaagg tcgaccgyag tggcgcctac attgccaggc argccgccaa gagcatcatc    960
gccagcggcc tcgcacgccg ctgcattgtg cagatctcat acgccatcgg tgtgcctgag   1020
cctttgtctg tgttcgtcga ctcctacggc accggcaaga tccccgacag ggagatcctc   1080
aagctcgtga aggagaactt tgacttcagg cccgggatga tcagcatcaa cctggacttg   1140
aagaaaggtg aaacaggtt catcaagacc gctgcttacg gtcactttgg ccgtgatgat    1200
gccgacttca cctgggaggt ggtgaagccc ctcaagttcg acaaggcatc tgcctaagag   1260
catggcattc tcttggtctg ccgcctctca agttcgtcaa gacgggatca tgttgctcct   1320
gggaagtggg aagaagcatt agacattgaa gcgacgctct acactggtct tgttgtatgg   1380
```

<210> SEQ ID NO 42
<211> LENGTH: 394
<212> TYPE: PRT
<213> ORGANISM: Triticum aestiva

<400> SEQUENCE: 42

```
Met Ala Ala Glu Thr Phe Leu Phe Thr Ser Glu Ser Val Asn Glu Gly
1               5                   10                  15

His Pro Asp Lys Leu Cys Asp Gln Val Ser Asp Ala Val Leu Asp Ala
            20                  25                  30

Cys Leu Ala Gln Asp Ala Asp Ser Lys Val Ala Cys Glu Thr Val Thr
        35                  40                  45

Lys Thr Asn Met Val Met Val Leu Gly Glu Ile Thr Thr Lys Ala Thr
    50                  55                  60

Val Asp Tyr Glu Lys Ile Val Arg Asp Thr Cys Arg Asn Ile Gly Phe
65                  70                  75                  80

Ile Ser Asp Asp Val Gly Leu Asp Ala Asp Arg Cys Lys Val Leu Val
                85                  90                  95

Asn Ile Glu Gln Gln Ser Pro Asp Ile Ala Gln Gly Val His Gly His
            100                 105                 110

Phe Thr Lys Arg Pro Glu Glu Val Gly Ala Gly Asp Gln Gly Ile Met
        115                 120                 125

Phe Gly Tyr Ala Thr Asp Glu Thr Pro Glu Leu Met Pro Leu Lys His
    130                 135                 140

Val Leu Ala Thr Lys Leu Gly Ala Arg Leu Thr Glu Val Arg Lys Asn
145                 150                 155                 160

Gly Thr Cys Ala Trp Val Arg Pro Asp Gly Lys Thr Gln Val Thr Val
                165                 170                 175

Glu Tyr Leu Asn Glu Asp Gly Ala Met Val Pro Val Arg Val His Thr
            180                 185                 190

Val Leu Ile Ser Thr Gln His Asp Glu Thr Val Thr Asn Asp Glu Ile
        195                 200                 205

Ala Ala Asp Leu Lys Glu His Val Ile Lys Pro Val Ile Pro Ala Lys
    210                 215                 220

Tyr Leu Asp Glu Asn Thr Ile Phe His Leu Asn Pro Ser Gly Arg Phe
225                 230                 235                 240

Val Ile Gly Gly Pro His Gly Asp Ala Gly Leu Thr Gly Arg Lys Ile
                245                 250                 255

Ile Ile Asp Thr Tyr Gly Gly Trp Gly Ala His Gly Gly Ala Phe
            260                 265                 270

Ser Gly Lys Asp Pro Thr Lys Val Asp Arg Ser Gly Ala Tyr Ile Ala
        275                 280                 285

Arg Gln Ala Ala Lys Ser Ile Ile Ala Ser Gly Leu Ala Arg Arg Cys
```

```
                290                 295                 300
Ile Val Gln Ile Ser Tyr Ala Ile Gly Val Pro Glu Pro Leu Ser Val
305                 310                 315                 320

Phe Val Asp Ser Tyr Gly Thr Gly Lys Ile Pro Asp Arg Glu Ile Leu
                325                 330                 335

Lys Leu Val Lys Glu Asn Phe Asp Phe Arg Pro Gly Met Ile Ser Ile
                340                 345                 350

Asn Leu Asp Leu Lys Lys Gly Gly Asn Arg Phe Ile Lys Thr Ala Ala
                355                 360                 365

Tyr Gly His Phe Gly Arg Asp Asp Ala Asp Phe Thr Trp Glu Val Val
                370                 375                 380

Lys Pro Leu Lys Phe Asp Lys Ala Ser Ala
385                 390

<210> SEQ ID NO 43
<211> LENGTH: 1353
<212> TYPE: DNA
<213> ORGANISM: Hordeum vulgare

<400> SEQUENCE: 43
gaattccgga tagcatcagc acaactgcac gagagcatct ctaccaccaa agaaatggcg      60
gccgagacgt tcctcttcac gtccgagtcc gtgaacgagg ccatcccga caagctgtgc     120 gaccaggtct ctgacgccgt cttggacgcc tgcttggccc aggatcctga cagcaaggtt     180
gcttgcgaga cctgcaccaa gaccaacatg gtcatggtct tcggcgagat caccaccaag     240
gccaccgttg actatgagaa gattgtgcgc gacacctgcc gtgacatcgg cttcatctct     300
gacgacgtcg gtctcgatgc cgaccattgc aaggtgctcg tcaacatcga gcagcaatcc     360
cctgacattg cccagggtgt tcacggacac ttcaccaagc gtccagaaga ggtcggcgcc     420
ggtgaccagg gcatcatgtt tggctacgcc actgatgaga cccctgagct gatgcccctc     480
acccacatgc ttgccaccaa gctcggagct cgcctcaccg aggtccgcaa gaatggcacc     540
tgcgcctggc tcaggcctga tggaaagacc caggtcacca ttgagtacct aaacgagggt     600
ggtgccatgg tgcccgttcg tgtgcacacc gtcctcatct ccacccagca tgatgagacc     660
gtcaccaacg atgagatcgc tgcagacctc aaggagcatg tcatcaagcc ggtgattccc     720
gggaagtacc tcgatgagaa caccatcttc cacctgaacc catcgggccg ctttgtcatc     780
ggtggccctc acggcgatgc cggtctcacc gcccgcaaga tcatcatcga cacctatggt     840
ggctggggag cccacggcgg cggtgccttc tctggcaagg accctaccaa ggtcgaccgc     900
agtggcgcct acattgccag gcaggctgcc aagagcatca tcgccagcgg cctcgcacgc     960
cggtgcattg tgcagatctc atatgccatc ggtgtacctg agcctttgtc tgtgttcgtc    1020
gactcctacg gcactggcaa gatccctgac agggagatcc tcaagctcgt gaaggagaac    1080
tttgacttca gacccgggat gatcacgatc aacctcgact tgaagaaagg tggaaacagg    1140
ttcatcaaga cagctgctta cggtcacttt ggccgcgatg atgctgactt cacctgggag    1200
gtggtgaagc cctcaagttt cgacaaggca tctgcttaag aagaagacat acacattgagg    1260 gttcttcttg gtctgatgcc tctcaagttc ggcaaggcgg atcctttttg ctcctcggaa    1320
gtaagaagaa gcattcaaca tcgcccggaa ttc                                 1353

<210> SEQ ID NO 44
<211> LENGTH: 1853
<212> TYPE: DNA
<213> ORGANISM: Zea mays
```

-continued

```
<400> SEQUENCE: 44
gcacgagccc actctgccgc cgccagcttg cccaccatgg cggccgccgc ctccatgtcg      60
ttcctcctct cccaccccca gtcgcgctct gccaccccaa gccgccacct cccgctccgt     120
ccggcagccc gccgcgtccg gtgcgccacc gacgccgccg ccctttcccc ggcggtcacc     180
accaagcacc ggcgcgcggc ggatgagaac atccgcgagg aggcggcgcg cacccggcc      240
ccgaagcagg gcctgtcggc gtggtacgag cccttcccgc cggccccgaa cggcgacccc     300
aacgagcgct actccctgga cgagatcgtg taccggtcca gctcgggggg cctcctcgac     360
gtgcggcacg acatggaggc gctgtcccgc ttctcgggcg cctactggcg cgacctcttc     420
gactcccgca tcgggcgcac cacctggccg tacgggtccg gcgtgtggtc caagaaggag     480
ttcgtgctcc ccgagatcga gcccgaccac atcgtctccc tgttcgaggg caactcgaac     540
ctgttctggg ccgagcggct cgggcgcgac cacctcggcg ggatgaacga cctgtgggtg     600
aagcactgcg gcatctccca cacggggtcg ttcaaggacc tcggcatgac cgtgctggtg     660
agccaggtga accggctccg ccgcgcgccc tgtcgcgccc catcgccggc gtcgggtgc      720
gcgtccacgg gggacacctc ggccgcgctc tccgcctact gcgccgccgc ggggatcccg     780
gccatcgtct cctcccccgc caaccgcatc tcgctggagc agctcatcca gcccatcgcc     840
aacgcgcca ccgtgctctc gctcgacacc gacttcgacg ggtgcatgcg gctcatcagg      900
gaggtgaccg ccgagctgcc tatctacctc gccaactcgc tcaactccct ccgcctcgag     960
gggcagaaga cggcggccat cgagatactg cagcagttcg actgggaggt gcccgactgg    1020
gtgatcgtgc cgggaggcaa cctggggaac atatacgcct tctacaaggg gttcgagatg    1080
tgccgtgtcc tcgggctcgt cgaccgcgtg ccgcggctcg tctgcgcgca ggcggccaac    1140
gcgaacccgc tctacggcta ctacaagaca ggctggaccg agttccagcc gcaggtggcc    1200
aggccgacgt tcgcgtcagc gatccagatc ggcgacccgg tgtccgtcga ccgggccgtg    1260
gtcgcgctca aggcgacgga cggcattgtc gaggaggcga cggaggaaga gctcatgaac    1320
gcgatgtcgc tcgccgaccg cacggggatg ttcgcttgcc cgcacaccgg ggtcgcgctc    1380
gccgccctgt tcaagctcag ggaccagcgc gtcatcggga cgaacgaccg caccgtggtc    1440
gtcagcacgg ctcacggcct caagttctcg cagtcgaaga tcgactacca tgacagcaag    1500
atcgaggaca tggcttgcaa gtactccaac ccgcctgtga gcgtgaaggc cgactttggc    1560
gccgtcatga tgtgctgaa gaagaggctc aagggcaagc tctgagcgcc tgtgcctggc     1620
taatgcaatc aactgattgg aatgcagtgg tttcgtcggt atcgggggt cttttaggct      1680
tcagaaattc tgtctgggtt agactatctg tttgtggagt ttagcaggag aatggatatc    1740
tctcctgcaa gactggcgct ctctattgtg ctacgatgtg ttaccatgga taataagtga    1800
cctagttgct gttggattga aaaaaaaaaa aaaaaaaaa aaaaaaaaa aaa              1853
```

```
<210> SEQ ID NO 45
<211> LENGTH: 522
<212> TYPE: PRT
<213> ORGANISM: Zea mays

<400> SEQUENCE: 45

Met Ala Ala Ala Ala Ser Met Ser Phe Leu Leu Ser His Pro Gln Ser
  1               5                  10                  15

Arg Ser Ala Thr Pro Ser Arg His Leu Pro Leu Arg Pro Ala Ala Arg
             20                  25                  30
```

```
Arg Val Arg Cys Ala Thr Asp Ala Ala Leu Ser Pro Ala Val Thr
         35                  40                  45

Thr Lys His Arg Arg Ala Ala Asp Glu Asn Ile Arg Glu Glu Ala Ala
     50                  55                  60

Arg His Pro Ala Pro Lys Gln Gly Leu Ser Ala Trp Tyr Glu Pro Phe
 65                  70                  75                  80

Pro Pro Ala Pro Asn Gly Asp Pro Asn Glu Arg Tyr Ser Leu Asp Glu
                 85                  90                  95

Ile Val Tyr Arg Ser Ser Gly Gly Leu Leu Asp Val Arg His Asp
             100                 105                 110

Met Glu Ala Leu Ser Arg Phe Ser Gly Ala Tyr Trp Arg Asp Leu Phe
         115                 120                 125

Asp Ser Arg Ile Gly Arg Thr Thr Trp Pro Tyr Gly Ser Gly Val Trp
     130                 135                 140

Ser Lys Lys Glu Phe Val Leu Pro Glu Ile Glu Pro Asp His Ile Val
145                 150                 155                 160

Ser Leu Phe Glu Gly Asn Ser Asn Leu Phe Trp Ala Glu Arg Leu Gly
                 165                 170                 175

Arg Asp His Leu Gly Gly Met Asn Asp Leu Trp Val Lys His Cys Gly
             180                 185                 190

Ile Ser His Thr Gly Ser Phe Lys Asp Leu Gly Met Thr Val Leu Val
         195                 200                 205

Ser Gln Val Asn Arg Leu Arg Arg Ala Pro Leu Ser Arg Pro Ile Ala
     210                 215                 220

Gly Val Gly Cys Ala Ser Thr Gly Asp Thr Ser Ala Ala Leu Ser Ala
225                 230                 235                 240

Tyr Cys Ala Ala Ala Gly Ile Pro Ala Ile Val Phe Leu Pro Ala Asn
                 245                 250                 255

Arg Ile Ser Leu Glu Gln Leu Ile Gln Pro Ile Ala Asn Gly Ala Thr
             260                 265                 270

Val Leu Ser Leu Asp Thr Asp Phe Asp Gly Cys Met Arg Leu Ile Arg
         275                 280                 285

Glu Val Thr Ala Glu Leu Pro Ile Tyr Leu Ala Asn Ser Leu Asn Ser
     290                 295                 300

Leu Arg Leu Glu Gly Gln Lys Thr Ala Ala Ile Glu Ile Leu Gln Gln
305                 310                 315                 320

Phe Asp Trp Glu Val Pro Asp Trp Val Ile Val Pro Gly Gly Asn Leu
                 325                 330                 335

Gly Asn Ile Tyr Ala Phe Tyr Lys Gly Phe Glu Met Cys Arg Val Leu
             340                 345                 350

Gly Leu Val Asp Arg Val Pro Arg Leu Val Cys Ala Gln Ala Ala Asn
         355                 360                 365

Ala Asn Pro Leu Tyr Gly Tyr Tyr Lys Thr Gly Trp Thr Glu Phe Gln
     370                 375                 380

Pro Gln Val Ala Arg Pro Thr Phe Ala Ser Ala Ile Gln Ile Gly Asp
385                 390                 395                 400

Pro Val Ser Val Asp Arg Ala Val Val Ala Leu Lys Ala Thr Asp Gly
                 405                 410                 415

Ile Val Glu Glu Ala Thr Glu Glu Leu Met Asn Ala Met Ser Leu
             420                 425                 430

Ala Asp Arg Thr Gly Met Phe Ala Cys Pro His Thr Gly Val Ala Leu
         435                 440                 445

Ala Ala Leu Phe Lys Leu Arg Asp Gln Arg Val Ile Gly Thr Asn Asp
```

```
               450                 455                 460
Arg Thr Val Val Ser Thr Ala His Gly Leu Lys Phe Ser Gln Ser
465                 470                 475                 480

Lys Ile Asp Tyr His Asp Ser Lys Ile Glu Asp Met Ala Cys Lys Tyr
                485                 490                 495

Ser Asn Pro Pro Val Ser Val Lys Ala Asp Phe Gly Ala Val Met Asp
                500                 505                 510

Val Leu Lys Lys Arg Leu Lys Gly Lys Leu
            515                 520

<210> SEQ ID NO 46
<211> LENGTH: 1902
<212> TYPE: DNA
<213> ORGANISM: Zea mays

<400> SEQUENCE: 46
gcacgagtcg gccttcccca ctgtactctc aatctcgcc gccaagcctc accgcaccat      60
ggcgaccttc accgcggcct cctccctctc cctcctcttc tcccacccgc actcccactc     120
ccgccaacca tccgcccagg ggcccaccgc cagctcccac ctccacctgc atccgcgcgc     180
cagccgcgcg cgctgcgcct cttccgacac gacggccacg aagcaccgcc gcccagcgga     240
ggagaacatc cgcgaggagg cggcgcggct ccgaggcccg gccagggtt tctctgcgtg      300
gtacgagccc ttcccgccgg cgcccggcgg cgacccgaac gagcgctact cgctggacga     360
ggtcgtctac cgctccagct cggggggcct cctcgacgtg cgccacgaca tggaggcgct     420
ggcccgctac ccggggtcct actggcgtga cctcttcgac tcccgcgtcg gccgcaccgc     480
ctggccctac ggctcgggcg tctggtccaa gaaggagttc gtgctccccg agatcgactc     540
cgaccacatc gtctccctct tcgagggcaa ctccaacctc ttctgggcgg agcgcctcgg     600
ccgcgagcac ctcggcggga tgaacgacct ctgggtcaag cactgtggca tctcccacac     660
gggctccttc aaggacctcg gcatgacggt gctcgtcagc caggtgaacc gcctccgccg     720
cgcgccgctc tcgcgcccca tcgccggtgt cggctgcgcg tccacgggag acacctccgc     780
cgcgctctcg gcctactgcg cagccgcggg aatccccgcc atcgtgttcc tgccagcgga     840
ccgcatctcg ctgcagcagc tcatccagcc gatcgccaac ggcgccaccg tgctctctct     900
agacactgat tttgatggct gcatgcggct cattcgcgag gtcactgcag agctgccaat     960
ctaccttgcc aattcgctca acccgctccg ccttgagggg cagaagacag cggccatcga    1020
gatattgcag cagttcaatt ggcaggtgcc agattgggtc attgttccag gaggcaatct    1080
tgggaatatc tatgcattct acaagggggtt tgagatgtgc cgcgttcttg acttgttga    1140
tcgcgtgcca cggcttgtct cgcacaggc tgcaaatgca aatccattgt accggtacta    1200
caagtcaggt tggactgagt ttgagccaca aactgccgag actacatttg catctgcgat    1260
acagattggt gatcctgtat ctgttgaccg tgcggtggtc gcgctgaagg ccactgacgg    1320
tattgtggag gaggctacag aggaggagct aatggatgca acggcgcttg ctgaccgcac    1380
tgggatgttt gcttgcccac atactggggt tgcacttgct gctttgtttta agcttcaggg    1440
tcagcgtata attggcccta atgaccgcac tgtggttgtt agcacagctc atgggctgaa    1500
gttcacgcag tcaaagattg actaccatga caaaaacatc aaagacatgg tttgccagta    1560
tgctaatcca ccgatcagtg tgaaggctga ctttggttct gtgatggatg ttctccagaa    1620
aaatctcaat ggtaagatat aaagttatat gattaattaa ccctccaaac tgttttttt    1680
tgttttttcg ttccaggaat tttattcctg agtctttcaa cttgtttgg tgaacatggt    1740
```

```
atggtgctaa aatctagacc taataccttg tagtactagt tctggaggct cttttggttg    1800
taggtcgaag tggatagagc tgttccttgt actttatctg tttcatgtaa tatgaataat    1860
aaattatggt ctaaatattt gaataaaaaa aaaaaaaaaa aa                       1902
```

<210> SEQ ID NO 47
<211> LENGTH: 527
<212> TYPE: PRT
<213> ORGANISM: Zea mays

<400> SEQUENCE: 47

```
Met Ala Thr Phe Thr Ala Ala Ser Ser Leu Ser Leu Leu Phe Ser His
1               5                   10                  15

Pro His Ser His Ser Arg Gln Pro Ser Ala Gln Gly Pro Thr Ala Ser
            20                  25                  30

Ser His Leu His Leu His Pro Arg Ala Ser Arg Ala Arg Cys Ala Ser
        35                  40                  45

Ser Asp Thr Ala Thr Lys His Arg Arg Pro Ala Glu Glu Asn Ile
    50                  55                  60

Arg Glu Glu Ala Ala Arg Leu Arg Gly Pro Ala Gln Gly Phe Ser Ala
65                  70                  75                  80

Trp Tyr Glu Pro Phe Pro Pro Ala Pro Gly Gly Asp Pro Asn Glu Arg
                85                  90                  95

Tyr Ser Leu Asp Glu Val Val Tyr Arg Ser Ser Gly Gly Leu Leu
            100                 105                 110

Asp Val Arg His Asp Met Glu Ala Leu Ala Arg Tyr Pro Gly Ser Tyr
        115                 120                 125

Trp Arg Asp Leu Phe Asp Ser Arg Val Gly Arg Thr Ala Trp Pro Tyr
    130                 135                 140

Gly Ser Gly Val Trp Ser Lys Lys Glu Phe Val Leu Pro Glu Ile Asp
145                 150                 155                 160

Ser Asp His Ile Val Ser Leu Phe Glu Gly Asn Ser Asn Leu Phe Trp
                165                 170                 175

Ala Glu Arg Leu Gly Arg Glu His Leu Gly Gly Met Asn Asp Leu Trp
            180                 185                 190

Val Lys His Cys Gly Ile Ser His Thr Gly Ser Phe Lys Asp Leu Gly
        195                 200                 205

Met Thr Val Leu Val Ser Gln Val Asn Arg Leu Arg Arg Ala Pro Leu
    210                 215                 220

Ser Arg Pro Ile Ala Gly Val Gly Cys Ala Ser Thr Gly Asp Thr Ser
225                 230                 235                 240

Ala Ala Leu Ser Ala Tyr Cys Ala Ala Ala Gly Ile Pro Ala Ile Val
                245                 250                 255

Phe Leu Pro Ala Asp Arg Ile Ser Leu Gln Gln Leu Ile Gln Pro Ile
            260                 265                 270

Ala Asn Gly Ala Thr Val Leu Ser Leu Asp Thr Asp Phe Asp Gly Cys
        275                 280                 285

Met Arg Leu Ile Arg Glu Val Thr Ala Glu Leu Pro Ile Tyr Leu Ala
    290                 295                 300

Asn Ser Leu Asn Pro Leu Arg Leu Glu Gly Gln Lys Thr Ala Ala Ile
305                 310                 315                 320

Glu Ile Leu Gln Gln Phe Asn Trp Gln Val Pro Asp Trp Val Ile Val
                325                 330                 335

Pro Gly Gly Asn Leu Gly Asn Ile Tyr Ala Phe Tyr Lys Gly Phe Glu
```

```
                  340               345               350
Met Cys Arg Val Leu Gly Leu Val Asp Arg Val Pro Arg Leu Val Cys
        355                   360                   365

Ala Gln Ala Ala Asn Ala Asn Pro Leu Tyr Arg Tyr Tyr Lys Ser Gly
        370                   375                   380

Trp Thr Glu Phe Glu Pro Gln Thr Ala Glu Thr Thr Phe Ala Ser Ala
385                 390                   395                   400

Ile Gln Ile Gly Asp Pro Val Ser Val Asp Arg Ala Val Val Ala Leu
                405                   410                   415

Lys Ala Thr Asp Gly Ile Val Glu Glu Ala Thr Glu Glu Glu Leu Met
            420                   425                   430

Asp Ala Thr Ala Leu Ala Asp Arg Thr Gly Met Phe Ala Cys Pro His
            435                   440                   445

Thr Gly Val Ala Leu Ala Ala Leu Phe Lys Leu Gln Gly Gln Arg Ile
        450                   455                   460

Ile Gly Pro Asn Asp Arg Thr Val Val Ser Thr Ala His Gly Leu
465                 470                   475                   480

Lys Phe Thr Gln Ser Lys Ile Asp Tyr His Asp Lys Asn Ile Lys Asp
                485                   490                   495

Met Val Cys Gln Tyr Ala Asn Pro Pro Ile Ser Val Lys Ala Asp Phe
            500                   505                   510

Gly Ser Val Met Asp Val Leu Gln Lys Asn Leu Asn Gly Lys Ile
            515                   520                   525

<210> SEQ ID NO 48
<211> LENGTH: 2315
<212> TYPE: DNA
<213> ORGANISM: Glycine max

<400> SEQUENCE: 48
gtcgcggcgg cggctggcaa gtagtagtat taaaaaagtt gatgggataa ttggcattgg      60
ttgagtttgg ttcaaattga gaaaatcatt actccattaa ccattcattc accaatcctc     120
catggcttcc tcttctctgt ttcagtctct ccctttctct ctccaaacct ctaaaccta      180 cgcgcctccc aaacccgccg cccacttcgt tgtccgcgcc caatccccc tcactcagaa      240 caacaactcc tcctccaagc atcgccgccc gccgacgag aacatccgcg acgaggcccg      300
ccgcatcaat gcgccccacg accaccacct cttctcggcc aagtacgtcc ccttcaacgc      360
cgactcctcc tcctcctcct ccacggagtc ctactcgctc gacgagatcg tctaccgctc      420
ccaatccggc ggcctcctgg acgtccagca cgacatggat gccctcaagc gtttcgacgg      480
cgagtactgg cgcaacctct tcgactcgcg cgtgggcaaa accacctggc ttacggctc      540 cggcgtctgg agcaaaaaag aatgggtcct ccccgagatc cacgacgacg atatcgtctc      600
cgccttcgag ggtaactcca acctcttctg ggccgagcgt ttcggcaaac agttcctcgg      660
catgaacgat ttgtgggtca acactgcggg aatcagccac acgggcagct tcaaggatct      720
cggcatgacc gtcctcgtca gccaggtcaa tcgcttgaga aaaatgaacc gccccgtcgt      780
cggtgttggt tgcgcctcca ccggtgacac atcggccgct ttatccgcct attgcgcttc      840
cgctgccatt ccttccattg tgttttgcc tgctaataaa atctctcttg cccaacttgt      900
tcagcctatt gccaatggag cctttgtgtt gagtatcgac actgattttg atggttgcat      960
gcagttgatc agagaagtca ctgctgaatt gcctatttat ttggctaact ctctcaacag     1020
tttgaagttg aagggcaga aaactgctgc tattgagatt ctgcagcagt ttgattggca     1080
```

```
ggttcctgat tgggtcattg tgcctggaag caaccttggc aacatttatg ccttttacaa    1140
agggtttaag atgtttcaag agcttgggct tgtggataag attccaaggc ttgtttgtgc    1200
tcaggctgcc aatgctgatc ctttgtattt gtactttaaa tccgggtgga aggagtttaa    1260
gcctgtgaag tcgagcacta catttgcttc tgccattcaa attggtgatc ctgtttccat    1320
tgacagggcg gttcacgcgc taaagagttg cgatgggatt gtggaggagg ccacggagga    1380
ggagttgatg gatgctacag cgcaggcgga ttctactggg atgtttattt gcccccacac    1440
cggggttgct ttaactgcat tgtttaagct caggaacagc ggggttatta aggccactga    1500
taggactgtg tgggttagca ctgctcatgg cttgaagttc actcagtcca agattgatta    1560
ccattctaag gacatcaagg acatggcttg ccgctatgct aacccgccca tgcaagtgaa    1620
ggcagacttt ggctcggtta tggatgtttt gaagacgtat ttgcagagta aggctcatta    1680
ggttagcatt gcaagttttg ctcctcctga gtttgctcat tatttactta cttttaggca    1740
ctactgctgt attgtctttt ctatgagcta ggtttgagtg ttgtaataat ttgcttgctg    1800
cattatgtat gccgtctagt gttccatatt gggcatcatc cttagtattt gttgtagatt    1860
ttctttgctg agcatttgat ataatagctc aagtaggaaa atgaattggg tactatgagg    1920
aatgcatatc attggcttgt tattactgga ttccagacca ccccaaaaga aaataattcc    1980
aaaaaatata attagaacaa atttcgtcct tgttatgctg ttggcattaa gctcagtgtg    2040
ggtattacca agcaactcga aatcaagaga aaaaaaaatt gacagcaaag gagctgcatt    2100
gttggactga gtcacatcac ttcattgcta tgtcgtcata tttcgttgaa ttacgggaag    2160
gcagcatgca cagcaatatg cagcgattaa ctgaagccac accgcacaca ttgaagtagt    2220
agtcaattta gacactccat cttgtacttt ctacaaaaat gaattttcct tagccattaa    2280
gtataatatt ttattctaaa aaaaaaaaaa aaaa                                2315
```

<210> SEQ ID NO 49
<211> LENGTH: 519
<212> TYPE: PRT
<213> ORGANISM: Glycine max

<400> SEQUENCE: 49

```
Met Ala Ser Ser Ser Leu Phe Gln Ser Leu Pro Phe Ser Leu Gln Thr
  1               5                  10                  15

Ser Lys Pro Tyr Ala Pro Pro Lys Pro Ala Ala His Phe Val Val Arg
             20                  25                  30

Ala Gln Ser Pro Leu Thr Gln Asn Asn Asn Ser Ser Lys His Arg
         35                  40                  45

Arg Pro Ala Asp Glu Asn Ile Arg Asp Glu Ala Arg Arg Ile Asn Ala
     50                  55                  60

Pro His Asp His His Leu Phe Ser Ala Lys Tyr Val Pro Phe Asn Ala
 65                  70                  75                  80

Asp Ser Ser Ser Ser Ser Thr Glu Ser Tyr Ser Leu Asp Glu Ile
                 85                  90                  95

Val Tyr Arg Ser Gln Ser Gly Gly Leu Leu Asp Val Gln His Asp Met
            100                 105                 110

Asp Ala Leu Lys Arg Phe Asp Gly Glu Tyr Trp Arg Asn Leu Phe Asp
        115                 120                 125

Ser Arg Val Gly Lys Thr Thr Trp Pro Tyr Gly Ser Gly Val Trp Ser
    130                 135                 140

Lys Lys Glu Trp Val Leu Pro Glu Ile His Asp Asp Ile Val Ser
145                 150                 155                 160
```

```
Ala Phe Glu Gly Asn Ser Asn Leu Phe Trp Ala Glu Arg Phe Gly Lys
                165                 170                 175

Gln Phe Leu Gly Met Asn Asp Leu Trp Val Lys His Cys Gly Ile Ser
            180                 185                 190

His Thr Gly Ser Phe Lys Asp Leu Gly Met Thr Val Leu Val Ser Gln
        195                 200                 205

Val Asn Arg Leu Arg Lys Met Asn Arg Pro Val Val Gly Val Gly Cys
    210                 215                 220

Ala Ser Thr Gly Asp Thr Ser Ala Ala Leu Ser Ala Tyr Cys Ala Ser
225                 230                 235                 240

Ala Ala Ile Pro Ser Ile Val Phe Leu Pro Ala Asn Lys Ile Ser Leu
                245                 250                 255

Ala Gln Leu Val Gln Pro Ile Ala Asn Gly Ala Phe Val Leu Ser Ile
            260                 265                 270

Asp Thr Asp Phe Asp Gly Cys Met Gln Leu Ile Arg Glu Val Thr Ala
        275                 280                 285

Glu Leu Pro Ile Tyr Leu Ala Asn Ser Leu Asn Ser Leu Lys Leu Glu
    290                 295                 300

Gly Gln Lys Thr Ala Ala Ile Glu Ile Leu Gln Gln Phe Asp Trp Gln
305                 310                 315                 320

Val Pro Asp Trp Val Ile Val Pro Gly Ser Asn Leu Gly Asn Ile Tyr
                325                 330                 335

Ala Phe Tyr Lys Gly Phe Lys Met Phe Gln Glu Leu Gly Leu Val Asp
            340                 345                 350

Lys Ile Pro Arg Leu Val Cys Ala Gln Ala Ala Asn Ala Asp Pro Leu
        355                 360                 365

Tyr Leu Tyr Phe Lys Ser Gly Trp Lys Glu Phe Lys Pro Val Lys Ser
    370                 375                 380

Ser Thr Thr Phe Ala Ser Ala Ile Gln Ile Gly Asp Pro Val Ser Ile
385                 390                 395                 400

Asp Arg Ala Val His Ala Leu Lys Ser Cys Asp Gly Ile Val Glu Glu
                405                 410                 415

Ala Thr Glu Glu Glu Leu Met Asp Ala Thr Ala Gln Ala Asp Ser Thr
            420                 425                 430

Gly Met Phe Ile Cys Pro His Thr Gly Val Ala Leu Thr Ala Leu Phe
        435                 440                 445

Lys Leu Arg Asn Ser Gly Val Ile Lys Ala Thr Asp Arg Thr Val Val
    450                 455                 460

Val Ser Thr Ala His Gly Leu Lys Phe Thr Gln Ser Lys Ile Asp Tyr
465                 470                 475                 480

His Ser Lys Asp Ile Lys Asp Met Ala Cys Arg Tyr Ala Asn Pro Pro
                485                 490                 495

Met Gln Val Lys Ala Asp Phe Gly Ser Val Met Asp Val Leu Lys Thr
            500                 505                 510

Tyr Leu Gln Ser Lys Ala His
        515

<210> SEQ ID NO 50
<211> LENGTH: 2055
<212> TYPE: DNA
<213> ORGANISM: Glycine max

<400> SEQUENCE: 50
gcacgaggca taaagcatta ctccattcca cactgtcgat ggcttcctca tctcttttc     60
```

```
agtctctccc tttctctctc aaaaccacta aaccctacgc gcttcccaaa cccgccgcca    120
atttcgtaat ccgcgcccaa tccccctca ctcagaacac caacgccgcc tcctccgcct    180
ccaagcatcg ccgccccgcc gacgagaaca tccgcgacga ggcccgccgc atcaatgctc    240
cccacgacca ccacctcttc tcggccaaat acgtcccttt caatgccgac ccttcctcct    300
ccacgacgga gtcctactcg ctcgacgaga tcgtctaccg ctcccaatcc ggtgcctcc     360
tcgacgtcca gcacgacatg gacgccctca gcgcttcga cggcgagtac tggcgcaacc    420
tcttcgactc tcgcgtcggc aagaccacct ggccctacgg ctccgcgtc tggagcaaaa     480
aagagtgggt cctccctgag atccacgacg acgacatcgt ctccgccttc gaaggaaact    540
ccaacctctt ctgggccgag cgtttcggca acagttcct cggcatgaac gatttgtggg    600
tcaaacactg cggaatcagc cacaccggca gcttcaagga tctcggcatg accgtcctcg    660
ttagccaggt caaccgcttg agaaaaatga atcgccccgt cgtcggtgtc ggttgcgcct    720
ccaccggtga cacctccgcc gctttatctg cttattgcgc ttcggcggcg attccttcca    780
ttgtgtttct gcctgctaat aaaatctcgc ttgctcaact tgttcagcct attgccaatg    840
gtgcctttgt gttgagtatc gacactgatt ttgatggttg catgcagttg atcagagagg    900
tcactgctga gttgcctatt tatttggcta actctctcaa cagtttgaga ttggaagggc    960
agaaaactgc tgctattgag attctgcagc agtttgattg gcaggttcct gattgggtca    1020
ttgtgcctgg tggcaacctt ggcaacattt atgccttta caaaggcttc aagatgtgtc    1080
aagagcttgg tcttgtggat aagattccaa ggcttgtttg tgcccaggct gccaatgctg    1140
atcctttgta tttgtactt aaatccggct ggaaggagtt taagcctgtg aagtcaagca    1200
ctaccttgc ctctgccatt caattggtg atcctgtttc catcgacagg gcggttcacg    1260
ccctaaagag ttgcgatggg atcgtggagg aggccaccga ggaggagttg atggatgcta    1320
cggcgcaggc agattccact gggatgttta tctgccccca cactgggggtt gctttgactg    1380
ctttgtttaa gctcaggaac agtgggctta ttaaggccac tgataggact gtggtggtta    1440
gcactgctca tggcctcaag ttcactcagt ccaagatcga ttaccattct aaggacatca    1500
aggacatggc ttgccgctat gctaaccctc ccatgcaagt caaggctgat tttgggtcgg    1560
ttatggatgt tttgaagacg tatttgcaga gtaagactca ttaggttagc attgcaactt    1620
tttctcctct cttcctgagt ttgctgctga ttatttactt actattatta gccacttcta    1680
ctcctgtttt gtcttttcta taagctaggt ttgagtattg tagtaatttg cctgctgcat    1740
tatgtatgct gtgctccata ttggggcatc ttagtatttg ttgtagattt tctttgttga    1800
gcatttaata taatagctca agtagaaaaa aattaattgg atacaatgag ggaggaatgc    1860
acattgttgg cttgttatta ctggattcca gaccagacca cgccatcccc aaaagaaaat    1920
aattccaaaa aatataatta gaacagattt ctttcacttt catgttatgc tgttggcatt    1980
aagctaagtg tgggtattac caagcaactc tatgcaatct gtgacaagta attaaatcaa    2040
aaaaaaaaaa aaaaa                                                    2055
```

<210> SEQ ID NO 51
<211> LENGTH: 521
<212> TYPE: PRT
<213> ORGANISM: Glycine max

<400> SEQUENCE: 51

Met Ala Ser Ser Ser Leu Phe Gln Ser Leu Pro Phe Ser Leu Lys Thr
 1               5                  10                  15

-continued

```
Thr Lys Pro Tyr Ala Leu Pro Lys Pro Ala Ala Asn Phe Val Ile Arg
         20                  25                  30
Ala Gln Ser Pro Leu Thr Gln Asn Thr Asn Ala Ala Ser Ser Ala Ser
         35                  40                  45
Lys His Arg Arg Pro Ala Asp Glu Asn Ile Arg Asp Glu Ala Arg Arg
         50                  55                  60
Ile Asn Ala Pro His Asp His Leu Phe Ser Ala Lys Tyr Val Pro
 65                  70                  75                  80
Phe Asn Ala Asp Pro Ser Ser Ser Thr Glu Ser Tyr Ser Leu Asp
                 85                  90                  95
Glu Ile Val Tyr Arg Ser Gln Ser Gly Gly Leu Leu Asp Val Gln His
                100                 105                 110
Asp Met Asp Ala Leu Lys Arg Phe Asp Gly Glu Tyr Trp Arg Asn Leu
                115                 120                 125
Phe Asp Ser Arg Val Gly Lys Thr Thr Trp Pro Tyr Gly Ser Gly Val
                130                 135                 140
Trp Ser Lys Lys Glu Trp Val Leu Pro Glu Ile His Asp Asp Asp Ile
145                 150                 155                 160
Val Ser Ala Phe Glu Gly Asn Ser Asn Leu Phe Trp Ala Glu Arg Phe
                165                 170                 175
Gly Lys Gln Phe Leu Gly Met Asn Asp Leu Trp Val Lys His Cys Gly
                180                 185                 190
Ile Ser His Thr Gly Ser Phe Lys Asp Leu Gly Met Thr Val Leu Val
                195                 200                 205
Ser Gln Val Asn Arg Leu Arg Lys Met Asn Arg Pro Val Val Gly Val
                210                 215                 220
Gly Cys Ala Ser Thr Gly Asp Thr Ser Ala Ala Leu Ser Ala Tyr Cys
225                 230                 235                 240
Ala Ser Ala Ala Ile Pro Ser Ile Val Phe Leu Pro Ala Asn Lys Ile
                245                 250                 255
Ser Leu Ala Gln Leu Val Gln Pro Ile Ala Asn Gly Ala Phe Val Leu
                260                 265                 270
Ser Ile Asp Thr Asp Phe Asp Gly Cys Met Gln Leu Ile Arg Glu Val
                275                 280                 285
Thr Ala Glu Leu Pro Ile Tyr Leu Ala Asn Ser Leu Asn Ser Leu Arg
                290                 295                 300
Leu Glu Gly Gln Lys Thr Ala Ala Ile Glu Ile Leu Gln Gln Phe Asp
305                 310                 315                 320
Trp Gln Val Pro Asp Trp Val Ile Val Pro Gly Gly Asn Leu Gly Asn
                325                 330                 335
Ile Tyr Ala Phe Tyr Lys Gly Phe Lys Met Cys Gln Glu Leu Gly Leu
                340                 345                 350
Val Asp Lys Ile Pro Arg Leu Val Cys Ala Gln Ala Ala Asn Ala Asp
                355                 360                 365
Pro Leu Tyr Leu Tyr Phe Lys Ser Gly Trp Lys Glu Phe Lys Pro Val
                370                 375                 380
Lys Ser Ser Thr Thr Phe Ala Ser Ala Ile Gln Ile Gly Asp Pro Val
385                 390                 395                 400
Ser Ile Asp Arg Ala Val His Ala Leu Lys Ser Cys Asp Gly Ile Val
                405                 410                 415
Glu Glu Ala Thr Glu Glu Glu Leu Met Asp Ala Thr Ala Gln Ala Asp
                420                 425                 430
```

```
Ser Thr Gly Met Phe Ile Cys Pro His Thr Gly Val Ala Leu Thr Ala
        435                 440                 445
Leu Phe Lys Leu Arg Asn Ser Gly Leu Ile Lys Ala Thr Asp Arg Thr
    450                 455                 460
Val Val Val Ser Thr Ala His Gly Leu Lys Phe Thr Gln Ser Lys Ile
465                 470                 475                 480
Asp Tyr His Ser Lys Asp Ile Lys Asp Met Ala Cys Arg Tyr Ala Asn
                485                 490                 495
Pro Pro Met Gln Val Lys Ala Asp Phe Gly Ser Val Met Asp Val Leu
            500                 505                 510
Lys Thr Tyr Leu Gln Ser Lys Thr His
        515                 520

<210> SEQ ID NO 52
<211> LENGTH: 1876
<212> TYPE: DNA
<213> ORGANISM: Triticum aestivum

<400> SEQUENCE: 52
gcacgaggcg acacccgccg ccaccacctc ctcgctctcc ctcctcttcg cccacccccca     60
cttccaccac ccctccacca agcagcgcct cgacaggtcc catctccgcc tcccgctccg    120
cgccgccgcg caccgcacgc gctgcgccac cgagggcgcc tcggcgtcga ccgccaccaa    180
gcaccggcgc cccgcggagg agaacatcag ggaggaggcc gcgcgcctcc gcgggcccgc    240
cacgaccttc tcggcgtggt acgagccgtt cccccccggcc tccgatggcg accccaacga    300
gcgctactcg ctcgacgagg tcgtctaccg ctccacctcc ggcggcctcc tcgacgtccg    360
ccacgacatg gacgcgctcg cgcgcttccc gggctcctac tggcgcgacc tcttcgactc    420
ccgcgtcggc cgcaccacct ggccctacgg ctccggcgtc tggtccaaga aggagttcgt    480
gctcccggag atcgactccg accacatcgt ctctctcttc gagggcaaca gcaacctctt    540
ctgggcggag cgcctcggcc gcgagcacct cggcgggatg aatgacctct gggtcaagca    600
gtgcggcatc tcgcacactg gctccttcaa ggacctcggc atgacggcgc tcgtcagcca    660
ggtcaatcgc ctccgccggg ctccgctctc gcgcccatc aacggcgtgg ggtgcgcgtc    720
cactggcgac acctccgccg cgctctcggc ctactgtgcc gctgcgggca tccccgccat    780
cgtgttcctc cccgcagacc gcatctcgct gcagcagctc atccagccca tcgccaacgg    840
cgccacggtg ctctcgcttg acaccgattt cgacggatgc atgcggctta tcagggaggt    900
gacagctgag ctgcccatat acctcgcaaa ctcactcaac tcgcttcggc tggagggggca    960
gaagactgca gccatagaga tattgcaaca gttcaattgg caggtgccgg actgggtcat   1020
tatcccagga ggcaatctgg gcaacattta tgctttctac aaggggtttg agatgtgccg   1080
tgctcttggg ctagttgatc gtgttccacg gcttgtatgt gcacaggctg ccaatgcaaa   1140
tccactgtac cggtattaca gtctgggtg gactgacttc caatcacttg ttgctggaac   1200
tacatttgca tctgccatac agattggtga tccagtatct attgaccgtg cggttgttgc   1260
gctgaaggca accgatggca ttgttgagga agctacagag gaggagctta tggatgcgac   1320
ggctcttgct gacctcactg ggatgtttgc ttgcccacat actggggttg cacttgctgc   1380
cctgttcaag ctccgtgacc agggtatgat tggcactaat gaccgcacgg tggttgttag   1440
tacagcacac gggctaaagt tcacacaatc aaagatcgac taccatgata agaacatcaa   1500
ggacatgttg tgccagtatg ccaatccacc gatcagtgtg aagcctgact ttgggtctgt   1560
catggatgtt ctccagaaga agctcaatgg taagatctga gcttaccttt aattaacctc   1620
```

```
aagagttcta tcttgtttat cgtcacaacg gctgtacttt ggcatcttaa tcaactgcac    1680
ttggtgacca tggtatggcg atatcatctt tattttccag tactaggttc ttgaggctct    1740
tctaactata ggcaaaagtg gatagagctt tccttgtact ttatctgtat catgtaatag    1800
caataataat gtatgatgtt atggttgaat aattgtttgg ttcagccaaa aaaaaaaaaa    1860
aaaaaaaaaa aaaaa                                                     1876

<210> SEQ ID NO 53
<211> LENGTH: 532
<212> TYPE: PRT
<213> ORGANISM: Triticum aestivum

<400> SEQUENCE: 53

His Glu Ala Thr Pro Ala Ala Thr Thr Ser Ser Leu Ser Leu Leu Phe
 1               5                  10                  15

Ala His Pro His Phe His His Pro Ser Thr Lys Gln Arg Leu Asp Arg
            20                  25                  30

Ser His Leu Arg Leu Pro Leu Arg Ala Ala Ala His Arg Thr Arg Cys
        35                  40                  45

Ala Thr Glu Gly Ala Ser Ala Ser Thr Ala Thr Lys His Arg Arg Pro
    50                  55                  60

Ala Glu Glu Asn Ile Arg Glu Ala Ala Arg Leu Arg Gly Pro Ala
65                  70                  75                  80

Thr Thr Phe Ser Ala Trp Tyr Glu Pro Phe Pro Ala Ser Asp Gly
                85                  90                  95

Asp Pro Asn Glu Arg Tyr Ser Leu Asp Glu Val Val Tyr Arg Ser Thr
            100                 105                 110

Ser Gly Gly Leu Leu Asp Val Arg His Asp Met Asp Ala Leu Ala Arg
        115                 120                 125

Phe Pro Gly Ser Tyr Trp Arg Asp Leu Phe Asp Ser Arg Val Gly Arg
    130                 135                 140

Thr Thr Trp Pro Tyr Gly Ser Gly Val Trp Ser Lys Lys Glu Phe Val
145                 150                 155                 160

Leu Pro Glu Ile Asp Ser Asp His Ile Val Ser Leu Phe Glu Gly Asn
                165                 170                 175

Ser Asn Leu Phe Trp Ala Glu Arg Leu Gly Arg Glu His Leu Gly Gly
            180                 185                 190

Met Asn Asp Leu Trp Val Lys Gln Cys Gly Ile Ser His Thr Gly Ser
        195                 200                 205

Phe Lys Asp Leu Gly Met Thr Ala Leu Val Ser Gln Val Asn Arg Leu
    210                 215                 220

Arg Arg Ala Pro Leu Ser Arg Pro Ile Asn Gly Val Gly Cys Ala Ser
225                 230                 235                 240

Thr Gly Asp Thr Ser Ala Ala Leu Ser Ala Tyr Cys Ala Ala Ala Gly
                245                 250                 255

Ile Pro Ala Ile Val Phe Leu Pro Ala Asp Arg Ile Ser Leu Gln Gln
            260                 265                 270

Leu Ile Gln Pro Ile Ala Asn Gly Ala Thr Val Leu Ser Leu Asp Thr
        275                 280                 285

Asp Phe Asp Gly Cys Met Arg Leu Ile Arg Glu Val Thr Ala Glu Leu
    290                 295                 300

Pro Ile Tyr Leu Ala Asn Ser Leu Asn Ser Leu Arg Leu Glu Gly Gln
305                 310                 315                 320
```

-continued

```
Lys Thr Ala Ala Ile Glu Ile Leu Gln Gln Phe Asn Trp Gln Val Pro
                325                 330                 335

Asp Trp Val Ile Ile Pro Gly Gly Asn Leu Gly Asn Ile Tyr Ala Phe
                340                 345                 350

Tyr Lys Gly Phe Glu Met Cys Arg Ala Leu Gly Leu Val Asp Arg Val
            355                 360                 365

Pro Arg Leu Val Cys Ala Gln Ala Ala Asn Ala Asn Pro Leu Tyr Arg
        370                 375                 380

Tyr Tyr Lys Ser Gly Trp Thr Asp Phe Gln Ser Leu Val Ala Gly Thr
385                 390                 395                 400

Thr Phe Ala Ser Ala Ile Gln Ile Gly Asp Pro Val Ser Ile Asp Arg
                405                 410                 415

Ala Val Val Ala Leu Lys Ala Thr Asp Gly Ile Val Glu Glu Ala Thr
                420                 425                 430

Glu Glu Glu Leu Met Asp Ala Thr Ala Leu Ala Asp Leu Thr Gly Met
            435                 440                 445

Phe Ala Cys Pro His Thr Gly Val Ala Leu Ala Ala Leu Phe Lys Leu
        450                 455                 460

Arg Asp Gln Gly Met Ile Gly Thr Asn Asp Arg Thr Val Val Val Ser
465                 470                 475                 480

Thr Ala His Gly Leu Lys Phe Thr Gln Ser Lys Ile Asp Tyr His Asp
                485                 490                 495

Lys Asn Ile Lys Asp Met Leu Cys Gln Tyr Ala Asn Pro Pro Ile Ser
                500                 505                 510

Val Lys Pro Asp Phe Gly Ser Val Met Asp Val Leu Gln Lys Lys Leu
            515                 520                 525

Asn Gly Lys Ile
        530

<210> SEQ ID NO 54
<211> LENGTH: 525
<212> TYPE: PRT
<213> ORGANISM: Oryza sativa

<400> SEQUENCE: 54

Met Ala Thr Ala Thr Ala Ser Ser Leu Ser Leu Leu Phe Ala His Pro
  1               5                  10                  15

His Ser Ser Asn Pro Arg Pro Phe Ala Gly Gly Pro His Leu Arg Arg
                 20                  25                  30

Pro Leu Arg Ala Ala Pro His Arg Ala Arg Cys Ala Ser Asp Ala Ala
             35                  40                  45

Thr Thr Ala Thr Arg His Arg Arg Pro Ala Glu Glu Asn Ile Arg Glu
         50                  55                  60

Glu Ala Ala Arg Leu Arg Gly Pro Gly Asn Asp Phe Ser Ala Trp Tyr
 65                  70                  75                  80

Val Pro Phe Pro Pro Thr Pro Glu Asp Asp Pro Asp Glu Arg Tyr Ser
                 85                  90                  95

Leu Asp Glu Val Val Tyr Arg Ser Ser Ser Gly Gly Leu Leu Asp Val
                100                 105                 110

Cys His Asp Met Glu Ala Leu Ala Arg Phe Pro Gly Ser Tyr Trp Arg
            115                 120                 125

Asp Leu Phe Asp Ser Arg Val Gly Arg Thr Ala Trp Pro Tyr Gly Ser
        130                 135                 140

Gly Val Trp Ser Lys Lys Glu Phe Val Leu Pro Glu Ile Asp Ser Asp
145                 150                 155                 160
```

His Ile Val Ser Leu Phe Glu Gly Asn Ser Asn Leu Phe Trp Ala Glu
            165                 170                 175

Arg Leu Gly Arg Glu His Leu Gly Gly Met Thr Asp Leu Trp Val Lys
        180                 185                 190

His Cys Gly Ile Ser His Thr Gly Ser Phe Lys Asp Leu Gly Met Thr
    195                 200                 205

Val Leu Val Ser Gln Val Asn Arg Leu Arg Arg Ala Pro Leu Ser Arg
    210                 215                 220

Pro Ile Asn Gly Val Gly Cys Ala Ser Thr Gly Asp Thr Ser Ala Ala
225                 230                 235                 240

Leu Ser Ala Tyr Cys Ala Ala Ala Gly Ile Pro Ala Ile Val Phe Leu
            245                 250                 255

Pro Ala Asp Arg Ile Ser Leu Gln Gln Leu Ile Gln Pro Ile Ala Asn
        260                 265                 270

Gly Ala Thr Val Leu Ser Leu Asp Thr Asp Phe Asp Gly Cys Met Arg
    275                 280                 285

Leu Ile Arg Glu Val Thr Ala Glu Leu Pro Ile Tyr Leu Ala Asn Ser
    290                 295                 300

Leu Asn Ser Leu Arg Leu Glu Gly Gln Lys Thr Ala Ile Glu Ile
305                 310                 315                 320

Leu Gln Gln Phe Asp Trp Gln Val Pro Asp Trp Val Ile Val Pro Gly
            325                 330                 335

Gly Asn Leu Gly Asn Ile Tyr Ala Phe Tyr Lys Gly Phe Glu Met Cys
        340                 345                 350

Arg Val Leu Gly Leu Val Asp Arg Val Pro Arg Leu Val Cys Ala Gln
    355                 360                 365

Ala Ala Asn Ala Asn Pro Leu Tyr Arg Phe Tyr Lys Ser Gly Trp Thr
    370                 375                 380

Asp Phe Gln Pro Arg Val Ala Glu Thr Thr Phe Ala Ser Ala Ile Gln
385                 390                 395                 400

Ile Gly Asp Pro Val Ser Val Asp Arg Ala Val Val Ala Leu Lys Ala
            405                 410                 415

Thr Asp Gly Ile Val Glu Glu Ala Thr Glu Glu Leu Met Asp Ala
        420                 425                 430

Met Ser Leu Ala Asp Arg Thr Gly Met Phe Ala Cys Pro His Thr Gly
    435                 440                 445

Val Ala Leu Ala Ala Leu Phe Lys Leu Arg Asp Gln Arg Ile Ile Gly
    450                 455                 460

Pro Asn Asp Arg Thr Val Val Ser Thr Ala His Gly Leu Lys Phe
465                 470                 475                 480

Thr Gln Ser Lys Ile Asp Tyr His Asp Arg Asn Ile Lys Asp Met Leu
            485                 490                 495

Cys Gln Tyr Ala Asn Pro Pro Ile Asn Val Lys Ala Asp Phe Ala Ser
        500                 505                 510

Val Met Asp Val Leu Gln Asn Lys Leu Asn Gly Lys Ile
    515                 520                 525

<210> SEQ ID NO 55
<211> LENGTH: 519
<212> TYPE: PRT
<213> ORGANISM: Solanum tuberosum

<400> SEQUENCE: 55

Met Ala Ala Ser Cys Met Leu Arg Ser Ser Phe Ile Ser Pro Gly Leu

-continued

```
  1               5                  10                 15
Pro Gln Leu His His Gln Ser Thr Ser Lys Pro Asn Asn Gly Ile His
             20                  25                 30

Phe Phe Thr Pro Ile Lys Ala Thr Ala Thr Asn Asp Ala Ile Ser Gln
             35                  40                 45

Gln Lys His Arg Arg Pro Ala Asp Glu Asn Ile Arg Glu Glu Ala Arg
             50                  55                 60

Arg His Cys Ser Ser His Asn Phe Ser Ala Arg Tyr Val Pro Phe Asn
65                       70                  75                 80

Ala Gly Pro Asn Ser Asp Glu Trp Tyr Ser Leu Asp Glu Ile Val Tyr
                     85                  90                 95

Arg Ser Arg Ser Gly Gly Leu Leu Asp Val Gln His Asp Met Asp Ala
             100                 105                110

Leu Lys Lys Phe Asp Gly Gln Tyr Trp Arg Ser Leu Phe Asp Ser Arg
             115                 120                125

Val Gly Lys Thr Thr Trp Pro Tyr Gly Ser Gly Val Trp Ser Lys Lys
             130                 135                140

Glu Trp Val Leu Pro Glu Ile Asp Ser Asp Ile Val Ser Ala Phe
145                  150                 155                160

Glu Gly Asn Ser Asn Leu Phe Trp Ala Glu Arg Phe Gly Lys Gln Phe
                     165                 170                175

Leu Gly Met Thr Asp Leu Trp Val Lys His Cys Gly Ile Ser His Thr
                     180                 185                190

Gly Ser Phe Lys Asp Leu Gly Met Thr Val Leu Val Ser Gln Val Asn
             195                 200                205

Arg Leu Arg Lys Met His Lys Pro Val Val Gly Val Gly Cys Ala Ser
             210                 215                220

Thr Gly Asp Thr Ser Ala Ala Leu Ser Ala Tyr Cys Ala Ser Ala Gly
225                  230                 235                240

Ile Pro Ser Ile Val Phe Leu Pro Ala Asn Lys Ile Ser Met Ala Gln
                     245                 250                255

Leu Val Gln Pro Ile Ala Asn Gly Ala Phe Val Leu Ser Ile Asp Thr
                     260                 265                270

Asp Phe Asp Gly Cys Met Gln Leu Ile Arg Glu Val Thr Ala Glu Leu
             275                 280                285

Pro Ile Tyr Leu Ala Asn Ser Leu Asn Ser Leu Arg Leu Glu Gly Gln
             290                 295                300

Lys Thr Ala Ala Ile Glu Ile Leu Gln Gln Phe Asp Trp Glu Val Pro
305                  310                 315                320

Glu Trp Val Ile Val Pro Gly Gly Asn Leu Gly Asn Ile Tyr Ala Phe
                     325                 330                335

Tyr Lys Gly Phe Gln Met Cys Lys Glu Leu Gly Leu Val Asp Arg Ile
                     340                 345                350

Pro Arg Leu Val Cys Ala Gln Ala Ala Asn Ala Asn Pro Leu Tyr Leu
             355                 360                365

His Tyr Lys Ser Gly Trp Lys Asp Phe Lys Pro Val Lys Ala Asn Thr
             370                 375                380

Thr Phe Ala Ser Ala Ile Gln Ile Gly Asp Pro Val Ser Ile Asp Arg
385                  390                 395                400

Ala Val Phe Ala Leu Gln Gln Cys Asn Gly Ile Val Glu Glu Ala Thr
                     405                 410                415

Glu Glu Glu Leu Met Asp Ala Met Ala Gln Ala Asp Ser Thr Gly Met
             420                 425                430
```

```
Phe Ile Cys Pro His Thr Gly Val Ala Leu Thr Ala Leu Phe Lys Leu
        435                 440                 445
Arg Asn Ser Gly Val Ile Ala Pro Thr Asp Arg Thr Val Val Val Ser
    450                 455                 460
Thr Ala His Gly Leu Lys Phe Thr Gln Ser Lys Ile Asp Tyr His Ser
465                 470                 475                 480
Lys Glu Ile Lys Asp Met Glu Cys Arg Phe Ala Asn Pro Pro Val Glu
                485                 490                 495
Val Lys Ala Asp Phe Gly Ser Val Met Asp Val Leu Lys Ser Tyr Leu
            500                 505                 510
Leu Ser Gln Asn Ser Lys Leu
        515

<210> SEQ ID NO 56
<211> LENGTH: 1812
<212> TYPE: DNA
<213> ORGANISM: Zea mays

<400> SEQUENCE: 56
gcacgagtcg gccttcccca ctgtactctc caatctcgcc gccaagcctc accgcaccat      60
ggcgaccttc accgcggcct cctccctctc cctcctcttc tcccacccgc actcccactc     120
ccgccaacca tccgcccagg ggcccaccgc cagctcccac ctccacctgc atccgcgcgc     180
cagccgcgcg cgctgcgcct cttctgcgtg gtacgagccc ttcccgccgg cgcccggcgg     240
cgacccgaac gagcgctact cgctggacga ggtcgtctac cgctccagct cgggggggcct     300 cctcgacgtg cgccacgaca tggaggcgct ggcccgctac ccggggtcct actggcgtga     360
cctcttcgac tcccgcgtcg gccgcaccgc ctggccctac ggctcgggcg tctggtccaa     420
gaaggagttc gtgctccccg agatcgactc cgaccacatc gtctccctct cgagggcaa     480 ctccaacctc ttctgggcgg agcgcctcgg ccgcagcacc ctcggcggga tgaacgacct     540
ctgggtcaag cactgtggca tctcccacac gggctccttc aaggacctcg gcatgacggt     600
gctcgtcagc caggtgaacc gcctccgccg cgcgccgctc tcgcgcccca tcgccggtgt     660
cggctgcgcg tccacgggag acacctccgc cgcgctctcg gcctactgcg cagccgcggg     720
aatccccgcc atcgtgttcc tgccagcgga ccgcatctcg ctgcagcagc tcatccagcc     780
gatcgccaac ggcgccaccg tgctctctct agacactgat tttgatggct gcatgcggct     840
cattcgcgag gtcactgcag agctgccaat ctaccttgcc aattcgctca acccgctccg     900
ccttgagggg cagaagacag cggccatcga gatattgcag cagttcaatt ggcaggtgcc     960
agattgggtc attgttccag gaggcaatct tgggaatatc tatgcattct acaaggggtt    1020
tgagatgtgc cgcgttcttg gacttgttga tcgcgtgcca cggcttgtct gcgcacaggc    1080
tgcaaatgca aatccattgt accggtacta caagtcaggt tggactgagt ttgagccaca    1140
aactgccgag actacatttg catctgcgat acagattggt gatcctgtat ctgttgaccg    1200
tgcggtggtc gcgctgaagg ccactgacgg tattgtggag gaggctacag aggaggagct    1260
aatggatgca acggcgcttg ctgaccgcac tgggatgttt gcttgcccac atactggggt    1320
tgcacttgct gctttgttta agcttcaggg tcagcgtata attggcccta atgaccgcac    1380
tgtggttgtt agcacagctc atgggctgaa gttcacgcag tcaaagattg actaccatga    1440
caaaaacatc aaagacatgg tttgccagta tgctaatcca ccgatcagtg tgaaggctga    1500 cttttggttct gtgatggatg ttctccagaa aaatctcaat ggtaagatat aaagttatat    1560
```

-continued

```
gattaattaa ccctccaaac tgttttttt tgttttttcg ttccaggaat tttattcctg    1620
agtctttcaa ctttgtttgg tgaacatggt atggtgctaa atctagacc taataccttg    1680 tagtactagt tctggaggct cttttggttg taggtcgaag tggatagagc tgttccttgt    1740
actttatctg tttcatgtaa tatgaataat aaattatggt ctaaatattt gaataaaaaa    1800
aaaaaaaaaa aa                                                        1812
```

<210> SEQ ID NO 57
<211> LENGTH: 497
<212> TYPE: PRT
<213> ORGANISM: Zea mays

<400> SEQUENCE: 57

```
Met Ala Thr Phe Thr Ala Ala Ser Ser Leu Ser Leu Leu Phe Ser His
1               5                   10                  15

Pro His Ser His Ser Arg Gln Pro Ser Ala Gln Gly Pro Thr Ala Ser
            20                  25                  30

Ser His Leu His Leu His Pro Arg Ala Ser Arg Ala Arg Cys Ala Ser
        35                  40                  45

Ser Ala Trp Tyr Glu Pro Phe Pro Pro Ala Pro Gly Gly Asp Pro Asn
    50                  55                  60

Glu Arg Tyr Ser Leu Asp Glu Val Val Tyr Arg Ser Ser Ser Gly Gly
65                  70                  75                  80

Leu Leu Asp Val Arg His Asp Met Glu Ala Leu Ala Arg Tyr Pro Gly
                85                  90                  95

Ser Tyr Trp Arg Asp Leu Phe Asp Ser Arg Val Gly Arg Thr Ala Trp
            100                 105                 110

Pro Tyr Gly Ser Gly Val Trp Ser Lys Lys Glu Phe Val Leu Pro Glu
        115                 120                 125

Ile Asp Ser Asp His Ile Val Ser Leu Phe Glu Gly Asn Ser Asn Leu
    130                 135                 140

Phe Trp Ala Glu Arg Leu Gly Arg Glu His Leu Gly Gly Met Asn Asp
145                 150                 155                 160

Leu Trp Val Lys His Cys Gly Ile Ser His Thr Gly Ser Phe Lys Asp
                165                 170                 175

Leu Gly Met Thr Val Leu Val Ser Gln Val Asn Arg Leu Arg Arg Ala
            180                 185                 190

Pro Leu Ser Arg Pro Ile Ala Gly Val Gly Cys Ala Ser Thr Gly Asp
        195                 200                 205

Thr Ser Ala Ala Leu Ser Ala Tyr Cys Ala Ala Ala Gly Ile Pro Ala
    210                 215                 220

Ile Val Phe Leu Pro Ala Asp Arg Ile Ser Leu Gln Gln Leu Ile Gln
225                 230                 235                 240

Pro Ile Ala Asn Gly Ala Thr Val Leu Ser Leu Asp Thr Asp Phe Asp
                245                 250                 255

Gly Cys Met Arg Leu Ile Arg Glu Val Thr Ala Glu Leu Pro Ile Tyr
            260                 265                 270

Leu Ala Asn Ser Leu Asn Pro Leu Arg Leu Glu Gly Gln Lys Thr Ala
        275                 280                 285

Ala Ile Glu Ile Leu Gln Gln Phe Asn Trp Gln Val Pro Asp Trp Val
    290                 295                 300

Ile Val Pro Gly Gly Asn Leu Gly Asn Ile Tyr Ala Phe Tyr Lys Gly
305                 310                 315                 320

Phe Glu Met Cys Arg Val Leu Gly Leu Val Asp Arg Val Pro Arg Leu
```

```
                    325                 330                 335
Val Cys Ala Gln Ala Ala Asn Ala Asn Pro Leu Tyr Arg Tyr Tyr Lys
            340                 345                 350

Ser Gly Trp Thr Glu Phe Glu Pro Gln Thr Ala Glu Thr Thr Phe Ala
        355                 360                 365

Ser Ala Ile Gln Ile Gly Asp Pro Val Ser Val Asp Arg Ala Val Val
    370                 375                 380

Ala Leu Lys Ala Thr Asp Gly Ile Val Glu Glu Ala Thr Glu Glu Glu
385                 390                 395                 400

Leu Met Asp Ala Thr Ala Leu Ala Asp Arg Thr Gly Met Phe Ala Cys
                405                 410                 415

Pro His Thr Gly Val Ala Leu Ala Ala Leu Phe Lys Leu Gln Gly Gln
            420                 425                 430

Arg Ile Ile Gly Pro Asn Asp Arg Thr Val Val Ser Thr Ala His
        435                 440                 445

Gly Leu Lys Phe Thr Gln Ser Lys Ile Asp Tyr His Asp Lys Asn Ile
    450                 455                 460

Lys Asp Met Val Cys Gln Tyr Ala Asn Pro Pro Ile Ser Val Lys Ala
465                 470                 475                 480

Asp Phe Gly Ser Val Met Asp Val Leu Gln Lys Asn Leu Asn Gly Lys
                485                 490                 495

Ile

<210> SEQ ID NO 58
<211> LENGTH: 1763
<212> TYPE: DNA
<213> ORGANISM: Zea mays

<400> SEQUENCE: 58
gcacgagccc actctgccgc cgccagcttg cccaccatgg cggccgccgc ctccatgtcg      60
ttcctcctct cccaccccca gtcgcgctct gccaccccaa gccgccacct cccgctccgt     120
ccggcagccc gccgcgtccg gtgcgccacc gacgccgccg ccctttccgc gtggtacgag     180
cccttcccgc cggccccgaa cggcgacccc aacgagcgct actccctgga cgagatcgtg     240
taccggtcca gctcgggggg cctcctcgac gtgcggcacg acatggaggc gctgtcccgc     300
ttctcgggcg cctactggcg cgacctcttc gactcccgca tcgggcgcac cacctggccg     360
tacgggtccg gcgtgtggtc caagaaggag ttcgtgctcc ccgagatcga gcccgaccac     420
atcgtctccc tgttcgaggg caactcgaac ctgttctggg ccgagcggct cgggcgcgac     480
cacctcggcg ggatgaacga cctgtgggtg aagcactgcg gcatctccca cacggggtcg     540
ttcaaggacc tcggcatgac cgtgctggtg agccaggtga accggctccg ccgcgcgccg     600
ctgtcgcgcc ccatcgccgg cgtcgggtgc gcgtccacgg gggacacctc ggccgcgctc     660
tccgcctact cgcgccgccg cgggatcccg gccatcgtct tcctccccgc caaccgcatc     720
tcgctggagc agctcatcca gcccatcgcc aacggcgcca ccgtgctctc gctcgacacc     780
gacttcgacg gtgcatgcg gctcatcagg gaggtgaccg ccgagctgcc tatctacctc     840
gccaactcgc tcaactccct ccgcctcgag gggcagaaga cggcggccat cgagatactg     900
cagcagttcg actgggaggt gcccgactgg gtgatcgtgc cggaggcaa cctgggaac     960 atatacgcct tctacaaggg gttcgagatg tgccgtgtcc tcgggctcgt cgaccgcgtg    1020
ccgcggctcg tctgcgcgca ggcggccaac gcgaacccgc tctacggcta ctacaagaca    1080
ggctggaccg agttccagcc gcaggtggcc aggccgacgt tcgcgtcagc gatccagatc    1140
```

```
ggcgacccgg tgtccgtcga ccgggccgtg gtcgcgctca aggcgacgga cggcattgtc    1200
gaggaggcga cggaggaaga gctcatgaac gcgatgtcgc tcgccgaccg cacggggatg    1260
ttcgcttgcc cgcacaccgg ggtcgcgctc gccgccctgt tcaagctcag ggaccagcgc    1320
gtcatcggga cgaacgaccg caccgtggtc gtcagcacgg ctcacggcct caagttctcg    1380
cagtcgaaga tcgactacca tgacagcaag atcgaggaca tggcttgcaa gtactccaac    1440
ccgcctgtga gcgtgaaggc cgactttggc gccgtcatgg atgtgctgaa gagaggctc     1500 aagggcaagc tctgagcgcc tgtgcctggc taatgcaatc aactgattgg aatgcagtgg    1560
tttcgtcggt atcgggggt cttttaggct tcagaaattc tgtctgggtt agactatctg     1620
tttgtggagt ttagcaggag aatggatatc tctcctgcaa gactggcgct ctctattgtg    1680
ctacgatgtg ttaccatgga taataagtga cctagttgct gttggattga aaaaaaaaa     1740 aaaaaaaaaa aaaaaaaaaa aaa                                            1763
```

<210> SEQ ID NO 59
<211> LENGTH: 492
<212> TYPE: PRT
<213> ORGANISM: Zea mays

<400> SEQUENCE: 59

```
Met Ala Ala Ala Ala Ser Met Ser Phe Leu Leu Ser His Pro Gln Ser
 1               5                  10                  15

Arg Ser Ala Thr Pro Ser Arg His Leu Pro Leu Arg Pro Ala Ala Arg
            20                  25                  30

Arg Val Arg Cys Ala Thr Asp Ala Ala Leu Ser Ala Trp Tyr Glu
        35                  40                  45

Pro Phe Pro Ala Pro Asn Gly Asp Pro Asn Glu Arg Tyr Ser Leu
    50                  55                  60

Asp Glu Ile Val Tyr Arg Ser Ser Gly Gly Leu Leu Asp Val Arg
 65                  70                  75                  80

His Asp Met Glu Ala Leu Ser Arg Phe Ser Gly Ala Tyr Trp Arg Asp
                85                  90                  95

Leu Phe Asp Ser Arg Ile Gly Arg Thr Thr Trp Pro Tyr Gly Ser Gly
            100                 105                 110

Val Trp Ser Lys Lys Glu Phe Val Leu Pro Glu Ile Glu Pro Asp His
        115                 120                 125

Ile Val Ser Leu Phe Glu Gly Asn Ser Asn Leu Phe Trp Ala Glu Arg
    130                 135                 140

Leu Gly Arg Asp His Leu Gly Gly Met Asn Asp Leu Trp Val Lys His
145                 150                 155                 160

Cys Gly Ile Ser His Thr Gly Ser Phe Lys Asp Leu Gly Met Thr Val
                165                 170                 175

Leu Val Ser Gln Val Asn Arg Leu Arg Arg Ala Pro Leu Ser Arg Pro
            180                 185                 190

Ile Ala Gly Val Gly Cys Ala Ser Thr Gly Asp Thr Ser Ala Ala Leu
        195                 200                 205

Ser Ala Tyr Cys Ala Ala Ala Gly Ile Pro Ala Ile Val Phe Leu Pro
    210                 215                 220

Ala Asn Arg Ile Ser Leu Glu Gln Leu Ile Gln Pro Ile Ala Asn Gly
225                 230                 235                 240

Ala Thr Val Leu Ser Leu Asp Thr Asp Phe Asp Gly Cys Met Arg Leu
                245                 250                 255
```

-continued

```
Ile Arg Glu Val Thr Ala Glu Leu Pro Ile Tyr Leu Ala Asn Ser Leu
            260                 265                 270
Asn Ser Leu Arg Leu Glu Gly Gln Lys Thr Ala Ala Ile Glu Ile Leu
        275                 280                 285
Gln Gln Phe Asp Trp Glu Val Pro Asp Trp Val Ile Val Pro Gly Gly
    290                 295                 300
Asn Leu Gly Asn Ile Tyr Ala Phe Tyr Lys Gly Phe Glu Met Cys Arg
305                 310                 315                 320
Val Leu Gly Leu Val Asp Arg Val Pro Arg Leu Val Cys Ala Gln Ala
                325                 330                 335
Ala Asn Ala Asn Pro Leu Tyr Gly Tyr Tyr Lys Thr Gly Trp Thr Glu
            340                 345                 350
Phe Gln Pro Gln Val Ala Arg Pro Thr Phe Ala Ser Ala Ile Gln Ile
        355                 360                 365
Gly Asp Pro Val Ser Val Asp Arg Ala Val Val Ala Leu Lys Ala Thr
    370                 375                 380
Asp Gly Ile Val Glu Glu Ala Thr Glu Glu Leu Met Asn Ala Met
385                 390                 395                 400
Ser Leu Ala Asp Arg Thr Gly Met Phe Ala Cys Pro His Thr Gly Val
                405                 410                 415
Ala Leu Ala Ala Leu Phe Lys Leu Arg Asp Gln Arg Val Ile Gly Thr
            420                 425                 430
Asn Asp Arg Thr Val Val Ser Thr Ala His Gly Leu Lys Phe Ser
        435                 440                 445
Gln Ser Lys Ile Asp Tyr His Asp Ser Lys Ile Glu Asp Met Ala Cys
    450                 455                 460
Lys Tyr Ser Asn Pro Pro Val Ser Val Lys Ala Asp Phe Gly Ala Val
465                 470                 475                 480
Met Asp Val Leu Lys Lys Arg Leu Lys Gly Lys Leu
                485                 490
```

<210> SEQ ID NO 60
<211> LENGTH: 2219
<212> TYPE: DNA
<213> ORGANISM: Glycine max

<400> SEQUENCE: 60

```
gtcgcggcgg cggctggcaa gtagtagtat taaaaaagtt gatgggataa ttggcattgg      60
ttgagtttgg ttcaaattga gaaaatcatt actccattaa ccattcattc accaatcctc     120
catggcttcc tcttctctgt ttcagtctct cccttctct ctccaaacct ctaaaccta       180
cgcgcctccc aaacccgccg cccacttcgt tgtccgcgcc caatcccccc tcactcagaa     240
cgccaagtac gtccccttca cgccgactc ctcctcctcc tcctccacgg agtcctactc      300
gctcgacgag atcgtctacc gctcccaatc cggcggcctc ctggacgtcc agcacgacat     360
ggatgccctc aagcgtttcg acggcgagta ctggcgcaac ctcttcgact cgcgcgtggg     420
caaaaccacc tggccttacg gctccggcgt ctggagcaaa aaagaatggg tcctccccga     480
gatccacgac gacgatatcg tctccgcctt cgagggtaac tccaacctct tctgggccga     540
gcgtttcggc aaacagttcc tcggcatgaa cgatttgtgg gtcaaacact gcggaatcag     600
ccacacgggc agcttcaagg atctcggcat gaccgtcctc gtcagccagg tcaatcgctt     660
gagaaaaatg aaccgccccg tcgtcggtgt tggttcgcc tccaccggtg acacatcggc      720
cgctttatcc gcctattgcg cttccgctgc cattccttcc attgtgtttt tgcctgctaa     780
```

-continued

```
taaaatctct cttgcccaac ttgttcagcc tattgccaat ggagcctttg tgttgagtat    840
cgacactgat tttgatggtt gcatgcagtt gatcagagaa gtcactgctg aattgcctat    900
ttatttggct aactctctca acagtttgaa gttggaaggg cagaaaactg ctgctattga    960
gattctgcag cagtttgatt ggcaggttcc tgattgggtc attgtgcctg aagcaacct   1020
tggcaacatt tatgcctttt acaaggggtt taagatgttt caagagcttg gcttgtgga   1080
taagattcca aggcttgttt gtgctcaggc tgccaatgct gatcctttgt atttgtactt   1140
taaatccggg tggaaggagt ttaagcctgt gaagtcgagc actacatttg cttctgccat   1200
tcaaattggt gatcctgttt ccattgacag ggcggttcac gcgctaaaga gttgcgatgg   1260
gattgtggag gaggccacgg aggaggagtt gatggatgct acagcgcagg cggattctac   1320
tgggatgttt atttgccccc acaccgggt tgctttaact gcattgttta agctcaggaa   1380
cagcggggtt attaaggcca ctgataggac tgtggtggtt agcactgctc atggcttgaa   1440
gttcactcag tccaagattg attaccattc taaggacatc aaggacatgg cttgccgcta   1500
tgctaacccg cccatgcaag tgaaggcaga cttggctcg gttatggatg ttttgaagac   1560
gtatttgcag agtaaggctc attaggttag cattgcaagt tttgctcctc ctgagtttgc   1620
tcattattta cttacttta ggcactactg ctgtattgtc ttttctatga gctaggtttg   1680
agtgttgtaa taatttgctt gctgcattat gtatgccgtc tagtgttcca tattgggcat   1740
catccttagt atttgttgta gattttcttt gctgagcatt tgatataata gctcaagtag   1800
gaaaatgaat tgggtactat gaggaatgca tatcattggc ttgttattac tggattccag   1860
accaccccaa agaaaataa ttccaaaaaa tataattaga acaaatttcg tccttgttat   1920
gctgttggca ttaagctcag tgtgggtatt accaagcaac tcgaaatcaa gagaaaaaaa   1980
aattgacagc aaaggagctg cattgttgga ctgagtcaca tcacttcatt gctatgtcgt   2040
catatttcgt tgaattacgg gaaggcagca tgcacagcaa tatgcagcga ttaactgaag   2100
ccacaccgca cacattgaag tagtagtcaa tttagacact ccatcttgta ctttctacaa   2160
aaatgaattt ttcttagcca ttaagtataa tattttattc taaaaaaaaa aaaaaaaaa   2219
```

<210> SEQ ID NO 61
<211> LENGTH: 487
<212> TYPE: PRT
<213> ORGANISM: Glycine max

<400> SEQUENCE: 61

```
Met Ala Ser Ser Ser Leu Phe Gln Ser Leu Pro Phe Ser Leu Gln Thr
1               5                   10                  15

Ser Lys Pro Tyr Ala Pro Pro Lys Pro Ala Ala His Phe Val Arg
            20                  25                  30

Ala Gln Ser Pro Leu Thr Gln Asn Ala Lys Tyr Val Pro Phe Asn Ala
        35                  40                  45

Asp Ser Ser Ser Ser Ser Thr Glu Ser Tyr Ser Leu Asp Glu Ile
    50                  55                  60

Val Tyr Arg Ser Gln Ser Gly Leu Leu Asp Val Gln His Asp Met
65                  70                  75                  80

Asp Ala Leu Lys Arg Phe Asp Gly Glu Tyr Trp Arg Asn Leu Phe Asp
                85                  90                  95

Ser Arg Val Gly Lys Thr Thr Trp Pro Tyr Gly Ser Gly Val Trp Ser
            100                 105                 110

Lys Lys Glu Trp Val Leu Pro Glu Ile His Asp Asp Ile Val Ser
        115                 120                 125
```

```
Ala Phe Glu Gly Asn Ser Asn Leu Phe Trp Ala Glu Arg Phe Gly Lys
    130                 135                 140

Gln Phe Leu Gly Met Asn Asp Leu Trp Val Lys His Cys Gly Ile Ser
145                 150                 155                 160

His Thr Gly Ser Phe Lys Asp Leu Gly Met Thr Val Leu Val Ser Gln
                165                 170                 175

Val Asn Arg Leu Arg Lys Met Asn Arg Pro Val Val Gly Val Gly Cys
            180                 185                 190

Ala Ser Thr Gly Asp Thr Ser Ala Ala Leu Ser Ala Tyr Cys Ala Ser
        195                 200                 205

Ala Ala Ile Pro Ser Ile Val Phe Leu Pro Ala Asn Lys Ile Ser Leu
    210                 215                 220

Ala Gln Leu Val Gln Pro Ile Ala Asn Gly Ala Phe Val Leu Ser Ile
225                 230                 235                 240

Asp Thr Asp Phe Asp Gly Cys Met Gln Leu Ile Arg Glu Val Thr Ala
                245                 250                 255

Glu Leu Pro Ile Tyr Leu Ala Asn Ser Leu Asn Ser Leu Lys Leu Glu
            260                 265                 270

Gly Gln Lys Thr Ala Ala Ile Glu Ile Leu Gln Gln Phe Asp Trp Gln
        275                 280                 285

Val Pro Asp Trp Val Ile Val Pro Gly Ser Asn Leu Gly Asn Ile Tyr
    290                 295                 300

Ala Phe Tyr Lys Gly Phe Lys Met Phe Gln Glu Leu Gly Leu Val Asp
305                 310                 315                 320

Lys Ile Pro Arg Leu Val Cys Ala Gln Ala Ala Asn Ala Asp Pro Leu
                325                 330                 335

Tyr Leu Tyr Phe Lys Ser Gly Trp Lys Glu Phe Lys Pro Val Lys Ser
            340                 345                 350

Ser Thr Thr Phe Ala Ser Ala Ile Gln Ile Gly Asp Pro Val Ser Ile
        355                 360                 365

Asp Arg Ala Val His Ala Leu Lys Ser Cys Asp Gly Ile Val Glu Glu
    370                 375                 380

Ala Thr Glu Glu Glu Leu Met Asp Ala Thr Ala Gln Ala Asp Ser Thr
385                 390                 395                 400

Gly Met Phe Ile Cys Pro His Thr Gly Val Ala Leu Thr Ala Leu Phe
                405                 410                 415

Lys Leu Arg Asn Ser Gly Val Ile Lys Ala Thr Asp Arg Thr Val Val
            420                 425                 430

Val Ser Thr Ala His Gly Leu Lys Phe Thr Gln Ser Lys Ile Asp Tyr
        435                 440                 445

His Ser Lys Asp Ile Lys Asp Met Ala Cys Arg Tyr Ala Asn Pro Pro
    450                 455                 460

Met Gln Val Lys Ala Asp Phe Gly Ser Val Met Asp Val Leu Lys Thr
465                 470                 475                 480

Tyr Leu Gln Ser Lys Ala His
                485

<210> SEQ ID NO 62
<211> LENGTH: 1959
<212> TYPE: DNA
<213> ORGANISM: Glycine max

<400> SEQUENCE: 62
gcacgaggca taaagcatta ctccattcca cactgtcgat ggcttcctca tctcttttc          60
```

-continued

| | |
|---|---|
| agtctctccc tttctctctc aaaaccacta aaccctacgc gcttcccaaa cccgccgcca | 120 |
| atttcgtaat ccgcgcccaa tccccctca ctcagaacac caacgccgcc aaatacgtcc | 180 |
| ctttcaatgc cgaccctcc tcctccacga cggagtccta ctcgctcgac gagatcgtct | 240 |
| accgctccca atccggtggc ctcctcgacg tccagcacga catggacgcc ctcaagcgct | 300 |
| tcgacggcga gtactggcgc aacctcttcg actctcgcgt cggcaagacc acctggccct | 360 |
| acggctccgg cgtctggagc aaaaaagagt gggtcctccc tgagatccac gacgacgaca | 420 |
| tcgtctccgc cttcgaagga aactccaacc tcttctgggc cgagcgtttc ggcaaacagt | 480 |
| tcctcggcat gaacgatttg tgggtcaaac actgcggaat cagccacacc ggcagcttca | 540 |
| aggatctcgg catgaccgtc ctcgttagcc aggtcaaccg cttgagaaaa atgaatcgcc | 600 |
| ccgtcgtcgg tgtcggttgc gcctccaccg gtgacacctc cgccgcttta tctgcttatt | 660 |
| gcgcttcggc ggcgattcct tccattgtgt ttctgcctgc taataaaatc tcgcttgctc | 720 |
| aacttgttca gcctattgcc aatggtgcct ttgtgttgag tatcgacact gattttgatg | 780 |
| gttgcatgca gttgatcaga gaggtcactg ctgagttgcc tatttatttg gctaactctc | 840 |
| tcaacagttt gagattggaa gggcagaaaa ctgctgctat tgagattctg cagcagtttg | 900 |
| attggcaggt tcctgattgg gtcattgtgc ctggtggcaa ccttggcaac atttatgcct | 960 |
| tttacaaagg cttcaagatg tgtcaagagc ttggtcttgt ggataagatt ccaaggcttg | 1020 |
| tttgtgccca ggctgccaat gctgatcctt tgtatttgta cttaaatcc ggctggaagg | 1080 |
| agtttaagcc tgtgaagtca agcactacct ttgcctctgc cattcaaatt ggtgatcctg | 1140 |
| tttccatcga cagggcggtt cacgccctaa agagttgcga tgggatcgtg gaggaggcca | 1200 |
| ccgaggagga gttgatggat gctacggcgc aggcagattc cactgggatg tttatctgcc | 1260 |
| cccacactgg ggttgctttg actgctttgt ttaagctcag gaacagtggg cttattaagg | 1320 |
| ccactgatag gactgtggtg gttagcactg ctcatggcct caagttcact cagtccaaga | 1380 |
| tcgattacca ttctaaggac atcaaggaca tggcttgccg ctatgctaac cctcccatgc | 1440 |
| aagtcaaggc tgattttggg tcggttatgg atgttttgaa gacgtatttg cagagtaaga | 1500 |
| ctcattaggt tagcattgca acttttctc ctctcttcct gagtttgctg ctgattattt | 1560 |
| acttactatt attagccact tctactcctg tttttgtcttt tctataagct aggtttgagt | 1620 |
| attgtagtaa tttgcctgct gcattatgta tgctgtgctc catattgggg catcttagta | 1680 |
| tttgttgtag atttctttg ttgagcattt aatataatag ctcaagtaga aaaaaattaa | 1740 |
| ttggatacaa tgagggagga atgcacattg ttggcttgtt attactggat tccagaccag | 1800 |
| accacgccat ccccaaaaga aaataattcc aaaaatata attagaacag atttcttca | 1860 |
| ctttcatgtt atgctgttgg cattaagcta agtgtgggta ttaccaagca actctatgca | 1920 |
| atctgtgaca agtaattaaa tcaaaaaaaa aaaaaaaa | 1959 |

<210> SEQ ID NO 63
<211> LENGTH: 489
<212> TYPE: PRT
<213> ORGANISM: Glycine max

<400> SEQUENCE: 63

Met Ala Ser Ser Ser Leu Phe Gln Ser Leu Pro Phe Ser Leu Lys Thr
1               5                   10                  15

Thr Lys Pro Tyr Ala Leu Pro Lys Pro Ala Ala Asn Phe Val Ile Arg
            20                  25                  30

-continued

```
Ala Gln Ser Pro Leu Thr Gln Asn Thr Asn Ala Ala Lys Tyr Val Pro
         35                  40                  45

Phe Asn Ala Asp Pro Ser Ser Ser Thr Thr Glu Ser Tyr Ser Leu Asp
 50                  55                  60

Glu Ile Val Tyr Arg Ser Gln Ser Gly Gly Leu Leu Asp Val Gln His
 65                  70                  75                  80

Asp Met Asp Ala Leu Lys Arg Phe Asp Gly Glu Tyr Trp Arg Asn Leu
                 85                  90                  95

Phe Asp Ser Arg Val Gly Lys Thr Thr Trp Pro Tyr Gly Ser Gly Val
                100                 105                 110

Trp Ser Lys Lys Glu Trp Val Leu Pro Glu Ile His Asp Asp Ile
        115                 120                 125

Val Ser Ala Phe Glu Gly Asn Ser Asn Leu Phe Trp Ala Glu Arg Phe
        130                 135                 140

Gly Lys Gln Phe Leu Gly Met Asn Asp Leu Trp Val Lys His Cys Gly
145                 150                 155                 160

Ile Ser His Thr Gly Ser Phe Lys Asp Leu Gly Met Thr Val Leu Val
                165                 170                 175

Ser Gln Val Asn Arg Leu Arg Lys Met Asn Arg Pro Val Val Gly Val
        180                 185                 190

Gly Cys Ala Ser Thr Gly Asp Thr Ser Ala Ala Leu Ser Ala Tyr Cys
        195                 200                 205

Ala Ser Ala Ala Ile Pro Ser Ile Val Phe Leu Pro Ala Asn Lys Ile
        210                 215                 220

Ser Leu Ala Gln Leu Val Gln Pro Ile Ala Asn Gly Ala Phe Val Leu
225                 230                 235                 240

Ser Ile Asp Thr Asp Phe Asp Gly Cys Met Gln Leu Ile Arg Glu Val
                245                 250                 255

Thr Ala Glu Leu Pro Ile Tyr Leu Ala Asn Ser Leu Asn Ser Leu Arg
        260                 265                 270

Leu Glu Gly Gln Lys Thr Ala Ala Ile Glu Ile Leu Gln Gln Phe Asp
        275                 280                 285

Trp Gln Val Pro Asp Trp Val Ile Val Pro Gly Gly Asn Leu Gly Asn
290                 295                 300

Ile Tyr Ala Phe Tyr Lys Gly Phe Lys Met Cys Gln Glu Leu Gly Leu
305                 310                 315                 320

Val Asp Lys Ile Pro Arg Leu Val Cys Ala Gln Ala Ala Asn Ala Asp
                325                 330                 335

Pro Leu Tyr Leu Tyr Phe Lys Ser Gly Trp Lys Glu Phe Lys Pro Val
        340                 345                 350

Lys Ser Ser Thr Thr Phe Ala Ser Ala Ile Gln Ile Gly Asp Pro Val
        355                 360                 365

Ser Ile Asp Arg Ala Val His Ala Leu Lys Ser Cys Asp Gly Ile Val
        370                 375                 380

Glu Glu Ala Thr Glu Glu Glu Leu Met Asp Ala Thr Ala Gln Ala Asp
385                 390                 395                 400

Ser Thr Gly Met Phe Ile Cys Pro His Thr Gly Val Ala Leu Thr Ala
                405                 410                 415

Leu Phe Lys Leu Arg Asn Ser Gly Leu Ile Lys Ala Thr Asp Arg Thr
        420                 425                 430

Val Val Val Ser Thr Ala His Gly Leu Lys Phe Thr Gln Ser Lys Ile
        435                 440                 445

Asp Tyr His Ser Lys Asp Ile Lys Asp Met Ala Cys Arg Tyr Ala Asn
```

```
              450                 455                 460
Pro Pro Met Gln Val Lys Ala Asp Phe Gly Ser Val Met Asp Val Leu
465                 470                 475                 480

Lys Thr Tyr Leu Gln Ser Lys Thr His
                485

<210> SEQ ID NO 64
<211> LENGTH: 1786
<212> TYPE: DNA
<213> ORGANISM: Triticum aestivum

<400> SEQUENCE: 64
gcacgaggcg acacccgccg ccaccacctc ctcgctctcc ctcctcttcg cccaccccca      60
cttccaccac ccctccacca agcagcgcct cgacaggtcc catctccgcc tcccgctccg     120
cgccgccgcg caccgcacgc gctgcgccac cgagggcgcc tcggcgtggt acgagccgtt     180
cccccccggcc tccgatggcg acccaacga gcgctactcg ctcgacgagg tcgtctaccg     240
ctccacctcc ggcggcctcc tcgacgtccg ccacgacatg gacgcgctcg cgcgcttccc     300
gggctcctac tggcgcgacc tcttcgactc ccgcgtcggc cgcaccacct ggccctacgg     360
ctccggcgtc tggtccaaga aggagttcgt gctcccggag atcgactccg accacatcgt     420
ctctctcttc gagggcaaca gcaacctctt ctgggcggag cgcctcggcc gcgagcacct     480
cggcgggatg aatgacctct gggtcaagca gtgcggcatc tcgcacactg gctccttcaa     540
ggacctcggc atgacggcgc tcgtcagcca ggtcaatcgc ctccgccggg ctccgctctc     600
gcgccccatc aacggcgtgg ggtgcgcgtc cactggcgac acctccgccg cgctctcggc     660
ctactgtgcc gctgcgggca tccccgccat cgtgttcctc cccgcagacc gcatctcgct     720
gcagcagctc atccagccca tcgccaacgg cgccacggtg ctctcgcttg acaccgattt     780
cgacggatgc atgcggctta tcagggaggt gacagctgag ctgcccatat acctcgcaaa     840
ctcactcaac tcgcttcggc tggaggggca aagactgca gccatagaga tattgcaaca     900
gttcaattgg caggtgccgg actgggtcat tatcccagga ggcaatctgg caacattta     960
tgctttctac aaggggtttg agatgtgccg tgctcttggg ctagttgatc gtgttccacg    1020
gcttgtatgt gcacaggctg ccaatgcaaa tccactgtac cggtattaca agtctgggtg    1080
gactgacttc caatcacttg ttgctggaac tacatttgca tctgccatac agattggtga    1140
tccagtatct attgaccgtg cggttgttgc gctgaaggca accgatggca ttgttgagga    1200
agctacagag gaggagctta tggatgcgac ggctcttgct gacctcactg ggatgtttgc    1260
ttgcccacat actgggggttg cacttgctgc cctgttcaag ctccgtgacc agggtatgat    1320
tggcactaat gaccgcacgg tggttgttag tacagcacac gggctaaagt tcacacaatc    1380
aaagatcgac taccatgata agaacatcaa ggacatgttg tgccagtatg ccaatccacc    1440
gatcagtgtg aagcctgact ttgggtctgt catggatgtt ctccagaaga agctcaatgg    1500
taagatctga gcttaccttt aattaacctc aagagttcta tcttgtttat cgtcacaacg    1560
gctgtacttt ggcatcttaa tcaactgcac ttggtgacca tggtatggcg atatcatctt    1620
tattttccag tactaggttc ttgaggctct tctaactata ggcaaaagtg gatagagctt    1680
tccttgtact ttatctgtat catgtaatag caataataat gtatgatgtt atggttgaat    1740
aattgtttgg ttcagccaaa aaaaaaaaa aaaaaaaaa aaaaaa                     1786

<210> SEQ ID NO 65
<211> LENGTH: 500
```

```
<212> TYPE: PRT
<213> ORGANISM: Triticum aestivum

<400> SEQUENCE: 65

Ala Thr Pro Ala Ala Thr Thr Ser Ser Leu Ser Leu Leu Phe Ala His
1               5                   10                  15

Pro His Phe His His Pro Ser Thr Lys Gln Arg Leu Asp Arg Ser His
            20                  25                  30

Leu Arg Leu Pro Leu Arg Ala Ala His Arg Thr Arg Cys Ala Thr
        35                  40                  45

Glu Gly Ala Ser Ala Trp Tyr Glu Pro Phe Pro Ala Ser Asp Gly
    50                  55                  60

Asp Pro Asn Glu Arg Tyr Ser Leu Asp Glu Val Val Tyr Arg Ser Thr
65                  70                  75                  80

Ser Gly Gly Leu Leu Asp Val Arg His Asp Met Asp Ala Leu Ala Arg
                85                  90                  95

Phe Pro Gly Ser Tyr Trp Arg Asp Leu Phe Asp Ser Arg Val Gly Arg
            100                 105                 110

Thr Thr Trp Pro Tyr Gly Ser Gly Val Trp Ser Lys Lys Glu Phe Val
        115                 120                 125

Leu Pro Glu Ile Asp Ser Asp His Ile Val Ser Leu Phe Glu Gly Asn
    130                 135                 140

Ser Asn Leu Phe Trp Ala Glu Arg Leu Gly Arg Glu His Leu Gly Gly
145                 150                 155                 160

Met Asn Asp Leu Trp Val Lys Gln Cys Gly Ile Ser His Thr Gly Ser
                165                 170                 175

Phe Lys Asp Leu Gly Met Thr Ala Leu Val Ser Gln Val Asn Arg Leu
            180                 185                 190

Arg Arg Ala Pro Leu Ser Arg Pro Ile Asn Gly Val Gly Cys Ala Ser
        195                 200                 205

Thr Gly Asp Thr Ser Ala Ala Leu Ser Ala Tyr Cys Ala Ala Ala Gly
210                 215                 220

Ile Pro Ala Ile Val Phe Leu Pro Ala Asp Arg Ile Ser Leu Gln Gln
225                 230                 235                 240

Leu Ile Gln Pro Ile Ala Asn Gly Ala Thr Val Leu Ser Leu Asp Thr
                245                 250                 255

Asp Phe Asp Gly Cys Met Arg Leu Ile Arg Glu Val Thr Ala Glu Leu
            260                 265                 270

Pro Ile Tyr Leu Ala Asn Ser Leu Asn Ser Leu Arg Leu Glu Gly Gln
        275                 280                 285

Lys Thr Ala Ala Ile Glu Ile Leu Gln Gln Phe Asn Trp Gln Val Pro
290                 295                 300

Asp Trp Val Ile Ile Pro Gly Gly Asn Leu Gly Asn Ile Tyr Ala Phe
305                 310                 315                 320

Tyr Lys Gly Phe Glu Met Cys Arg Ala Leu Gly Leu Val Asp Arg Val
                325                 330                 335

Pro Arg Leu Val Cys Ala Gln Ala Ala Asn Ala Asn Pro Leu Tyr Arg
            340                 345                 350

Tyr Tyr Lys Ser Gly Trp Thr Asp Phe Gln Ser Leu Val Ala Gly Thr
        355                 360                 365

Thr Phe Ala Ser Ala Ile Gln Ile Gly Asp Pro Val Ser Ile Asp Arg
370                 375                 380

Ala Val Val Ala Leu Lys Ala Thr Asp Gly Ile Val Glu Glu Ala Thr
385                 390                 395                 400
```

-continued

```
Glu Glu Glu Leu Met Asp Ala Thr Ala Leu Ala Asp Leu Thr Gly Met
            405                 410                 415

Phe Ala Cys Pro His Thr Gly Val Ala Leu Ala Ala Leu Phe Lys Leu
        420                 425                 430

Arg Asp Gln Gly Met Ile Gly Thr Asn Asp Arg Thr Val Val Val Ser
    435                 440                 445

Thr Ala His Gly Leu Lys Phe Thr Gln Ser Lys Ile Asp Tyr His Asp
450                 455                 460

Lys Asn Ile Lys Asp Met Leu Cys Gln Tyr Ala Asn Pro Pro Ile Ser
465                 470                 475                 480

Val Lys Pro Asp Phe Gly Ser Val Met Asp Val Leu Gln Lys Lys Leu
                485                 490                 495

Asn Gly Lys Ile
            500

<210> SEQ ID NO 66
<211> LENGTH: 8585
<212> TYPE: DNA
<213> ORGANISM: Artificial
<220> FEATURE:
<221> NAME/KEY: misc_feature
<222> LOCATION: (6716)..(6716)
<223> OTHER INFORMATION: N = A, C, G or T

<400> SEQUENCE: 66
ggccgccgac tcgacgatga gcgagatgac cagctccggc cgccgactcg acgatgagcg      60
agatgaccag ctccggccgc gacacaagtg tgagagtact aaataaatgc tttggttgta     120
cgaaatcatt acactaaata aaataatcaa agcttatata tgccttccgc taaggccgaa     180
tgcaaagaaa ttggttcttt ctcgttatct tttgccactt ttactagtac gtattaatta     240
ctacttaatc atctttgttt acggctcatt atatccgtcg acggcgcgcc gttctatagt     300
gtcacctaaa tcgtatgtgt atgatacata aggttatgta ttaattgtag ccgcgttcta     360
acgacaatat gtccatatgg tgcactctca gtacaatctg ctctgatgcc gcatagttaa     420
gccagccccg acacccgcca cacccgctg acgcgccctg acgggcttgt ctgctcccgg      480
catccgctta cagacaagct gtgaccgtct ccgggagctg catgtgtcag aggttttcac     540
cgtcatcacc gaaacgcgcg agacgaaagg gcctcgtgat acgcctattt ttataggtta     600
atgtcatgac caaaatccct taacgtgagt tttcgttcca ctgagcgtca gaccccgtag     660
aaaagatcaa aggatcttct tgagatcctt ttttctgcg cgtaatctgc tgcttgcaaa      720
caaaaaaacc accgctacca gcggtggttt gtttgccgga tcaagagcta ccaactcttt     780
ttccgaaggt aactggcttc agcagagcgc agataccaaa tactgtcctt ctagtgtagc     840
cgtagttagg ccaccacttc aagaactctg tagcaccgcc tacataccte gctctgctaa     900 tcctgttacc agtggctgct gccagtggcg ataagtcgtg tcttaccggg ttggactcaa     960
gacgatagtt accggataag gcgcagcggt cgggctgaac ggggggttcg tgcacacagc    1020
ccagcttgga gcgaacgacc tacaccgaac tgagatacct acagcgtgag cattgagaaa    1080
gcgccacgct tcccgaaggg agaaaggcgg acaggtatcc ggtaagcggc agggtcggaa    1140
caggagagcg cacagggag cttcagggg gaaacgcctg gtatctttat agtcctgtcg     1200
ggtttcgcca cctctgactt gagcgtcgat ttttgtgatg ctcgtcaggg gggcggagcc    1260
tatggaaaaa cgccagcaac gcggcctttt tacggttcct ggccttttgc tggccttttg    1320
ctcacatgtt ctttcctgcg ttatccctg attctgtgga taaccgtatt accgcctttg    1380
```

-continued

```
agtgagctga taccgctcgc cgcagccgaa cgaccgagcg cagcgagtca gtgagcgagg    1440
aagcggaaga gcgcccaata cgcaaaccgc ctctccccgc gcgttggccg attcattaat    1500
gcaggttgat cagattcgac atcgatctag taacatagat gacaccgcgc gcgataattt    1560
atcctagttt gcgcgctata ttttgttttc tatcgcgtat taaatgtata attgcgggac    1620
tctaatcata aaaacccatc tcataaataa cgtcatgcat tacatgttaa ttattacatg    1680
cttaacgtaa ttcaacagaa attatatgat aatcatcgca agaccggcaa caggattcaa    1740
tcttaagaaa ctttattgcc aaatgtttga acgatctgct tcgacgcact ccttctttag    1800
gtacctcact attcctttgc cctcggacga gtgctggggc gtcggtttcc actatcggcg    1860
agtacttcta cacagccatc ggtccagacg gccgcgcttc tgcgggcgat ttgtgtacgc    1920
ccgacagtcc cggctccgga tcggacgatt gcgtcgcatc gaccctgcgc ccaagctgca    1980
tcatcgaaat tgccgtcaac caagctctga tagagttggt caagaccaat gcggagcata    2040
tacgcccgga gccgcggcga tcctgcaagc tccggatgcc tccgctcgaa gtagcgcgtc    2100
tgctgctcca tacaagccaa ccacggcctc cagaagaaga tgttggcgac ctcgtattgg    2160
gaatccccga acatcgcctc gctccagtca atgaccgctg ttatgcggcc attgtccgtc    2220
aggacattgt tggagccgaa atccgcgtgc acgaggtgcc ggacttcggg gcagtcctcg    2280
gcccaaagca tcagctcatc gagagcctgc gcgacggacg cactgacggt gtcgtccatc    2340
acagtttgcc agtgatacac atggggatca gcaatcgcgc atatgaaatc acgccatgta    2400
gtgtattgac cgattccttg cggtccgaat gggccgaacc cgctcgtctg gctaagatcg    2460
gccgcagcga tcgcatccat ggcctccgcg accggctgca gaacagcggg cagttcggtt    2520
tcaggcaggt cttgcaacgt gacaccctgt gcacggcggg agatgcaata ggtcaggctc    2580
tcgctgaatt ccccaatgtc aagcacttcc ggaatcggga gcgcggccga tgcaaagtgc    2640
cgataaacat aacgatcttt gtagaaacca tcggcgcagc tatttacccg caggacatat    2700
ccacgccctc ctacatcgaa gctgaaagca cgagattctt cgccctccga gagctgcatc    2760
aggtcggaga cgctgtcgaa cttttcgatc agaaacttct cgacagacgt cgcggtgagt    2820
tcaggctttt tcatggttta ataagaagag aaaagagttc ttttgttatg ctgaagtaa     2880 tagagaaatg agctcgagcg tgtcctctcc aaatgaaatg aacttcctta tatagaggaa    2940
gggtcttgcg aaggatagtg ggattgtgcg tcatccctta cgtcagtgga gatgtcacat    3000
caatccactt gctttgaaga cgtggttgga acgtcttctt tttccacgat gctcctcgtg    3060
ggtgggggtc catctttggg accactgtcg gcagaggcat cttgaatgat agcctttcct    3120
ttatcgcaat gatggcattt gtaggagcca ccttcctttt ctactgtcct ttcgatgaag    3180
tgacagatag ctgggcaatg gaatccgagg aggtttcccg aaattatcct ttgttgaaaa    3240
gtctcaatag ccctttggtc ttctgagact gtatctttga cattttggga gtagaccaga    3300
gtgtcgtgct ccaccatgtt gacgaagatt tcttcttgt  cattgagtcg taaaagactc    3360
tgtatgaact gttcgccagt cttcacggcg agttctgtta gatcctcgat ttgaatctta    3420
gactccatgc atggccttag attcagtagg aactaccttt ttagagactc caatctctat    3480
tacttgcctt ggtttatgaa gcaagccttg aatcgtccat actggaatag tacttctgat    3540
cttgagaaat atgtctttct ctgtgttctt gatgcaatta gtcctgaatc ttttgactgc    3600
atctttaacc ttcttgggaa ggtatttgat ctcctggaga ttgttactcg ggtagatcgt    3660
cttgatgaga cctgctgcgt aggcctctct aaccatctgt gggtcagcat tctttctgaa    3720
```

```
attgaagagg ctaaccttct cattatcagt ggtgaacata gtgtcgtcac cttcaccttc   3780
gaacttcctt cctagatcgt aaagatagag gaaatcgtcc attgtaatct ccggggcaaa   3840
ggagatctct tttggggctg atcactgct gggccttttg gttcctagcg tgagccagtg    3900
ggcttttttgc tttggtgggc ttgttagggc cttagcaaag ctcttgggct tgagttgagc  3960
ttctcctttg gggatgaagt tcaacctgtc tgtttgctga cttgttgtgt acgcgtcagc   4020
tgctgctctt gcctctgtaa tagtggcaaa tttcttgtgt gcaactccgg gaacgccgtt   4080
tgttgccgcc tttgtacaac cccagtcatc gtatataccg gcatgtggac cgttatacac   4140
aacgtagtag ttgatatgag ggtgttgaat acccgattct gctctgagag gagcaactgt   4200
gctgttaagc tcagattttt gtgggattgg aattggatcg atctcgatcc cgcgaaatta   4260
atacgactca ctatagggag accacaacgg tttccctcta gaaataattt tgtttaactt   4320
taagaaggag atatacccat ggaaaagcct gaactcaccg cgacgtctgt cgagaagttt   4380
ctgatcgaaa agttcgacag cgtctccgac ctgatgcagc tctcggaggg cgaagaatct   4440
cgtgctttca gcttcgatgt aggagggcgt ggatatgtcc tgcgggtaaa tagctgcgcc   4500
gatggttct acaaagatcg ttatgtttat cggcactttg catcggccgc gctcccgatt    4560
ccggaagtgc ttgacattgg ggaattcagc gagagcctga cctattgcat ctcccgccgt   4620
gcacagggtg tcacgttgca agacctgcct gaaaccgaac tgcccgctgt tctgcagccg   4680
gtcgcggagg ctatggatgc gatcgctgcg gccgatctta gccagacgag cgggttcggc   4740
ccattcggac cgcaaggaat cggtcaatac actacatggc gtgatttcat atgcgcgatt   4800
gctgatcccc atgtgtatca ctggcaaact gtgatggacg acaccgtcag tgcgtccgtc   4860
gcgcaggctc tcgatgagct gatgctttgg gccgaggact gccccgaagt ccggcacctc   4920
gtgcacgcgg atttcggctc caacaatgtc ctgacggaca atggccgcat aacagcggtc   4980
attgactgga gcgaggcgat gttcggggat tcccaatacg aggtcgccaa catcttcttc   5040
tggaggccgt ggttggcttg tatggagcag cagacgcgct acttcgagcg gaggcatccg   5100
gagcttgcag atcgccgcg gctccgggcg tatatgctcc gcattggtct tgaccaactc    5160
tatcagagct tggttgacgg caatttcgat gatgcagctt gggcgcaggg tcgatgcgac   5220
gcaatcgtcc gatccggagc cgggactgtc gggcgtacac aaatcgcccg cagaagcgcg   5280
gccgtctgga ccgatggctg tgtagaagta ctcgccgata gtggaaaccg acgccccagc   5340
actcgtccga gggcaaagga atagtgaggt acagcttgga tcgatccggc tgctaacaaa   5400
gcccgaaagg aagctgagtt ggctgctgcc accgctgagc aataactagc ataacccctt   5460
ggggcctcta acgggtctt gagggggtttt ttgctgaaag gaggaactat atccggatga   5520
tcgggcgcgc caagcttgga tcctcgaaga gaagggttaa taacacactt ttttaacatt   5580
tttaacacaa attttagtta tttaaaaatt tattaaaaaa tttaaaataa gaagaggaac   5640
tctttaaata aatctaactt acaaaatta tgatttttaa taagtttca ccaataaaaa     5700
atgtcataaa aatatgttaa aaagtatatt atcaatattc tctttatgat aaataaaaag   5760
aaaaaaaaaa taaagttaa gtgaaaatga gattgaagtg acttaggtg tgtataaata     5820
tatcaacccc gccaacaatt tatttaatcc aaatatattg aagtatatta ttccatagcc   5880
tttatttatt tatatattta ttatataaaa gctttatttg ttctaggttg ttcatgaaat   5940
atttttttgg tttatctcc gttgtaagaa aatcatgtgc tttgtgtcgc cactcactat    6000
tgcagctttt tcatgcattg gtcagattga cggttgattg tatttttgtt ttttatggtt   6060
ttgtgttatg acttaagtct tcatctctttt atctcttcat caggtttgat ggttacctaa   6120
```

```
tatggtccat gggtacatgc atggttaaat taggtggcca actttgttgt gaacgataga    6180
atttttttta tattaagtaa actattttta tattatgaaa taataataaa aaaatatttt    6240
tatcattatt aacaaaatca tattagttaa tttgttaact ctataataaa agaaatactg    6300
taacattcac attacatggt aacatctttc caccctttca tttgtttttt gtttgatgac    6360
tttttttctt gtttaaattt atttcccttc ttttaaattt ggaatacatt atcatcatat    6420
ataaactaaa atactaaaaa caggattaca caaatgataa ataataacac aaatatttat    6480
aaatctagct gcaatatatt taaactagct atatcgatat tgtaaaataa aactagctgc    6540
attgatactg ataaaaaaat atcatgtgct ttctggactg atgatgcagt actttttga     6600 cattgccttt attttatttt tcagaaaagc tttcttagtt ctgggttctt cattatttgt    6660
ttcccatctc cattgtgaat tgaatcattt gcttcgtgtc acaaatacaa tttagntagg    6720
tacatgcatt ggtcagattc acggtttatt atgtcatgac ttaagttcat ggtagtacat    6780
tacctgccac gcatgcatta tattggttag atttgatagg caaatttggt tgtcaacaat    6840
ataaatataa ataatgtttt tatattacga ataacagtg atcaaaacaa acagtttat      6900 ctttattaac aagattttgt ttttgtttga tgacgttttt taatgtttac gctttccccc    6960
ttcttttgaa tttagaacac tttatcatca taaaatcaaa tactaaaaaa attacatatt    7020
tcataaataa taacacaaat atttttaaaa aatctgaaat aataatgaac aatattacat    7080
attatcacga aaattcatta ataaaaatat tatataaata aaatgtaata gtagttatat    7140
gtaggaaaaa agtactgcac gcataatata tacaaaaaga ttaaaatgaa ctattataaa    7200
taataacact aaattaatgg tgaatcatat caaaataatg aaaaagtaaa taaaatttgt    7260
aattaacttc tatatgtatt acacacacaa ataataaata atagtaaaaa aaattatgat    7320
aaatatttac catctcataa gatatttaaa ataatgataa aaatatagat tattttttat    7380
gcaactagct agccaaaaag agaacacggg tatatataaa aagagtacct ttaaattcta    7440
ctgtacttcc tttattcctg acgttttat atcaagtgga catacgtgaa gatttttaatt   7500 atcagtctaa atatttcatt agcacttaat acttttctgt tttattccta tcctataagt    7560
agtcccgatt ctcccaacat tgcttattca cacaactaac taagaaagtc ttccatagcc    7620 cccccaagcgg ccggagctgg tcatctcgct catcgtcgag tcggcggccg gagctggtca   7680
tctcgctcat cgtcgagtcg gcggccgctc cggctggaag gagtttaagc ctgtgaagtc    7740
aagcactacc tttgcctctg ccattcaaat tggtgatcct gtttccatcg acagggcggt    7800 tcacgccta aagagttgcg atgggatcgt ggaggaggcc accgaggagg agttgatgga     7860
tgctacggcg caggcagatt ccactgggat gtttatctgc ccccacactg gggttgcttt    7920
gactgctttg tttaagctca ggaacagtgg gcttattaag gccactgata ggactgtggt    7980
ggttagcact gctcatggcc tcaagttcac tcagtccaag atcgattacc attctaagga    8040
catcaaggac atggcttgcc gctatgctaa ccctcccatg caagtcaagg ctgattttgg    8100
gtcggttatg gatgtttga agacgtattt gcagagtaag actcattagg ttagcattgc     8160 aacttttct cctctcttcc tgagtttgct gctgattatt tacttactat tattagccac     8220
ttctactcct gttttgtctt ttctataagc taggttgag tattgtagta atttgcctgc     8280
tgcattatgt atgctgtgct ccatattggg gcatcttagt atttgttgta gattttcttt    8340
gttgagcatt taatataata gctcaagtag aaaaaaatta attggataca atgagggagg    8400
aatgcacatt gttggcttgt tattactgga ttccagacca gaccacgcca tccccaaaag    8460
```

-continued

```
aaaataattc caaaaaatat aattagaaca gatttctttc actttcatgt tatgctgttg    8520
gcattaagct aagtgtgggt attaccaagc aactctatgc aatctgtgac aagtaattaa    8580
atcgc                                                                 8585
```

<210> SEQ ID NO 67
<211> LENGTH: 32
<212> TYPE: DNA
<213> ORGANISM: Artificial
<220> FEATURE:
<223> OTHER INFORMATION: primer

<400> SEQUENCE: 67

```
gaattcgcgg ccgctccggc tggaaggagt tt                                   32
```

<210> SEQ ID NO 68
<211> LENGTH: 32
<212> TYPE: DNA
<213> ORGANISM: Artificial
<220> FEATURE:
<223> OTHER INFORMATION: primer

<400> SEQUENCE: 68

```
gaattcgcgg ccgcgattta attacttgtc ac                                   32
```

<210> SEQ ID NO 69
<211> LENGTH: 875
<212> TYPE: DNA
<213> ORGANISM: Artificial
<220> FEATURE:
<223> OTHER INFORMATION: threonine synthase gene fragment

<400> SEQUENCE: 69

```
tccggctgga aggagtttaa gcctgtgaag tcaagcacta cctttgcctc tgccattcaa      60
attggtgatc ctgtttccat cgacagggcg gttcacgccc taaagagttg cgatgggatc     120
gtggaggagg ccaccgagga ggagttgatg gatgctacgg cgcaggcaga ttccactggg     180
atgtttatct gcccccacac tgggggttgct ttgactgctt tgtttaagct caggaacagt    240
gggcttatta aggccactga taggactgtg gtggttagca ctgctcatgg cctcaagttc     300
actcagtcca agatcgatta ccattctaag gacatcaagg acatggcttg ccgctatgct     360
aaccctccca tgcaagtcaa ggctgatttt gggtcggtta tggatgtttt gaagacgtat     420
ttgcagagta agactcatta ggttagcatt gcaactttt ctcctctctt cctgagtttg      480
ctgctgatta tttacttact attattagcc acttctactc ctgttttgtc ttttctataa     540
gctaggtttg agtattgtag taatttgcct gctgcattat gtatgctgtg ctccatattg     600
gggcatctta gtatttgttg tagattttct ttgttgagca tttaatataa tagctcaagt     660
agaaaaaaat taattggata caatgaggga ggaatgcaca ttgttggctt gttattactg     720
gattccagac cagaccacgc catccccaaa agaaaataat tccaaaaaat ataattagaa     780
cagatttctt tcactttcat gttatgctgt tggcattaag ctaagtgtgg gtattaccaa     840
gcaactctat gcaatctgtg acaagtaatt aaatc                                875
```

US 7,368,633 B2

PLANT AMINO ACID BIOSYNTHETIC ENZYMES

This application is a continuation-in-part of U.S. application Ser. No. 10/734,698, filed on Dec. 12, 2003, now granted as U.S. Pat. No. 7,022,895, which is a divisional of U.S. application Ser. No. 09/424,978, filed Dec. 2, 1999, now granted as U.S. Pat. No. 6,664,445, which is a 35 U.S.C. 371 national filing of International Application No. PCT/US98/11692, filed Jun. 5, 1998, which claims priority to U.S. Provisional Application No. 60/048,771, filed Jun. 6, 1997, and U.S. Provisional Application No. 60/049,443, filed Jun. 12, 1997, the entire contents of which are hereby incorporated by reference.

FIELD OF THE INVENTION

This invention is in the field of plant molecular biology. More specifically, this invention pertains to nucleic acid fragments encoding enzymes involved in amino acid biosynthesis in plants and seeds.

BACKGROUND OF THE INVENTION

Many vertebrates, including man, lack the ability to manufacture a number of amino acids and therefore require these amino acids preformed in the diet. These are called essential amino acids. Human food and animal feed, derived from many grains, are deficient in essential amino acids, such as lysine, the sulfur amino acids methionine and cysteine, threonine and tryptophan. For example, in corn (*Zea mays L.*) lysine is the most limiting amino acid for the dietary requirements of many animals. Soybean (*Glycine max L.*) meal is used as an additive to corn-based animal feeds primarily as a lysine supplement. Thus, an increase in the lysine content of either corn or soybean would reduce or eliminate the need to supplement mixed grain feeds with lysine produced via fermentation of microbes. Furthermore, in corn the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Lysine, threonine, methionine, cysteine and isoleucine are amino acids derived from aspartate. Regulation of the biosynthesis of each member of this family is interconnected (see FIG. 1). One approach to increasing the nutritional quality of human foods and animal feed is to increase the production and accumulation of specific free amino acids via genetic engineering of this biosynthetic pathway. Alteration of the activity of enzymes in this pathway could lead to altered levels of lysine, threonine, methionine, cysteine and isoleucine. However, few of the genes encoding enzymes that regulate this pathway in plants, especially corn, soybeans and wheat, are available.

The organization of the pathway leading to biosynthesis of lysine, threonine, methionine, cysteine and isoleucine indicates that over-expression or reduction of expression of genes encoding, inter alia, threonine synthase, dihydrodipicolinate reductase, diaminopimelate epimerase, threonine deaminase and S-adenosylmethionine synthetase in corn, soybean, wheat and other crop plants could be used to alter levels of these amino acids in human food and animal feed. Accordingly, availability of nucleic acid sequences encoding all or a portion of these enzymes would facilitate development of nutritionally improved crop plants.

SUMMARY OF THE INVENTION

The instant invention relates to isolated nucleic acid fragments encoding plant enzymes involved in amino acid biosynthesis. Specifically, this invention concerns isolated nucleic acid fragments encoding the following plant enzymes that catalyze steps in the biosynthesis of lysine, threonine, methionine, cysteine and isoleucine from aspartate: dihydrodipicolinate reductase, diaminopimelate epimerase, threonine synthase, threonine deaminase and S-adenosylmethionine synthetase. In addition, this invention relates to nucleic acid fragments that are complementary to nucleic acid fragments encoding the listed plant biosynthetic enzymes.

In another embodiment, the instant invention relates to chimeric genes encoding the amino acid biosynthetic acid enzymes listed above or to chimeric genes that comprise nucleic acid fragments that are complementary to the nucleic acid fragments encoding the enzymes, operably linked to suitable regulatory sequences, wherein expression of the chimeric genes results in production of levels of the encoded enzymes in transformed host cells that are altered (i.e., increased or decreased) from the levels produced in untransformed host cells.

In a further embodiment, the instant invention concerns a transformed host cell comprising in its genome a chimeric gene encoding a plant amino acid biosynthetic enzyme operably linked to suitable regulatory sequences, the enzyme selected from the group consisting of: dihydrodipicolinate reductase, diaminopimelate epimerase, threonine synthase, threonine deaminase and S-adenosylmethionine synthetase. Expression of the chimeric gene results in production of altered levels of the biosynthetic enzyme in the transformed host cell. The transformed host cells can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a plant biosynthetic enzyme in a transformed host cell comprising: a) transforming a host cell with a chimeric gene comprising a nucleic acid fragment encoding a plant biosynthetic enzyme selected from the group consisting of dihydrodipicolinate reductase, diaminopimelate epimerase, threonine synthase, threonine deaminase and S-adenosylmethionine synthetase, operably linked to suitable regulatory sequences; and b) growing the transformed host cell under conditions that are suitable for expression of the chimeric gene wherein expression of the chimeric gene results in production of altered levels of the biosynthetic enzyme in the transformed host cell.

An additional embodiment of the instant invention concerns a method for obtaining a nucleic acid fragment encoding all or substantially all of an amino acid sequence encoding a plant dihydrodipicolinate reductase, diaminopimelate epimerase, threonine synthase, threonine deaminase and S-adenosylmethionine synthetase.

A further embodiment of the instant invention is a method for evaluating at least one compound for its ability to inhibit the activity of a plant biosynthetic enzyme selected from the group consisting of dihydrodipicolinate reductase, diaminopimelate epimerase, threonine synthase, threonine deaminase and S-adenosylmethionine synthetase, the method comprising the steps of: (a) transforming a host cell with a chimeric gene comprising a nucleic acid fragment encoding a plant biosynthetic enzyme selected from the group consisting of dihydrodipicolinate reductase, diaminopimelate epimerase, threonine synthase, threonine deaminase and S-denosylmethionine synthetase, operably linked to suitable regulatory sequences; (b) growing the transformed host cell under conditions that are suitable for expression of the chimeric gene wherein expression of the chimeric gene results in production of the biosynthetic enzyme in the transformed host cell; (c) optionally purifying the biosynthetic enzyme expressed by the transformed host cell; (d) treating the biosynthetic enzyme with a compound to be tested; and (e) comparing the activity of the biosynthetic enzyme that has been treated with a test compound to the activity of an untreated biosynthetic enzyme, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and sequence descriptions which form a part of this application.

FIG. 1 depicts the biosynthetic pathway for the aspartate family of amino acids. The following abbreviations are used: AK=aspartokinase; ASADH=aspartic semialdehyde dehydrogenase; DHDPS=dihydrodipicolinate synthase; DHDPR=dihydrodipicolinate reductase; DAPEP=diaminopimelate epimerase; DAPDC=diaminopimelate decarboxylase; HDH=homoserine dehydrogenase; HK=homoserine kinase; TS=threonine synthase; TD=threonine deaminase; CγS=cystathionine γ-synthase; CβL=cystathionine β-lyase; MS=methionine synthase; CS=cysteine synthase; and SAMS=S-adenosylmethionine synthase.

FIG. 2 shows a multiple alignment of the amino acid sequence fragments reported herein encoding dihydrodipicolinate reductase (SEQ ID NOs:2 and 4) and the *Synechocystis* sp. dihydrodipicolinate reductase sequence set forth in DDBJ Accession No. D90899 (SEQ ID NO:5).

FIGS. 3A and 3B show a multiple alignment of the amino acid sequence fragments reported herein encoding diaminopimelate epimerase (SEQ ID NOs:7, 9, 11, and 13) and the *Synechocystis* sp. diaminopimelate epimerase sequence set forth in DDBJ Accession No. D90917 (SEQ ID NO:14).

FIGS. 4A, 4B and 4C show a multiple alignment of the amino acid sequence fragments reported herein encoding threonine synthase (SEQ ID NOs:16, 18, 20, 22, 24, and 26) and the *Arabidopsis thaliana* threonine synthase sequence set forth in GenBank Accession No. L41666 (SEQ ID NO:27).

FIGS. 5A and 5B show a multiple alignment of the amino acid sequence fragments reported herein encoding threonine deaminase (SEQ ID NOs:29, 31, and 33) to the *Burkholderia capacia* threonine synthase set forth in GenBank Accession No. U40630 (SEQ ID NO:34).

FIGS. 6A, 6B and 6C show the nucleotide sequence alignment of the S-adenosylmethionine synthetase reported herein for corn (SEQ ID NO:35) with the *Oryza sativa* S-adenosylmethionine synthetase nucleotide sequence set forth in EMBL Accession No. Z26867 (SEQ ID NO:37).

FIGS. 7A, 7B and 7C show the nucleotide sequence alignment of the S-adenosylmethionine synthetase reported here for soybean (SEQ ID NO:38) with the *Lycopersicon esculentum* S-adenosyl-methionine synthetase nucleotide sequence set forth in EMBL Accession No. Z24741 (SEQ ID NO:40).

FIGS. 8A, 8B and 8C show the nucleotide sequence alignment of the S-adenosylmethionine synthetase reported here for wheat (SEQ ID NO:41) with the *Hordeum vulgare* S-adenosylmethionine synthetase nucleotide sequence set forth in DDBJ Accession No. D63835 (SEQ ID NO:43).

FIGS. 9A, 9B, 9C, 9D, 9E and 9F show a multiple alignment of the amino acid sequences reported herein encoding threonine synthase (SEQ ID NOs:45, 47, 49, 51 and 53) to the *Oryza sativa* threonine synthase set forth in NCBI General Identifier No. 34911416 (SEQ ID NO:54) and the *Solanum tuberosum* sequence set forth in NCBI General Identifier No. 20140867 (SEQ ID NO:55).

FIGS. 10A, 10B, 10C, 10D and 10E show a multiple alignment of the amino acid sequences reported herein encoding threonine synthase (minus the regulatory region) (SEQ ID NOs:57, 59, 61, 63 and 65) to the *Oryza sativa* threonine synthase set forth in NCBI General Identifier No. 34911416 (SEQ ID NO:54) and the *Solanum tuberosum* sequence set forth in NCBI General Identifier No. 20140867 (SEQ ID NO:55).

Figure 1:
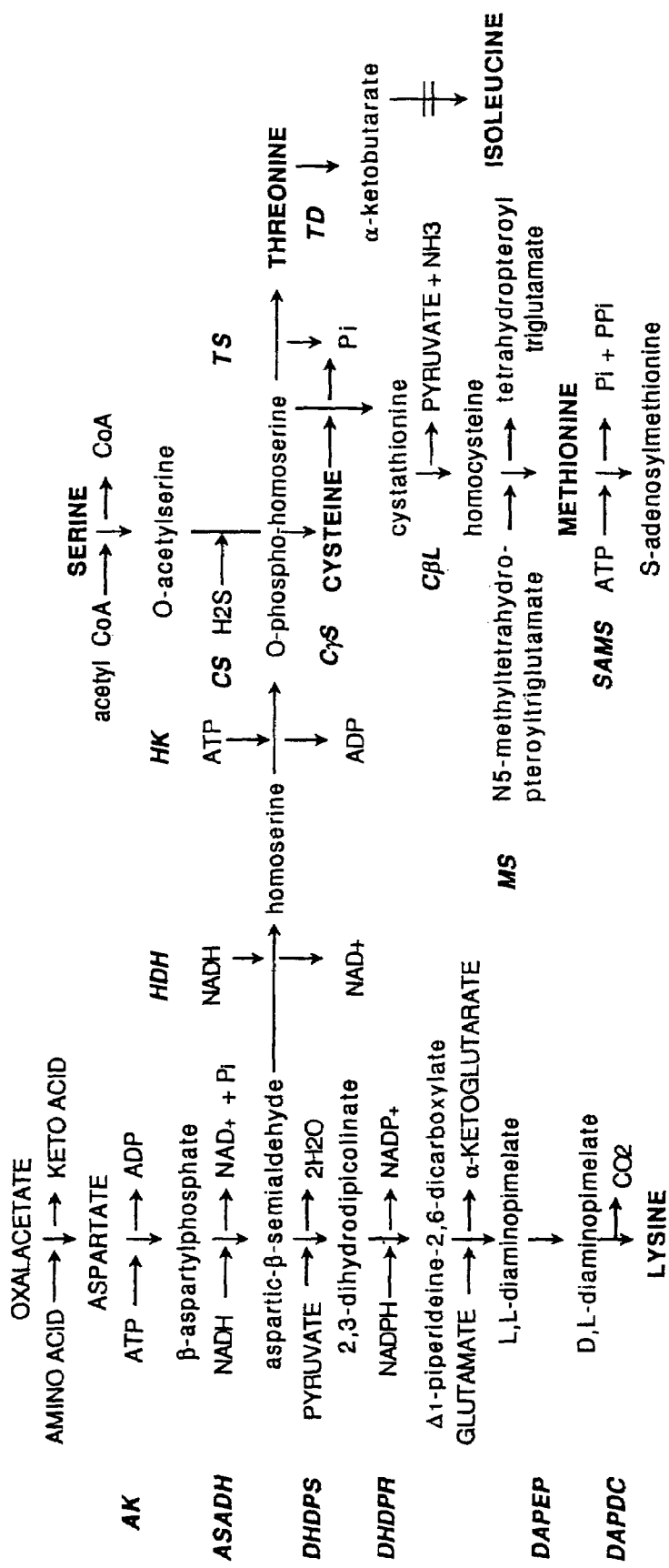
Figure 11:
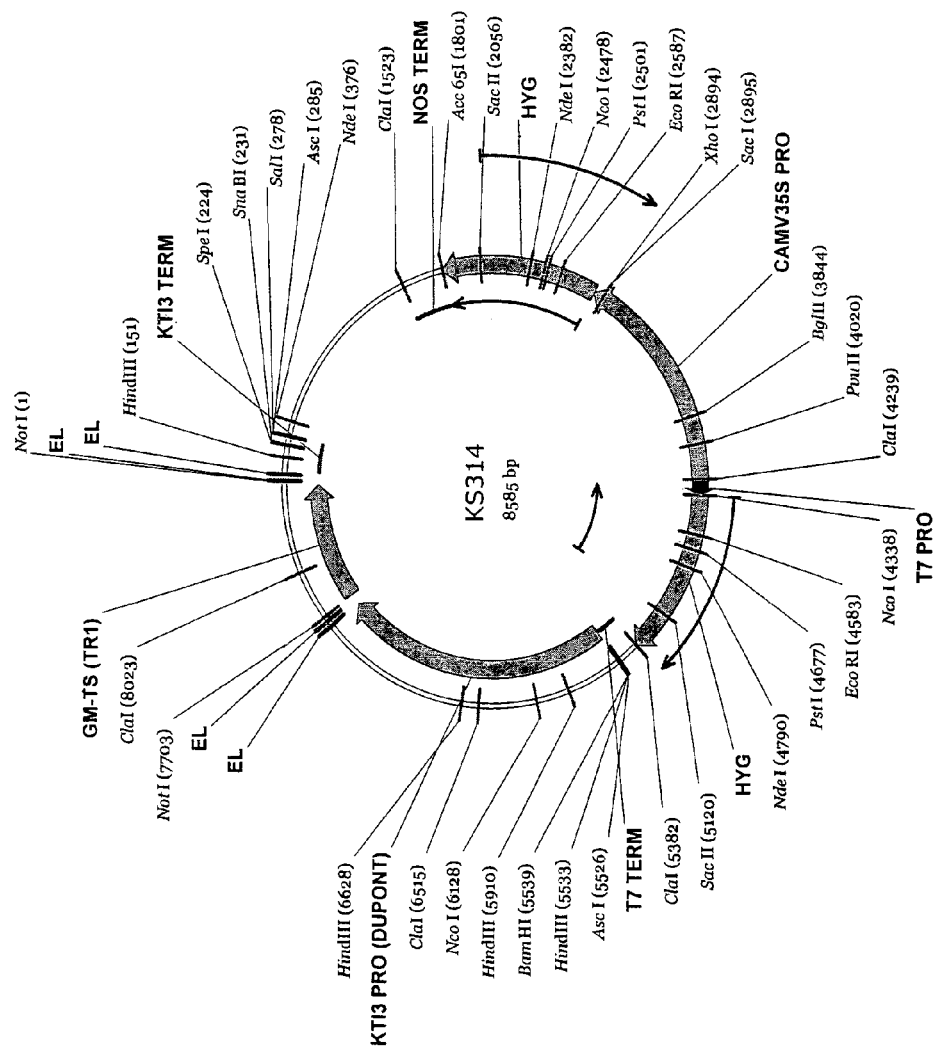

FIG. 11 is a schematic depiction of vector KS314.

Amino acid sequence alignments were performed using the Clustal method of alignment (Higgins, D. G. and Sharp, P. M. (1989) *CABIOS* 5:151-153), from the Megalign program of the LASARGENE bioinformatics computing suite (DNASTAR Inc., Madison, Wis.). Nucleotide sequence alignments were a result of the BLASTN search performed with each individual sequence.

The following sequence descriptions and sequence listings attached hereto comply with the rules governing nucleotide and/or amino acid sequence disclosures in patent applications as set forth in 37 C.F.R. §1.821-1.825.

SEQ ID NO:1 is the nucleotide sequence comprising the entire cDNA insert in clone csi1n.pk0042.a3 encoding a corn dihydrodipicolinate reductase.

SEQ ID NO:2 is the deduced amino acid sequence of a portion of a corn dihydrodipicolinate reductase derived from the nucleotide sequence of SEQ ID NO:1.

SEQ ID NO:3 is the nucleotide sequence comprising a portion of the cDNA insert in clone rls2.pk0017.d3 encoding a rice dihydrodipicolinate reductase.

SEQ ID NO:4 is the deduced amino acid sequence of a portion of a rice dihydrodipicolinate reductase derived from the nucleotide sequence of SEQ ID NO:3.

SEQ ID NO:5 is the amino acid sequence of the entire *Synechocystis* sp. dihydrodipicolinate reductase DDBJ Accession No. D90899.

SEQ ID NO:6 is the nucleotide sequence comprising the entire cDNA insert in clone chp2.pk0008.h4 encoding a corn diaminopimelate epimerase.

SEQ ID NO:7 is the deduced amino acid sequence of a portion of a corn diaminopimelate epimerase derived from the nucleotide sequence of SEQ ID NO:6.

SEQ ID NO:8 is the nucleotide sequence comprising a portion of the cDNA insert in clone rls48.pk0036.h10 encoding a rice diaminopimelate epimerase.

SEQ ID NO:9 is the deduced amino acid sequence of a portion of a rice diaminopimelate epimerase derived from the nucleotide sequence of SEQ ID NO:8.

SEQ ID NO:10 is the nucleotide sequence comprising a contig formed of portions of sfl1.pk0031.h3, and sgs1c.pk002.k12, and the entire cDNA insert from clones se2.pk0005.f1, and ses8w.pk0010.h11 encoding a soybean diaminopimelate epimerase.

SEQ ID NO:11 is the deduced amino acid sequence of a soybean diaminopimelate epimerase derived from the nucleotide sequence of SEQ ID NO:10.

SEQ ID NO:12 is the nucleotide sequence comprising a portion of the cDNA insert in clone wlm24.pk0030.g4 encoding a wheat diaminopimelate epimerase.

SEQ ID NO:13 is the deduced amino acid sequence of a portion of a wheat diaminopimelate epimerase derived from the nucleotide sequence of SEQ ID NO:12.

SEQ ID NO:14 is the nucleotide sequence comprising the entire *Synechocystis* sp. diaminopimelate epimerase DDBJ Accession No. D90917.

SEQ ID NO:15 is the nucleotide sequence comprising the entire cDNA insert in clone cc2.pk0031.c9 encoding a corn threonine synthase.

SEQ ID NO:16 is the deduced amino acid sequence of a portion of a corn threonine synthase derived from the nucleotide sequence set forth in SEQ ID NO:15.

SEQ ID NO:17 is the nucleotide sequence comprising part of the cDNA insert in clone cs1.pk0058.g5 encoding a corn threonine synthase.

SEQ ID NO:18 is the deduced amino acid sequence of a portion of a corn threonine synthase derived from the nucleotide sequence of SEQ ID NO:17.

SEQ ID NO:19 is the nucleotide sequence comprising part of the cDNA insert in clone rls72.pk0018.e7 encoding a rice threonine synthase.

SEQ ID NO:20 is deduced amino acid sequence of a portion of a rice threonine synthase derived from the nucleotide sequence set forth in SEQ ID NO:19.

SEQ ID NO:21 is the nucleotide sequence comprising part of the cDNA insert in clone se1.06a03 encoding a soybean threonine synthase.

SEQ ID NO:22 is the deduced amino acid sequence of a portion of a soybean threonine synthase derived from the nucleotide sequence set forth in SEQ ID NO:21.

SEQ ID NO:23 is the nucleotide sequence comprising the entire cDNA insert in clone sr1.pk0003.f6 encoding a soybean threonine synthase.

SEQ ID NO:24 is the deduced amino acid sequence of a portion of a soybean threonine synthase derived from the nucleotide sequence set forth in SEQ ID NO:23.

SEQ ID NO:25 is the nucleotide sequence comprising part of the cDNA insert in clone wr1.pk0085.h2 encoding a wheat threonine synthase.

SEQ ID NO:26 is the deduced amino acid sequence of a portion of a wheat threonine synthase derived from the nucleotide sequence set forth in SEQ ID NO:25.

SEQ ID NO:27 is the entire amino acid sequence of an *Arabidopsis thaliana* threonine synthase found in GenBank Accession No. L41666.

SEQ ID NO:28 is the nucleotide sequence comprising the entire cDNA insert in clone cen1.pk0064.f4 encoding a corn threonine deaminase.

SEQ ID NO:29 is the deduced amino acid sequence of a portion of a corn threonine deaminase derived from the nucleotide sequence set forth in SEQ ID NO:28.

SEQ ID NO:30 is the nucleotide sequence comprising a portion of the cDNA insert in clone sfl1.pk0055.h7 encoding a soybean threonine deaminase.

SEQ ID NO:31 is the deduced amino acid sequence of a portion of a soybean threonine deaminase derived from the nucleotide sequence set forth in SEQ ID NO:30.

SEQ ID NO:32 is the nucleotide sequence comprising the entire cDNA insert in clone sre.pk0044.f3 encoding a soybean threonine deaminase.

SEQ ID NO:33 is the deduced amino acid sequence of a portion of a soybean threonine deaminase derived from the nucleotide sequence set forth in SEQ ID NO:32.

SEQ ID NO:34 is the entire amino acid sequence of a *Burkholderia capacia* threonine deaminase found in GenBank Accession No. U49630.

SEQ ID NO:35 is the nucleotide sequence comprising the entire cDNA insert in clone cc3.mm0002.d2 encoding the entire corn S-adenosylmethionine synthetase.

SEQ ID NO:36 is the deduced amino acid sequence of a corn S-adenosylmethionine synthetase derived from the nucleotide sequence set forth in SEQ ID NO:35.

SEQ ID NO:37 is the entire nucleotide sequence of a *Oryza sativa* S-adenosylmethionine synthetase found in EMBL Accession No. Z26867.

SEQ ID NO:38 is the nucleotide sequence of the entire cDNA insert in clone s2.12b06 encoding the entire soybean S-adenosyl-methionine synthetase.

SEQ ID NO:39 is the deduced amino acid sequence of the entire soybean S-adenosylmethionine synthetase derived from the nucleotide sequence set forth in SEQ ID NO:38.

SEQ ID NO:40 is the entire nucleotide sequence of a *Lycopersicon esculentum* S-adenosyl-methionine synthetase found in EMBL Accession No. Z24741.

SEQ ID NO:41 is the nucleotide sequence comprising a contig formed of portions of the cDNA inserts in clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 encoding a portion of a wheat S-adenosyl-methionine synthetase.

SEQ ID NO:42 is the deduced amino acid sequence of a wheat S-adenosylmethionine synthetase derived from the nucleotide sequence set forth in SEQ ID NO:41.

SEQ ID NO:43 is the entire nucleotide sequence of a *Hordeum vulgare* S-adenosylmethionine synthetase found in DDBJ Accession No. D63835.

SEQ ID NO:44 is the nucleotide sequence comprising the entire cDNA insert in clone cpj1c.pk004.b4:fis encoding a corn threonine synthase.

SEQ ID NO:45 is the deduced amino acid sequence of a corn threonine synthase derived from the nucleotide sequence set forth in SEQ ID NO:44.

SEQ ID NO:46 is the nucleotide sequence comprising the entire cDNA insert in clone cmm.pk0002.d3:fis encoding a corn threonine synthase.

SEQ ID NO:47 is the deduced amino acid sequence of a corn threonine synthase derived from the nucleotide sequence of SEQ ID NO:46.

SEQ ID NO:48 is the nucleotide sequence comprising a contig formed of the cDNA inserts in clones scb1c.pk003.113, sgs4c.pk003.h16 and sr1.pk0003.f6 encoding a soybean threonine synthase.

SEQ ID NO:49 is the deduced amino acid sequence of a soybean threonine synthase derived from the nucleotide sequence set forth in SEQ ID NO:48.

SEQ ID NO:50 is the nucleotide sequence comprising the entire cDNA insert in clone sdp4c.pk007.j10:fis encoding a soybean threonine synthase.

SEQ ID NO:51 is the deduced amino acid sequence of a soybean threonine synthase derived from the nucleotide sequence set forth in SEQ ID NO:50.

SEQ ID NO:52 is the nucleotide sequence comprising the entire cDNA insert in clone wlm4.pk0013.f4:fis encoding a wheat threonine synthase.

SEQ ID NO:53 is the deduced amino acid sequence of a wheat threonine synthase derived from the nucleotide sequence set forth in SEQ ID NO:52.

SEQ ID NO:54 is the amino acid sequence of threonine synthase from *Oryza sativa* (NCBI General Identifier No. 34911416).

SEQ ID NO:55 is the amino acid sequence of threonine synthase from *Solanum tuberosum* (NCBI General Identifier No. 20140867).

SEQ ID NO:56 is the nucleotide sequence comprising the entire cDNA insert in clone cmm.pk0002.d3:fis minus the 90 nucleotide regulatory sequence (nucleotides 205-294 of SEQ ID NO:46) encoding a corn threonine synthase.

SEQ ID NO:57 is the deduced amino acid sequence of a corn threonine synthase derived from the nucleotide sequence of SEQ ID NO:56. This amino acid sequence has 30 amino acids removed from the full-length protein (amino acids 50-79 of SEQ ID NO:47).

SEQ ID NO:58 is the nucleotide sequence comprising the entire cDNA insert in clone cpj1c.pk004.b4:fis minus the 90 nucleotide regulatory sequence (nucleotides 169-258 of SEQ ID NO:44) encoding a corn threonine synthase.

SEQ ID NO:59 is the deduced amino acid sequence of a corn threonine synthase derived from the nucleotide sequence of SEQ ID NO:58. This amino acid sequence has 30 amino acids removed from the full-length protein (amino acids 45-74 of SEQ ID NO:45).

SEQ ID NO:60 is the nucleotide sequence comprising contig formed of the cDNA inserts in clones scb1c.pk003.113, sgs4c.pk003.h16 and sr1.pk0003.f6 minus the 96 nucleotide regulatory sequence (nucleotides 242-337 of SEQ ID NO:48) encoding a soybean threonine synthase.

SEQ ID NO:61 is the deduced amino acid sequence of a soybean threonine synthase derived from the nucleotide sequence of SEQ ID NO:60. This amino acid sequence has 32 amino acids removed from the full-length protein (amino acids 41-72 of SEQ ID NO:49).

SEQ ID NO:62 is the nucleotide sequence comprising the entire cDNA insert in clone sdp4c.pk007.j10:fis minus the 96 nucleotide regulatory sequence (nucleotides 168-263 of SEQ ID NO:50) encoding a soybean threonine synthase.

SEQ ID NO:63 is the deduced amino acid sequence of a soybean threonine synthase derived from the nucleotide sequence of SEQ ID NO:62. This amino acid sequence has 32 amino acids removed from the full-length protein (amino acids 44-75 of SEQ ID NO:51).

SEQ ID NO:64 is the nucleotide sequence comprising the entire cDNA insert in clone wlm4.pk0003.f4:fis minus the 90 nucleotide regulatory sequence (nucleotides 164-253 of SEQ ID NO:52) encoding a soybean threonine synthase.

SEQ ID NO:65 is the deduced amino acid sequence of a wheat threonine synthase derived from the nucleotide sequence of SEQ ID NO:64. This amino acid sequence has 30 amino acids removed from the full-length protein (amino acids 53-82 of SEQ ID NO:53).

SEQ ID NO:66 is the 8585 bp nucleotide sequence of vector KS314.

SEQ ID NO:67 is the sequence of oligonucleotide primer MWG191 used in a PCR amplification of the threonine synthase gene fragment for insertion into soybean expression vector KS151 to produce vector KS314.

SEQ ID NO:68 is the sequence of oligonucleotide primer MWG192 used in a PCR amplification of the threonine synthase gene fragment for insertion into soybean expression vector KS151 to produce vector KS314.

SEQ ID NO:69 is the sequence of the threonine synthase gene fragment used for cosuppression of threonine synthase in Example 13.

The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein. The Clustal multiple alignment alogarithm (Higgins, D. G. and Sharp, P. M. (1989) *CABIOS* 5:151-153) was used here with a GAP PENALTY of 10 and a GAP LENGTH PENALTY of 10.

The "Clustal V method of alignment" corresponds to the alignment method labeled Clustal V (described by Higgins and Sharp (1989) *CABIOS*. 5:151-153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE 1, GAP PENALTY=3, WINDOW=5 and DIAGONALS SAVED=5. After alignment of the sequences, using the Clustal V program, it is possible to obtain a "percent identity" by viewing the "sequence distances" table on the same program. It is well understood by one skilled in the art that many levels of sequence identity are useful in identifying related polypeptide sequences. Useful examples of percent identities are 50%, 55%, 60%, 65%, 70%, 75%, 80%, 85%, 86%, 90%, or 95%, or any integer percentage from 55% to 100%.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403-410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the amino acid biosynthetic enzymes as set forth in SEQ ID NOs:2, 4, 7, 9, 11, 13, 16, 18, 20, 22, 24, 26, 29, 31, 33, 45, 47, 49, 51, 53, 57, 59, 61, 63 and 65. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual*;

Cold Spring Harbor Laboratory Press: Cold Spring Harbor, 1989 (hereinafter "Maniatis").

Nucleic acid fragments encoding at least a portion of several plant amino acid biosynthetic enzymes have been isolated and identified by comparison of random plant cDNA sequences to public databases containing nucleotide and protein sequences using the BLAST algorithms well known to those skilled in the art. Table 1 lists the amino acid biosynthetic enzymes that are described herein, and the designation of the cDNA clones that comprise the nucleic acid fragments encoding these enzymes.

TABLE 1

Amino Acid Biosynthetic Enzymes

| Enzyme | Clone | Plant |
| --- | --- | --- |
| dihydrodipicolinate reductase | cs1.pk0083.b10 | corn |
|  | rls2.pk0017.d3 | rice |
| diaminopimelate epimerase | chp2.pk0008.h4 | corn |
|  | rls48.pk0036.h10 | rice |
|  | se2.pk0005.f1 | soybean |
|  | ses8w.pk0010.f11 | soybean |
|  | sfl1.pk0031.h3 | soybean |
|  | sgs1c.pk002.k12 | soybean |
|  | wlm24.pk0030.g4 | wheat |
| threonine synthase | cc2.pk0031.c9 | corn |
|  | cs1.pk0058.g5 | corn |
|  | rls72.pk0018.e7 | rice |
|  | se1.06a03 | soybean |
|  | sr1.pk0003.f6 | soybean |
|  | wr1.pk0085.h2 | wheat |
|  | cpj1c.pk004.b4:fis | corn |
|  | cmm.pk0002.d3:fis | corn |
|  | Contig of: | soybean |
|  | scb1c.pk003.113 |  |
|  | sgs4c.pk003.h16 |  |
|  | sr1.pk0003.f6 |  |
|  | sdp4c.pk007.j10:fis | soybean |
|  | wlm4.pk0013.f4:fis | wheat |
| threonine deaminase | cen1.pk0064.f4 | corn |
|  | sfl1.pk0055.h7 | soybean |
|  | sre.pk0044.f3 | soybean |
| S-adenosylmethionine synthase | cc3.mn0002.d2 | corn |
|  | se2.12b06 | soybean |
|  | wre1.pk0002.c12 | wheat |
|  | wle1n.pk0070.b8 | wheat |
|  | wkm1c.pk0003.g4 | wheat |
|  | wlk1.pk0028.d3 | wheat |
|  | wre1n.pk170.d8 | wheat |
|  | wr1.pk0086.d5 | wheat |
|  | wr1.pk0103.h8 | wheat |
|  | wre1n.pk0082.b2 | wheat |

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other amino acid biosynthetic enzymes, either as cDNAs or genomic DNAs, could be isolated directly by using all or a portion of the instant nucleic acid fragments as DNA hybridization probes to screen libraries from any desired plant employing methodology well known to those skilled in the art (Maniatis). Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed biosynthetic enzymes are present at higher or lower levels than normal or in cell types or developmental stages in which they are not normally found. This would have the effect of altering the level of free amino acids in those cells.

Overexpression of the biosynthetic enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals may also be provided. The instant chimeric genes may also comprise one or more introns in order to facilitate gene expression.

Plasmid vectors comprising the instant chimeric genes can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant biosynthetic enzymes to different cellular compartments, or to facilitate their secretion from the cell. It is thus envisioned that the chimeric genes described above may be further supplemented by altering the coding sequences to encode enzymes with appropriate intracellular targeting sequences such as transit sequences (Keegstra, K. (1989) *Cell* 56:247-253), signal sequences or sequences encoding endoplasmic reticulum localization (Chrispeels, J. J., (1991) *Ann. Rev. Plant Phys. Plant Mol. Biol.* 42:21-53), or nuclear localization signals (Raikhel, N. (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of the genes encoding the instant biosynthetic enzymes in plants for some applications. In order to accomplish this, chimeric genes designed for co-suppression of the instant biosynthetic enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

The instant amino acid biosynthetic enzymes (or portions of the enzymes) may be produced in heterologous host cells, particularly in the cells of microbial hosts, and can be used to prepare antibodies to the enzymes by methods well known to those skilled in the art. The antibodies are useful for detecting the enzymes in situ in cells or in vitro in cell extracts. Preferred heterologous host cells for production of the instant amino acid biosynthetic enzymes are microbial hosts. Microbial expression systems and expression vectors containing regulatory sequences that direct high level expression of foreign proteins are well known to those skilled in the art. Any of these could be used to construct chimeric genes for production of the instant amino acid biosynthetic enzymes. These chimeric genes could then be introduced into appropriate microorganisms via transformation to provide high level expression of the enzymes. An example of a vector for high level expression of the instant amino acid biosynthetic enzymes in a bacterial host is provided (Example 11).

Additionally, the instant plant amino acid biosynthetic enzymes can be used as a targets to facilitate design and/or identification of inhibitors of the enzymes that may be useful as herbicides. This is desirable because the enzymes described herein catalyze various steps in a pathway leading to production of several essential amino acids. Accordingly, inhibition of the activity of one or more of the enzymes described herein could lead to inhibition of amino acid biosynthesis sufficient to inhibit plant growth. Thus, the instant plant amino acid biosynthetic enzymes could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314-331).

The production and use of plant gene-derived probes for use in genetic mapping is described in R. Bernatzky, R. and Tanksley, S. D. (1986) *Plant Mol. Biol. Reporter* 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149-154). Although current methods of FISH mapping favor use of large clones (several to several hundred KB; see Laan, M. et al. (1995) *Genome Research* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95-96), polymorphism of PCR-amplified fragments (CAPS; Sheffield, V. C. et al. (1993) *Genomics* 16:325-332), allele-specific ligation (Landegren, U. et al. (1988) *Science* 241:1077-1080), nucleotide extension reactions (Sokolov, B. P. (1990) *Nucleic Acid Res.* 18:3671), Radiation Hybrid Mapping (Walter, M. A. et al. (1997) *Nature Genetics* 7:22-28) and Happy Mapping (Dear, P. H. and Cook, P. R. (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding dihydrodipicolinate reductase, diaminopimelate epimerase, threonine synthase, threonine deaminase or S-adenosylmethionine synthetase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a dihydrodipicolinate reductase, diaminopimelate epimerase, threonine synthase, threonine deaminase or S-adenosylmethionine synthetase can be identified and obtained. This mutant plant can then be used to determine or confirm the natural function of the dihydrodipicolinate reductase, diaminopimelate epimerase, threonine synthase, threonine deaminase and S-adenosylmethionine synthetase gene product.

With respect to threoninine synthase, its substrate, O-phosphohomoserine, represents a branch point between the methionine and threonine biosynthetic pathways. It is believed that the enzymes threonine synthase and cystathionine-gamma-synthase actively compete for O-phosphohomoserine. Curien et al. (*FEBS Lett*. 390:85-90 (1996)) have characterized an *Arabidopsis thaliana* cDNA encoding an S-adenosylmethionine-regulated threonine synthase. This plant threonine synthase is activated by S-adenosylmethionine, a methionine derivative. When the level of S-adenosylmethionine is low, threonine synthase is inactive leading to reduced production of threonine, thus permitting more O-phosphohomoserine to be used for increased production of methionine. Removal of an approximately 30 amino acid region near the amino terminus of threonine synthase resulted in an enzyme that was active in the absence of S-adenosylmethionine. Those skilled in the art understand that the instant threonine synthase sequences may also contain an S-adenosylmethionine regulatory sequence. Consequently, deletion of the S-adenosylmethionine regulatory sequence should allow unregulated expression of threonine synthase in plants for threonine over-production. For example, the putative S-adenosylmethionine regulatory sequence, nucleotides 205-294 of SEQ ID NO:46, was deleted from corn clone cmm.pk0002.d3.fis (SEQ ID NO:46) to afford SEQ ID NO:56 (translated protein SEQ ID NO:57).

The amino acid sequences set forth in SEQ ID NOs:57, 59, 61, 63 and 65 are ones in which the S-adenosylmethionine regulatory sequences have been removed. The threonine synthase activity of these proteins is expected to be substantially unregulated because activation of these enzymes by S-adenosylmethionine is not necessary. As a consequence, these enzymes will be active even if the level of S-adenosylmethionine is low and plants expressing these unregulated threonine synthases will over-produce threonine. For example, the putative S-adenosylmethionine regulatory sequence, nucleotides 205-294 of SEQ ID NO:46, were deleted from corn clone cmm.pk0002.d3.fis (SEQ ID NO:46) to afford SEQ ID NO:56 (translated protein SEQ ID NO:57).

The amino acid sequences set forth in SEQ ID NOs:57, 59, 61, 63 and 65 are ones in which the S-adenosylmethionine regulatory sequences have been removed. The threonine synthase activity of these proteins is expected to be substantially unregulated because activation of these enzymes by S-adenosylmethionine is not necessary. As a consequence, they will continue to produce threonine even if the level of S-adenosylmethionine is low.

Those skilled in the art realize that removal of both the chloroplast transit sequence and putative S-adenosylmethionine regulatory sequence would permit expression of the truncated plant protein in *E. coli* (i.e., an Nco I site was added in SEQ ID NO:46 to remove amino acids 1-79 of SEQ ID NO:47).

Moreover, those skilled in the art further realize that removal of only the chloroplast transit sequence from the instant threonine synthase sequences would permit expression of the plant protein in *E. coli* for antibody production (i.e., an Nco I site was added in SEQ ID NO:46 to delete amino acids 1-46 of SEQ ID NO:47).

Those skilled in the art understand that the remaining instant threonine synthase sequences could also be modified in a similar way, as described above, for unregulated expression in plants (by deletion of the internal regulatory sequence), expression in *E. coli* (by deletion of the chloroplast transit sequence and the internal regulatory sequence) and expression in *E. coli* for antibody production (by deletion of the chloroplast transit sequence). Table 2 illustrates these modifications that could be made.

TABLE 2

Instant Threonine Synthase Sequences and Suggested Modifications

| Clone (SEQ ID NO:) | Nucleotides of the Internal Regulatory Sequence | Deletion of Internal Regulatory Sequence Affords SEQ ID NO: (translated protein) | Deletion of Chloroplast Transit Peptide |
|---|---|---|---|
| cpj1c.pk004.b4:fis (SEQ ID NO:44) | 169-258 | SEQ ID NO:58 (SEQ ID NO:59 - deletion of amino acids 45-74 of SEQ ID NO:45) | Delete amino acids 1-35 of SEQ ID NO:45 |

TABLE 2-continued

Instant Threonine Synthase Sequences and Suggested Modifications

| Clone (SEQ ID NO:) | Nucleotides of the Internal Regulatory Sequence | Deletion of Internal Regulatory Sequence Affords SEQ ID NO: (translated protein) | Deletion of Chloroplast Transit Peptide |
|---|---|---|---|
| Contig of: scb1c.pk003.113 sgs4c.pk003.h16 sr1.pk0003.f6 (SEQ ID NO:48) | 242-337 | SEQ ID NO:60 (SEQ ID NO:61 - deletion of amino acids 41-72 of SEQ ID NO:49) | Delete amino acids 1-30 of SEQ ID NO:49 |
| sdp4c.pk007.j10:fis (SEQ ID NO:50) | 168-263 | SEQ ID NO:62 (SEQ ID NO:63 - deletion of amino acids 44-75 of SEQ ID NO:51) | Delete amino acids 1-42 of SEQ ID NO:51 |
| wlm4.pk0013.f4:fis (SEQ ID NO:52) | 164-253 | SEQ ID NO:64 (SEQ ID NO:65 - deletion of amino acids 53-82 of SEQ ID NO:53) | Delete amino acids 1-47 of SEQ ID NO:53 |

The present invention also relates to a method to produce transgenic plants which have an increased methionine content due to the reduction of threonine synthase activity. Specific cosuppression of a threonine synthase gene in plants may increase methionine content. In higher plants, O-phosphohomoserine represents a branch point between the methionine and threonine biosynthetic pathways. It is believed that the enzymes threonine synthase and cystathionine-gamma-synthase actively compete for O-phosphohomoserine as substrate for threonine and methionine synthesis. It had been shown that a mutation in the threonine synthase gene results in an over-accumulation of soluble methionine in *Arabidopsis* (Bartlem et al., *Plant Physiol.* 123:101-110 (2000)). However, threonine synthase is an essential gene required for the synthesis of threonine and isoleucine. It is believed that a complete knockout of the threonine synthase will be lethal for plant growth and development.

There are two threonine synthase genes in soybean which are disclosed in SEQ ID NO:48 and SEQ ID NO:50. The identity between these two soybean genes in the open reading frame regions (ORF) regions is about 93.5%. However, the identity between these two genes in the 3'-UTR regions is only about 58%. It is believed that this diversity in the 3' UTR region affords an opportunity to specifically knockout only one of the threonine synthases in soybean. Either a seed specific promoter or a constitutive promoter can be used to knockout the threonine synthase specifically in seeds or constitutively in plant.

Example 13 describes the preparation of a construct to knockout only one of the threonine synthase genes in soybean. Moreover, the threonine synthase cosuppression construct may be introduced into plant cells by itself or with different gene combinations including, but not limited to, the following: (1) a threonine synthase cosuppression construct alone; (2) a threonine cosuppression construct+a methionine sink protein overexpression (such as 10 kD zein which is a seed storage protein from maize which is high in the sulfur containing amino acid methionine); and (3) a threonine synthase cosuppression construct+a methionine sink protein overexpression+other methionine pathway enzymes overexpression (such as cystathionine-gamma-synthase or/and serine acetyltransferase). In the gene combination approaches, the threonine synthase cosuppression will be combined with other methionine biosynthetic enzyme overexpression to further increase the methionine content in plant cells. A methionine-rich protein, such as maize 10 kD zein, will be over-expressed to incorporate the free methionine into its bound form. Total amino acids analyses may be done in transgenic soybean seeds.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 3 cDNA Libraries from Corn, Rice, Soybean and Wheat Tissues

| Library | Tissue | Clone |
|---|---|---|
| cc2 | Corn Callus, Partially Differentiated, 2 Weeks After Subculture | cc2.pk0031.c9 |
| cc3 | Corn Callus, Mature Somatic Embryo | cc3.mn0002.d2 |
| cen1 | Corn Endosperm 12 Days After Pollination | cen1.pk0064.f4 |
| chp2 | Corn Leaf, 11 Day Old Plant | chp2.pk0008.h4 |

TABLE 3-continued cDNA Libraries from Corn, Rice, Soybean and Wheat Tissues

| Library | Tissue | Clone |
|---|---|---|
| cmm | Corn clones for microarray study on metabolism | cmm.pk0002.d3:fis |
| cpj1c | Corn Pooled BMS Treated With Chemicals Related to Membrane Ionic Force*** | cpj1c.pk004.b4:fis |
| cs1 | Corn Leaf, Sheath 5 Week Old Plant | cs1.pk0058.g5 |
| csi1n | Corn Silk* | csi1n.pk0042.a3 |
| rls2 | Rice Leaf 15 Days After Germination, 2 Hours After Infection of Strain *Magaporthe grisea* 4360-R-67 (AVR2-YAMO); Susceptible | rls2.pk0017.d3 |
| rls48 | Rice Leaf 15 Days After Germination, 48 Hours After Infection of Strain *Magaporthe grisea* 4360-R-67 (AVR2-YAMO); Susceptible | rls48.pk0036.h10 |
| s2 | Soybean Seed, 19 Days After Flowering | s2.12b06 |
| scb1c | Soybean Embryogenic Suspension Culture Collected 10 Months Old (necrotic tissue) | scb1c.pk003.113 |
| sdp4c | Soybean Developing Pods (10-12 mm) | sdp4c.pk007.j10:fis |
| se1 | Soybean Embryo 7 Days After Flowering | se1.06a03 |
| se2 | Soybean Embryo 10 Days After Flowering | se2.pk0005.f1 |
| ses8w | Mature Soybean Embryo 8 Weeks After Subculture | ses8w.pk0010.h11 |
| sfl1 | Soybean Immature Flower | sfl1.pk0055.h7<br>sfl1.pk0031.h3 |
| sgs1c | Soybean Seeds 4 Hours After Germination | sgs1c.pk002.k12 |
| sgs4c | Soybean Cotyledon 14-21 Days After Germination (¼ yellow) | sgs4c.pk003.h16 |
| sr1 | Soybean Root From 10 Day Old Seedlings | sr1.pk0003.f6 |
| sre | Soybean Root Elongation 4-5 Days After Germination | sre.pk0044.f3 |
| wkm1c | Wheat Kernel Malted 55 Hours at 22 Degrees Celsius | wkm1c.pk0003.g4 |
| wle1n | Wheat Leaf From 7 Day Old Etiolated Seedling* | wle1n.pk0070.b8 |
| wlk1 | Wheat Seedlings 1 Hour After Treatment with Fungicide** | wlk1.pk0028.d3 |
| wlm4 | Wheat Seedlings 4 Hours After Inoculation With *Erysiphe graminis f.* sp. *tritici* | wlm4.pk0013.f4:fis |
| wlm24 | Wheat Seedlings 24 Hours After Inoculation With *Erysiphe graminis f.* sp. *tritici* | wlm24.pk0030.g4 |
| wr1 | Wheat Root From 7 Day Old Seedling | wr1.pk0085.h2<br>wr1.pk0086.d5<br>wr1.pk0103.h8 |
| wre1 | Wheat Root From 7 Day Old Etiolated Seedling | wre1.pk0002.c12 |
| wre1n | Wheat Root From 7 Day Old Etiolated Seedling* | wre1n.pk0082.b2<br>wre1n.pk170.d8 |

*These libraries were normalized essentially as described in U.S. Pat. No. 5,482,845
**Application of 6-iodo-2-propoxy-3-propyl-4(3H)-quinazolinone; synthesis and methods of using this compound are described in USSN 08/545,827, incorporated herein by reference.
***Membrane Traffic: chemicals used included tunicamycin, brefeldin A and cytochlasin B Ionic Traffic: chemicals used were valinomycin, bafilomycin A1, oligomycin and ionomycin cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences, or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification and Characterization of cDNA Clones

ESTs encoding plant amino acid biosynthetic enzymes were identified by conducting BLAST (Basic Local Alignment Search Tool; Altschul, S. F., et al., (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Polypeletides Homologous to Dihydrodipicolinate Reductase The BLASTX search using the nucleotide sequences from clones csi1n.pk0042.a3 and rls2.pk0017.d3 revealed similarity of the protein encoded by the cDNA to *Synechocystis* sp. dihydrodipicolinate reductase enzyme (DDBJ Accession No. D90899). BLAST pLog values were 12.60 and 11.68 for csi1n.pk0042.a3 and rls2.pk0017.d3, respectively.

The sequence of the entire cDNA insert in clone csi1n.pk0042.a3 was determined and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 36.72 versus the *Synechocystis* sp. dihydrodipicolinate reductase sequence. The sequence of a portion of the cDNA insert from clone rls2.pk0017.d3 is shown in SEQ ID NO:3; the deduced amino acid sequence of this cDNA is shown in SEQ ID NO:4. FIG. 2 presents an alignment of the amino acid sequences set forth in SEQ ID NO:2 and the *Synechocystis* sp. dihydrodipicolinate reductase sequence (SEQ ID NO:5). SEQ ID NO:2 is 40% identical to the *Synechocystis* sp. dihydrodipicolinate reductase sequence (SEQ ID NO:5). Sequence alignments were performed by the Clustal method of alignment (Higgins, D. G. and Sharp, P. M. (1989) *CABIOS* 5:151-153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626-645) using the Megalign program of the LASARGENE bioinformatics computing suite (DNASTAR Inc., Madison, Wis.).

Sequence alignments and BLAST scores and probabilities indicate that the instant nucleic acid fragments encode a nearly entire corn dihydropicolinate reductase, and a portion of a rice dihydropicolinate reductase. These sequences represent the first plant sequences encoding dihydropicolinate reductase.

Example 4

Characterization of cDNA Clones Encoding Diaminopimelate Epimerase

The BLASTX search using the nucleotide sequences from clones chp2.pk0008.h4, rls48.pk0036.h10, wlm24.pk0030.g4, and the contig sequences assembled from clones se2.pk0005.fl, ses8w.pk0010.h11, sfl1.pk0031.h3, and sgs1c.pk002.k12 revealed similarity of the proteins encoded by the cDNAs to diaminopimelate epimerase from *Synechocystis* sp. (DDBJ Accession No. D90917). The BLAST results for each of these ESTs are shown in Table 4:

TABLE 4

BLAST Results for Clones Encoding Polypeptides Homologous to Diaminopimelate Epimerase

| Clone | BLAST pLog Score DDBJ Accession No. D90917 |
|---|---|
| chp2.pk0008.h4 | 59.16 |
| rls48.pk0036.h10 | 40.82 |
| Contig of: se2.pk0005.fl ses8w.pk0010.h11 | 98.30 |

TABLE 4-continued

BLAST Results for Clones Encoding Polypeptides Homologous to Diaminopimelate Epimerase

| Clone | BLAST pLog Score DDBJ Accession No. D90917 |
|---|---|
| sfl1.pk0031.h3 sgs1c.pk002.k12 wlm24.pk0030.g4 | 23.46 |

The sequence of the entire cDNA insert in clone chp2.pk0008.h4 was determined and is shown in SEQ ID NO:6; the deduced amino acid sequence of this cDNA is shown in SEQ ID NO:7. The amino acid sequence set forth in SEQ ID NO:7 was evaluated by BLASTP, yielding a pLog value of 75.66 versus the *Synechocystis* sp. sequence. The sequence of a portion of the cDNA insert from clone rls48.pk0036.h10 is shown in SEQ ID NO:8; the deduced amino acid sequence of this cDNA is shown in SEQ ID NO:9. The nucleotide sequence of the contig assembled from clones se2.pk0005.fl, ses8w.pk0010.h01, sfl1.pk0031.h3, and sgs1c.pk002.k12 was determined and is shown in SEQ ID NO:10; the deduced amino acid sequence of this cDNA is shown in SEQ ID NO:11. The amino acid sequence set forth in SEQ ID NO:11 was evaluated by BLASTP, yielding a pLog value of 98.57 versus the *Synechocystis* sp. sequence. The sequence of a portion of the cDNA insert from clone wlm24.pk0030.g4 is shown in SEQ ID NO:12; the deduced amino acid sequence of this cDNA is shown in SEQ ID NO:13. FIGS. 3A and 3B present an alignment of the amino acid sequences set forth in SEQ ID NOs:7, 9, 11, and 13 and the *Synechocystis* sp. sequence (SEQ ID NO:14). The data in Table 5 represents a calculation of the percent identity of the amino acid sequences set forth in SEQ ID NOs: 7, 9, 11, and 13 and the *Synechocystis* sp. sequence.

TABLE 5

Percent Identity of Amino Acid Sequences Deduced From the Nucleotide Sequences of cDNA Clones Encoding Polypeptides Homologous to Diaminopimelate Epimerase

| Clone | SEQ ID NO. | Percent Identity to DDBJ Accession No. D90917 (SEQ ID NO:16) |
|---|---|---|
| chp2.pk0008.h4 | 7 | 59 |
| rls48.pk0036.h10 | 9 | 74 |
| Contig of: se2.pk0005.fl ses8w.pk0010.h11 sfl1.pk0031.h3 sgs1c.pk002.k12 | 11 | 72 |
| wlm24.pk0030.g4 | 13 | 65 |

Sequence alignments were performed by the Clustal method of alignment (Higgins, D. G. and Sharp, P. M. (1989) CABIOS 5:151-153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626-645) using the Megalign program of the LASARGENE bioinformatics computing suite (DNASTAR Inc., Madison, Wis.).

Sequence alignments and BLAST scores and probabilities indicate that the instant nucleic acid fragments encode a nearly entire corn diaminopimelate epimerase (chp2.pk0008.h4), a portion of a rice diaminopimelate epimerase (rls48.pk0036.h10), and an entire soybean diaminopimelate epimerase (se2.pk0005.f1, ses8w.pk0010.h11, sfl1.pk0031.h3, and sgs1c.pk002.k12), and a portion of a wheat diaminopimelate epimerase (wlm24.pk0030.g4). These sequences represent the first plant sequences encoding diaminopimelate epimerase enzyme.

Example 5

Characterization of cDNA Clones Encoding Threonine Synthase

The BLASTX search using the EST sequences from clones cc2.pk0031.c9, cs1.pk0058.g5, rls72.pk0018.e7, se1.06a03, sr1.pk0003.f6 and wr1.pk0085.h2 revealed similarity of the proteins encoded by the cDNAs to threonine synthase from *Arabidopsis thaliana* (GenBank Accession No. L41666). The BLAST results for each of these ESTs are shown in Table 6.

In addition, the BLASTX search using the sequences from clones cpj 1c.pk004.b4:fis (SEQ ID NO:44), cmm.pk0002.d3:fis (SEQ ID NO:46), scb1c.pk003.113, sgs4c.pk003.h16, sr1.pk0003.f6, sdp4c.pk007.j10:fis (SEQ ID NO:50) and wlm4.pk0013.f4:fis (SEQ ID NO:52) revealed similarity of the proteins encoded by the cDNAs to threonine synthase from *Oryza sativa* (NCBI General Identifier No. 34911416; SEQ ID NO:54) or *Solanum tuberosum* (NCBI General Identifier No. 20140867; SEQ ID NO:55). Shown in Table 6 are the BLASTP results obtained for the amino acid sequences of the threonine synthases encoded by the entire cDNA inserts comprising these cDNA clones.

TABLE 6

BLAST Results for Clones Encoding Polypeptides Homologous to Threonine Synthase

| Clone | BLAST pLog Score | Closest Similarity |
| --- | --- | --- |
| cc2.pk0031.c9 | 56.19 | GeneBank L41666 |
| cs1.pk0058.g5 | 8.00 | GeneBank L41666 |
| rls72.pk0018.e7 | 29.47 | GeneBank L41666 |
| se1.06a03 | 34.15 | GeneBank L41666 |
| sr1.pk0003.f6 | 21.13 | GeneBank L41666 |
| wr1.pk0085.h2 | 29.47 | GeneBank L41666 |
| cpj1c.pk004.b4:fis | 180.00 | NCBI General Identifier No. 34911416 |
| cmm.pk0002.d3:fis | 180.00 | NCBI General Identifier No. 34911416 |
| Contig of: scb1c.pk003.113 sgs4c.pk003.h16 sr1.pk0003.f6 | 180.00 | NCBI General Identifier No. 20140867 |
| sdp4c.pk007.j10:fis | 180.00 | NCBI General Identifier No. 20140867 |
| wlm4.pk0013.f4:fis | 180.00 | NCBI General Identifier No. 34911416 |

The sequence of the entire cDNA insert in clone cc2.pk0031.c9 was determined and is shown in SEQ ID NO:15; the deduced amino acid sequence of this cDNA is shown in SEQ ID NO:16. The amino acid sequence set forth in SEQ ID NO:16 was evaluated by BLASTP, yielding a pLog value of 166.11 versus the *Arabidopsis thaliana* sequence. BLASTN against dbest indicated identity of nucleotides 520 through 684 from cc2.pk0031.c9 with nucleotides 1 through 162 of a corn EST (GenBank Accession No. T18847). The sequence of a portion of the cDNA insert from clone cs1.pk0058.g5 is shown in SEQ ID NO:17; the deduced amino acid sequence of this cDNA is shown in SEQ ID NO:18. The sequence of a portion of the cDNA insert from clone rls72.pk0018.e7 is shown in SEQ ID NO:19; the deduced amino acid sequence of this cDNA is shown in SEQ ID NO:20. The sequence of a portion of the cDNA insert from clone se1.06a03 is shown in SEQ ID NO:21; the deduced amino acid sequence of this cDNA is shown in SEQ ID NO:22. The sequence of the entire cDNA insert in clone sr1.pk0003.f6 was determined and is shown in SEQ ID NO:23; the deduced amino acid sequence of this cDNA is shown in SEQ ID NO:24. The amino acid sequence set forth in SEQ ID NO:24 was evaluated by BLASTP, yielding a pLog value of 275.06 versus the *Arabidopsis thaliana* sequence. The sequence of a portion of the cDNA insert from clone wr1.pk0085.h2 is shown in SEQ ID NO:25; the deduced amino acid sequence of this cDNA is shown in SEQ ID NO:26. FIGS. 4A, 4B and 4C present an alignment of the amino acid sequences set forth in SEQ ID NOs:16, 18, 20, 22, 24, and 26 and the *Arabidopsis thaliana* sequence.

The nucleotide sequence corresponding to the entire cDNA insert in clone cpj1c.pk004.b4:fis is shown in SEQ ID NO:44; the amino acid sequence corresponding to the translation of nucleotides 37 through 1602 is shown in SEQ ID NO:45 (nucleotides 1603-1605 encode a stop). The nucleotide sequence corresponding to the entire cDNA insert in clone cmm.pk0002.d3:fis is shown in SEQ ID NO:46; the amino acid sequence corresponding to the translation of nucleotides 59 through 1636 is shown in SEQ ID NO:47 (nucleotides 1637-1639 encode a stop). The nucleotide sequence corresponding to the contig formed of the cDNA inserts in clones scb1c.pk003.113, sgs4c.pk003.h16 and sr1.pk0003.f6 is shown in SEQ ID NO:48; the amino acid sequence corresponding to the translation of nucleotides 122 through 1678 is shown in SEQ ID NO:49 (nucleotides 1679-1681 encode a stop). The nucleotide sequence corresponding to the entire cDNA insert in clone sdp4c.pk007j10: fis is shown in SEQ ID NO:50; the amino acid sequence corresponding to the translation of nucleotides 39 through 1601 is shown in SEQ ID NO:51 (nucleotides 1602-1604 encode a stop). The nucleotide sequence corresponding to the entire cDNA insert in clone wlm4.pk0003.f4:fis is shown in SEQ ID NO:52; the amino acid sequence corresponding to the translation of nucleotides 2 through 1597 is shown in SEQ ID NO:53 (nucleotides 1598-1600 encode a stop). FIGS. 9A, 9B, 9C, 9D, 9E and 9F show a multiple alignment of the amino acid sequences reported herein encoding threonine synthase (SEQ ID NOs:45, 47, 49, 51 and 53) to the *Oryza sativa* threonine synthase set forth in NCBI General Identifier No. 34911416 (SEQ ID NO:54) and the *Solanum tuberosum* sequence set forth in NCBI General Identifier No. 20140867 (SEQ ID NO:55). FIGS. 10A, 10B, 10C, 10D and 10E show a multiple alignment of the amino acid sequences reported herein encoding threonine synthase (minus the regulatory region) (SEQ ID NOs:57, 59, 61, 63 and 65) to the *Oryza sativa* threonine synthase set forth in NCBI General Identifier No. 34911416 (SEQ ID NO:54) and the *Solanum tuberosum* sequence set forth in NCBI General Identifier No. 20140867 (SEQ ID NO:55).

The data in Table 7 represents a calculation of the percent identity of the amino acid sequences set forth in SEQ ID NOs:16, 18, 20, 22, 24, and 26 and the *Arabidopsis thaliana* sequence (SEQ ID NO:27). Furthermore, the data in Table 6 represents a calculation of the percent identity of the amino acid sequences set forth in SEQ ID NOs:45, 47, 49, 51, 53, 57, 59, 61, 63 and 65 with either the *Oryza sativa* sequence (NCBI General Identifier No. 34911416; SEQ ID NO:54) or *Solanum tuberosum* sequence (NCBI General Identifier No. 20140867; SEQ ID NO:55).

TABLE 7

Percent Identity of Amino Acid Sequences Deduced From the Nucleotide Sequences of cDNA Clones Encoding Polypeptides Homologous to Threonine Synthase

| Clone | SEQ ID NO. | Percent Identity |
|---|---|---|
| cc2.pk0031.c9 | 16 | 81.0% to L41666 (SEQ ID NO:27) |
| cs1.pk0058.g5 | 18 | 81.0% to L41666 (SEQ ID NO:27) |
| rls72.pk0018.e7 | 20 | 55.3% to L41666 (SEQ ID NO:27) |
| se1.06a03 | 22 | 80.0% to L41666 (SEQ ID NO:27) |
| sr1.pk0003.f6 | 24 | 84.4% to L41666 (SEQ ID NO:27) |
| wr1.pk0085.h2 | 26 | 50.4% to L41666 (SEQ ID NO:27) |
| cpj1c.pk004.b4:fis | 45 | 82.8% to GI 34911416 (SEQ ID NO:54) |
| cmm.pk0002.d3:fis | 47 | 88.8% to GI 34911416 (SEQ ID NO:54) |
| Contig of: scb1c.pk003.113 sgs4c.pk003.h16 sr1.pk0003.f6 | 49 | 80.2% to GI 20140867 (SEQ ID NO:55) |
| sdp4c.pk007.j10:fis | 51 | 80.9% to GI 20140867 (SEQ ID NO:55) |
| wlm4.pk0013.f4:fis | 53m | 88.0% to GI 34911416 (SEQ ID NO:54) |
| cmm.pk0002.d3:fis minus regulatory sequence | 57 | 88.9% to GI 34911416 (SEQ ID NO:54) |
| cpj1c.pk004.b4:fis minus regulatory sequence | 59 | 84.8% to GI 34911416 (SEQ ID NO:54) |
| Contig of: scb1c.pk003.113 sgs4c.pk003.h16 sr1.pk0003.f6 minus regulatory sequence | 61 | 81.5% to GI 20140867 (SEQ ID NO:55) |
| sdp4c.pk007.j10:fis minus regulatory sequence | 63 | 81.6% to GI 20140867 (SEQ ID NO:55) |
| wlm4.pk0013.f4:fis minus regulatory sequence | 65 | 87.8% to GI 34911416 (SEQ ID NO:54) |

Sequence alignments were performed by the Clustal method of alignment (Higgins, D. G. and Sharp, P. M. (1989) *CABIOS* 5:151-153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626-645) using the Megalign program of the LASARGENE bioinformatics computing suite (DNASTAR Inc., Madison, Wis.).

Sequence alignments and BLAST scores and probabilities indicate that the instant nucleic acid sequences set forth in SEQ ID NOs:16, 18, 20, 22, 24, and 26 encode portions of a corn threonine synthase (cc2.pk0031.c9 and cs1.pk0058.g5), a portion of a rice threonine synthase (rls72.pk0018.e7), portions of a soybean threonine synthase (se1.06a03 and sr1.pk0003.f6), and a portion of a wheat threonine synthase (wr1.pk0085.h2). These sequences represent the first corn, rice, soybean, and wheat sequences encoding threonine synthase. Furthermore, sequence alignments and BLAST scores and probabilities indicate, that the instant nucleic acid sequences set forth in SEQ ID NOs:45, 47, 49, 51 and 53 encode full-length threonine synthases from corn (cpj1c.pk004.b4:fis; SEQ ID NO:45), corn (cmm.pk0002.d3:fis; SEQ ID NO:47), soybean (contig of: scb1c.pk003.113, sgs4c.pk003.h16 and sr1.pk0003.f6; SEQ ID NO:49), soybean (sdp4c.pk007.j10:fis; SEQ ID NO:51) and wheat (wlm4.pk0013.f4:fis; SEQ ID NO:53).

Example 6

Characterization of cDNA Clones Encoding Threonine Deaminase

The BLASTX search using the EST sequence from clone cen1.pk0064.f4 revealed similarity of the protein encoded by the cDNA to threonine deaminase from *Burkholderia capacia* (GenBank Accession No. U40630; pLog=31.38). The BLASTX search using the EST sequences from clones sfl1.pk0055.h7 and sre.pk0044.f3 revealed similarity of the proteins encoded by the cDNAs to threonine deaminase from *Solanum tuberosum* and *Burkholderia capacia* (EMBL Accession No. X67846 and GenBank Accession No. U40630, respectively). BLAST pLog values were 36.55 and 31.79 for sfl1.pk0055.h7, and 19.47 and 14.51 for sre.pk0044.f3.

The sequence of the entire cDNA insert in clone cen1.pk0064.f4 was determined and is shown in SEQ ID NO:28; the deduced amino acid sequence of this cDNA is shown in SEQ ID NO:29. The amino acid sequence set forth in SEQ ID NO:29 was evaluated by BLASTP, yielding a pLog value of 134.85 versus the *Burkholderia capacia* sequence. The sequence of a portion of the cDNA insert from clone sfl1.pk0055.h7 is shown in SEQ ID NO:30; the deduced amino acid sequence of this cDNA is shown in SEQ ID NO:31. The sequence of the entire cDNA insert in clone sre.pk0044.f3 was determined and is shown in SEQ ID NO:32; the deduced amino acid sequence of this cDNA is shown in SEQ ID NO:33. The amino acid sequence set forth in SEQ ID NO:33 was evaluated by BLASTP, yielding pLog values of 19.24 versus the *Solanum tuberosum* sequence and 15.19 versus the *Burkholderia capacia* threonine deaminase sequence. FIGS. 5A and 5B present an alignment of the amino acid sequences set forth in SEQ ID NOs:29, 31, and 33 and the *Burkholderia capacia* (SEQ ID NO:34) sequence. The data in Table 8 represents a calculation of the percent identity of the amino acid sequences set forth in SEQ ID NOs:29, 31, and 33, 35 and the *Burkholderia capacia* sequence.

TABLE 8

Percent Identity of Amino Acid Sequences Deduced From the Nucleotide Sequences of cDNA Clones Encoding Polypeptides Homologous to Threonine Deaminase

| Clone | SEQ ID NO. | Percent Identity to U40630 (SEQ ID NO:36) |
|---|---|---|
| cen1.pk0064.f4 | 29 | 61.0 |
| sfl1.pk0055.h7 | 31 | 47.9 |
| sre.pk0044.f3 | 33 | 46.0 |

Sequence alignments were performed by the Clustal method of alignment (Higgins, D. G. and Sharp, P. M. (1989) *CABIOS* 5:151-153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626-645) using the Megalign program of the LASARGENE bioinformatics computing suite (DNASTAR Inc., Madison, Wis.).

Sequence alignments and BLAST scores and probabilities indicate that the instant nucleic acid fragments encode a nearly entire corn threonine deaminase (cen1.pk0064.f4) and portions of a soybean threonine deaminase (sfl1.pk0055.h7 and sre.pk0044.f3). These sequences represent the first corn and soybean sequences encoding threonine deaminase.

Example 7

Characterization of cDNA Clones Encoding S-Adenosylmethionine Synthetase

The BLASTX search using the nucleotide sequence from clone cc3.mn0002.d2 revealed similarity of the protein encoded by the cDNA to S-adenosylmethionine synthetase from *Oryza sativa* (EMBL Accession No. Z26867; pLog=99.03). The sequence of the entire cDNA insert in clone cc3.mn0002.d2 was determined and is shown in SEQ ID NO:35; the deduced amino acid sequence of this cDNA is shown in SEQ ID NO:36. The nucleotide sequence set forth in SEQ ID NO:35 was evaluated by BLASTN, yielding a pLog value larger than 200 versus the *Oryza sativa* sequence. FIGS. 6A, 6B and 6C present an alignment of the nucleotide sequences set forth in SEQ ID NO:35 and the *Oryza sativa* sequence (SEQ ID NO:37). The nucleotide sequence in SEQ ID NO:35 is 88% identical over 1216 nucleotides to the nucleotide sequence of the *Oryza sativa* S-adenosylmethionine synthetase.

The BLASTX search using the nucleotide sequence from clone s2.12b06 revealed similarity of the protein encoded by the cDNA to S-adenosylmethionine synthetase from *Lycopersicon esculentum* (EMBL Accession No. Z24741; pLog=62.62). The sequence of the entire cDNA insert in clone s2.12b06 was determined and is shown in SEQ ID NO:38; the deduced amino acid sequence of this cDNA is shown in SEQ ID NO:39. The nucleotide sequence set forth in SEQ ID NO:38 was evaluated by BLASTN, yielding a pLog value larger than 200 versus the *Lycopersicon esculentum* sequence. FIGS. 7A, 7B and 7C present an alignment of the nucleotide sequences set forth in SEQ ID NO:38 and the *Lycopersicon esculentum* sequence (SEQ ID NO:40). The nucleotide sequence set forth in SEQ ID NO:38 is 82% identical over 1210 nucleotides to the *Lycopersicon esculentum* sequence.

The BLASTX search using the nucleotide sequence from the contig assembled from clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 revealed similarity of the protein encoded by the contig to S-adenosylmethionine synthetase from *Hordeum vulgare* (DDBJ Accession No. D63835) with a pLog value larger than 200. The nucleotide sequence of the contig assembled from clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 is shown in SEQ ID NO:41; the deduced amino acid sequence of this cDNA is shown in SEQ ID NO:42. FIGS. 8A, 8B and 8C present an alignment of the nucleotide sequence set forth in SEQ ID NO:41 and the *Hordeum vulgare* sequence (SEQ ID NO:43). The SEQ ID NO:41 is 92% identical to the *Hordeum vulgare* sequence.

Sequence alignments and BLAST scores and probabilities indicate that the instant nucleic acid fragments encode entire or nearly entire corn, soybean, or wheat S-adenosylmethionine synthetase. These sequences represent the first corn, soybean, or wheat sequences encoding S-adenosylmethionine synthetase.

Example 8

Expression of Chimeric Genes in Monocot Cells

A chimeric gene comprising a cDNA encoding an amino acid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers and under appropriate experimental conditions. Cloning sites (NcoI or SmaI) can be incorporated into the oligonucleotides to provide proper orientation of the DNA fragment when inserted into the digested vector pML103 as described below. The amplified DNA can then be digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 10801 University Boulevard, Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a plant amino acid biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of Agrobacterium tumefaciens.

The particle bombardment method (Klein et al., (1987) Nature 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules, Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks tissue can be transferred to regeneration medium (Fromm et al., (1990) Bio/Technology 8:833-839).

Example 9

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228-9238) can be used for expression of the instant amino acid biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed, and the isolated fragment is inserted into a pUC18 vector carrying the seed expression cassette.

Plant amino acid biosynthetic enzymes are known to be localized in the chloroplasts. Accordingly, for those enzymes (or polypeptides representing part of the instant amino acid biosynthetic enzymes) that lack a chloroplast targeting signal, the DNA fragment to be inserted into the expression vector can be synthesized by PCR with primers encoding a chloroplast targeting signal. For example, a chloroplast transit sequence equivalent to the cts of the small subunit of ribulose 1,5-bisphosphate carboxylase from soybean (Berry-Lowe et al. (1982) J. Mol. Appl. Genet. 1:483-498) may be used.

Soybean embroys may then be transformed with the expression vector comprising sequences encoding a plant amino acid biosynthetic enzyme. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810-812), the hygromycin phosphotransferase gene from plasmid pJR225 (from E. coli; Gritz et al. (1983) Gene 25:179-188) and the 3' region of the nopaline synthase gene from the T-DNA of the Ti plasmid of Agrobacterium tumefaciens. The seed expression cassette comprising the phaseolin 5' region, the fragment encoding the biosynthetic enzyme and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Analysis of Amino Acid Content of the Seeds of Transformed Plants

To analyze for expression of the chimeric genes in seeds and for the consequences of expression on the amino acid content in the seeds, a seed meal can be prepared by any of a number of suitable methods known to those skilled in the art. The seed meal can be partially or completely defatted, via hexane extraction for example, if desired. Protein extracts can be prepared from the meal and analyzed for enzyme activity. Alternatively the presence of any of the expressed enzymes can be tested for immunologically by methods well-known to those skilled in the art. To measure free amino acid composition of the seeds, free amino acids can be extracted from the meal and analyzed by methods known to those skilled in the art (Bieleski et al. (1966) Anal. Biochem. 17:278-293). Amino acid composition can then be determined using any commercially available amino acid analyzer. To measure total amino acid composition of the seeds, meal containing both protein-bound and free amino acids can be acid hydrolyzed to release the protein-bound amino acids and the composition can then be determined using any commercially available amino acid analyzer. Seeds expressing the instant amino acid biosynthetic enzymes and with altered lysine, threonine, methionine, cysteine and/or isoleucine content as compared to the wild type seeds can thus be identified and propagated.

To measure free amino acid composition of the seeds, free amino acids can be extracted from 8-10 milligrams of the seed meal in 1.0 mL of methanol/chloroform/water mixed in ratio of 12 v/5 v/3 v (MCW) at room temperature. The mixture can be vortexed and then centrifuged in an eppendorf microcentrifuge for about 3 min; approximately 0.8 mL of supernatant is then decanted. To this supernatant, 0.2 mL of chloroform is added followed by 0.3 mL of water. The mixture is then vortexed and centrifuged in an eppendorf microcentrifuge for about 3 min. The upper aqueous phase, approximately 1.0 mL, can then be removed and dried down in a Savant Speed Vac Concentrator. The samples are then hydrolyzed in 6N hydrochloric acid, 0.4% β-mercaptoethanol under nitrogen for 24 h at 110-120° C. Ten percent of the sample can then be analyzed using a Beckman Model 6300 amino acid analyzer using post-column ninhydrin detection. Relative free amino acid levels in the seeds are then compared as ratios of lysine, threonine, methionine, cysteine and/or isoleucine to leucine, thus using leucine as an internal standard.

Example 11

Expression of Chimeric Genes in Microbial Cells

The cDNAs encoding the instant plant amino acid biosynthetic enzymes can be inserted into the T7 E. coli expression vector pET24d (Novagen). Plasmid DNA containing a cDNA may be appropriately digested to release a nucleic acid fragment encoding the enzyme. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenyl/chloroform as described above. The prepared vector pET24d and fragment can then be ligated at 16° C. for 15 hours followed by transformation into DH5 electrocompetent cells (GIBCO BRL). Transformants can be selected on agar plates containing 2×YT media and 50 μg/mL kanamycin. Transformants containing gene encoding the enzyme are then screened for the correct orientation with respect to pET24d T7 promoter by restriction enzyme analysis.

Clones in the correct orientation with respect to the T7 promoter can be transformed into BL21 (DE3) competent cells (Novagen) and selected on 2×YT agar plates containing 50 μg/ml kanamycin. A colony arising from this transformation construct can be grown overnight at 30° C. in 2×YT media with 50 μg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 12

Evaluating Compounds for Their Ability to Inhibit the Activity of a Plant Amino Acid Biosynthetic Enzyme The plant amino acid biosynthetic enzymes described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant enzymes may be expressed separately as mature proteins, or may be co-expressed in E. coli or another suitable expression background. In addition, whether expressed separately or in combination, the instant enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzymes. Examples of such proteases include thrombin, enterokinase and factor Xa. However, any protease can be used which specifically cleaves the peptide connecting the fusion protein and the biosynthetic enzyme.

Purification of the instant enzymes, if desired, may utilize any number of separation technologies familiar to those skilled in the art of protein purification. Examples of such methods include, but are not limited to, homogenization, filtration, centrifuigation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the enzymes are expressed as fusion proteins, the purification protocol may include the use of an affinity resin which is specific for the fusion protein tag attached to the expressed enzyme or an affinity resin containing ligands which are specific for the enzyme. For example, an enzyme may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the biosynthetic enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the plant amino acid biosynthetic enzymes disclosed herein. Assays may be conducted under well known experimental conditions which permit optimal enzymatic activity. Examples of assays for many of these enzymes can be found in *Methods in Enzymology* Vol. V, (Colowick and Kaplan eds.) Academic Press, New York or *Methods in Enzymology* Vol. XVII, (Tabor and Tabor eds.) Academic Press, New York. Specific examples may be found in the following references, each of which is incorporated herein by reference: dihydrodipicolinate reductase may be assayed as described in Farkas et al. (1965) *J. Biol. Chem.* 240: 4717-4722, or Cremer et al. (1988) *J. Gen. Microbiol.* 134:3221-3229; diaminopimelate epimerase may be assayed as described in Work (1962) in *Methods in Enzymology* Vol. V, (Colowick and Kaplan eds.) 858-864, Academic Press, New York; threonine synthase may be assayed as described in Giovanelli et al. (1984) *Plant Physiol* 76: 285-292 or Curien et al. (1996) *FEBS Lett.* 390: 85-90; threonine deaminase may be assayed as described in Tomova et al. (1968) *Biochemistry (USSR)* 33: 200-208 or Dougall (1970) *Phytochemistry* 9: 959-964; and S-adenosylmethionine synthetase may be assayed as described in Mudd (1960) *Biochim. Biophys. Acta* 38:354-355 or Boerjan et al. (1994) *Plant Cell* 6:1401-1414.

Example 13

Preparation of Recombinant Constructs for Threonine Synthase Cosuppression

A recombinant construct (vector KS314, 8585 bp; SEQ ID NO:66 (FIG. 11)) was prepared that would be capable of selectively suppressing expression of a threonine synthase in soybeans. The soybean threonine synthase gene fragment was PCR-amplified from soybean clone sdp4c.pk007.j10:fis (SEQ ID NO:50) using the following primers: 5'-GAAT-TCGCGGCCGCTCCGGCTGGAAGGAGTTT-3' (MWG191; SEQ ID NO:67) and 5'-GAATTCGCGGCCGC-GATTTAATTACTTGTCAC-3' (MWG192; SEQ ID NO:68), which were designed to introduce Not I restriction enzyme sites at both ends of the soybean threonine synthase gene fragment. The specific threonine synthase gene fragment (SEQ ID NO:69) in this construct includes a part of the 3' open reading frame and the full 3' UTR region, nucleotides 1164-1604 and nucleotides 1605-2038 of SEQ ID NO:50, respectively. The resulting PCR fragment was subcloned into the intermediate cloning vector pGEM-T (Promega) according the manufacturer's protocol. The threonine synthase fragment was then released by Not I digestion and cloned into the Not I site of a soybean expression vector KS151, that has been been previously described in U.S. Patent Publication 2003/0036197 A1, published Feb. 20, 2003, and is herein incorporated by reference, to afford vector KS314 (SEQ ID NO:66). The gene specific threonine synthase fragment (SEQ ID NO:69) was driven by a Kti promoter and a Kti terminator for seed specific cosuppression of the threonine synthase gene.

What is claimed is:

1. An isolated polynucleotide comprising:
   (a) a nucleotide sequence encoding a polypeptide having threonine synthase activity, wherein the polypeptide has an amino acid sequence as set forth in SEQ ID NO:49;
   (b) the nucleotide sequence as set forth in SEQ ID NO:48 or a part thereof which is useful in co-suppression of endogenous threonine synthase activity in a transformed plant; or
   (c) the full-length complement of (a) or (b).

2. The polynucleotide of claim 1 wherein the nucleotide sequence comprises SEQ ID NO:48.

3. A vector comprising the polynucleotide of claim 1.

4. A recombinant DNA construct comprising the polynucleotide of claim 1 operably linked to at least one regulatory sequence.

5. A method for transforming a cell, comprising transforming a cell with the recombinant DNA construct of claim 4.

6. A cell comprising the recombinant DNA construct of claim 4.

7. A method for producing a plant comprising transforming a plant cell with the recombinant DNA construct of claim 4 and regenerating a plant from the transformed plant cell.

8. A plant comprising the recombinant DNA construct of claim 4.

9. A seed comprising the recombinant DNA construct of claim 4.

* * * * *